(12) United States Patent
Hammock et al.

(10) Patent No.: US 9,029,550 B2
(45) Date of Patent: *May 12, 2015

(54) CONFORMATIONALLY RESTRICTED UREA INHIBITORS OF SOLUBLE EPOXIDE HYDROLASE

(71) Applicant: The Regents of the University of California, Oakland, CA (US)

(72) Inventors: Bruce D. Hammock, Davis, CA (US); Paul D. Jones, Matawan, NJ (US); Christophe Morisseau, West Sacramento, CA (US); Huazhang Huang, Davis, CA (US); Hsing-Ju Tsai, Davis, CA (US); Richard Gless, Jr., Hayward, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/918,837

(22) Filed: Jun. 14, 2013

(65) Prior Publication Data

US 2013/0274476 A1 Oct. 17, 2013

Related U.S. Application Data

(60) Continuation of application No. 13/455,861, filed on Apr. 25, 2012, now Pat. No. 8,501,783, which is a division of application No. 11/685,674, filed on Mar. 13, 2007, now Pat. No. 8,188,289.

(60) Provisional application No. 60/782,172, filed on Mar. 13, 2006.

(51) Int. Cl.
| | |
|---|---|
| *C07D 211/60* | (2006.01) |
| *C07D 211/58* | (2006.01) |
| *C07D 209/08* | (2006.01) |
| *C07D 211/26* | (2006.01) |
| *C07D 211/96* | (2006.01) |
| *C07D 213/40* | (2006.01) |
| *C07D 235/30* | (2006.01) |
| *C07D 295/20* | (2006.01) |
| *C07D 295/205* | (2006.01) |
| *C07D 401/06* | (2006.01) |
| *C07D 401/12* | (2006.01) |
| *C07D 487/18* | (2006.01) |
| *C12Q 1/34* | (2006.01) |

(52) U.S. Cl.
CPC .......... *C07D 211/58* (2013.01); *C07D 209/08* (2013.01); *C07D 211/26* (2013.01); *C07D 211/96* (2013.01); *C07D 213/40* (2013.01); *C07D 235/30* (2013.01); *C07D 295/20* (2013.01); *C07D 295/205* (2013.01); *C07D 401/06* (2013.01); *C07D 401/12* (2013.01); *C07D 487/18* (2013.01); *C12Q 1/34* (2013.01)

(58) Field of Classification Search
CPC .................................................. C07D 295/185
USPC .......................................................... 546/245
See application file for complete search history.

(56) References Cited

U.S. PATENT DOCUMENTS

| | | | |
|---|---|---|---|
| 3,587,060 | A | 6/1971 | Quinn et al. |
| 3,703,537 | A | 11/1972 | Richter et al. |
| 3,755,415 | A | 8/1973 | Richter et al. |
| 4,252,954 | A | 2/1981 | Abdulla et al. |
| 5,273,982 | A | 12/1993 | Alig et al. |
| 5,314,902 | A | 5/1994 | Tjoeng et al. |
| 5,445,956 | A | 8/1995 | Hammock et al. |
| 5,492,918 | A | 2/1996 | Wild et al. |
| 5,637,113 | A | 6/1997 | Tartaglia et al. |
| 5,877,224 | A | 3/1999 | Brocchini et al. |
| 5,962,455 | A | 10/1999 | Blum et al. |
| 6,150,415 | A | 11/2000 | Hammock et al. |
| 6,211,241 | B1 | 4/2001 | Islam et al. |
| 6,287,285 | B1 | 9/2001 | Michal et al. |
| 6,290,722 | B1 | 9/2001 | Wang |
| 6,299,604 | B1 | 10/2001 | Ragheb et al. |
| 6,322,847 | B1 | 11/2001 | Zhong et al. |
| 6,329,395 | B1 | 12/2001 | Dugar et al. |
| 6,335,029 | B1 | 1/2002 | Kamath et al. |
| 6,344,358 | B1 | 2/2002 | Matsuoka et al. |
| 6,387,900 | B1 | 5/2002 | Pevarello et al. |
| 6,531,506 | B1 | 3/2003 | Kroetz et al. |
| 6,613,572 | B2 | 9/2003 | Matsuoka et al. |
| 6,693,202 | B1 | 2/2004 | Aggen et al. |
| 6,710,043 | B1 | 3/2004 | Yamada et al. |
| 2002/0090732 | A1 | 7/2002 | Matsuoka et al. |
| 2004/0014745 | A1 | 1/2004 | Yamada et al. |
| 2004/0054187 | A1 | 3/2004 | Mammen et al. |

(Continued)

FOREIGN PATENT DOCUMENTS

| | | |
|---|---|---|
| BF | WO 2004/014425 | 2/2004 |
| CA | 2 360 360 A1 | 7/2000 |

(Continued)

OTHER PUBLICATIONS

Archibald, "Antihypertensive Ureidopiperidines," 1980, Journal of Medicinal Chemistry, 23(8), pp. 857-861.
Japanese unexamined Patent Publication [Kokai] No. (JP-A)S58-118567, English Abstract.
Japanese unexamined Patent Publication [Kokai] No. (JP-A)H08-176159, English Abstract.
Japanese unexamined Patent Publication [Kokai] No. 2006/506320, English Abstract.

(Continued)

*Primary Examiner* — John Mabry
(74) *Attorney, Agent, or Firm* — DLA Piper LLP (US)

(57) ABSTRACT

Inhibitors of the soluble epoxide exemplary hydrolase (sEH) are provided that incorporate multiple pharmacophores and are useful in the treatment of diseases.

8 Claims, 5 Drawing Sheets

(56) References Cited

U.S. PATENT DOCUMENTS

| | | | |
|---|---|---|---|
| 2004/0092487 A1 | 5/2004 | Kroetz et al. | |
| 2004/0242637 A1 | 12/2004 | Hartman et al. | |
| 2005/0026844 A1 | 2/2005 | Hammock et al. | |

FOREIGN PATENT DOCUMENTS

| | | |
|---|---|---|
| DE | 123 466 A | 12/1976 |
| EP | 0 503 627 A1 | 9/1992 |
| EP | 1 031 564 A1 | 8/2000 |
| JP | 4-13666 A | 1/1992 |
| JP | 7-133224 A | 5/1995 |
| JP | 2001-158789 A | 6/2001 |
| JP | 2003-522120 A | 7/2003 |
| JP | 2004-002414 A | 1/2004 |
| RU | 2 208 608 C2 | 7/2003 |
| WO | WO 98/02435 | 1/1998 |
| WO | WO 99/07700 A1 | 2/1999 |
| WO | WO 99/09024 A1 | 2/1999 |
| WO | WO 00/42011 A1 | 7/2000 |
| WO | WO 00/48593 A1 | 8/2000 |
| WO | WO 00/72834 A2 | 12/2000 |
| WO | WO 00/72834 A3 | 12/2000 |
| WO | WO 00/76457 A2 | 12/2000 |
| WO | WO 00/76457 A3 | 12/2000 |
| WO | WO 01/42212 A1 | 6/2001 |
| WO | WO 02/14311 A2 | 2/2002 |
| WO | WO 02/14311 A3 | 2/2002 |
| WO | WO 03/009845 A1 | 2/2003 |
| WO | WO 03/061597 A2 | 7/2003 |
| WO | WO 03/061597 A3 | 7/2003 |
| WO | WO 03/062234 | 7/2003 |
| WO | WO 03/070242 A1 | 8/2003 |
| WO | WO 03/070727 A1 | 8/2003 |
| WO | WO 03/076426 A2 | 9/2003 |
| WO | WO 03/076426 A3 | 9/2003 |
| WO | WO 03/082861 A2 | 10/2003 |
| WO | WO 03/082861 A3 | 10/2003 |
| WO | WO 03/097586 A1 | 11/2003 |
| WO | WO 03/097618 A1 | 11/2003 |
| WO | WO 2004/007459 A2 | 1/2004 |
| WO | WO 2004/007459 A3 | 1/2004 |
| WO | WO 2004/024710 | 3/2004 |
| WO | WO 2004/026836 A2 | 4/2004 |
| WO | WO 2004/026836 A3 | 4/2004 |
| WO | WO 2004/063181 A1 | 7/2004 |
| WO | WO 2004/064730 A2 | 8/2004 |
| WO | WO 2004/064730 A3 | 8/2004 |
| WO | WO 2004/089296 A2 | 10/2004 |
| WO | WO 2004/094381 A1 | 11/2004 |
| WO | WO 2004/111009 A1 | 12/2004 |
| WO | WO 2004/111031 A1 | 12/2004 |
| WO | WO 2005/014580 A1 | 2/2005 |
| WO | WO 2005/030209 A1 | 4/2005 |
| WO | WO 2005/037199 A2 | 4/2005 |
| WO | WO 2005/037199 A3 | 4/2005 |
| WO | WO 2005/062882 | 7/2005 |
| WO | WO 2005/089763 A1 | 9/2005 |
| WO | WO 2005/113511 A1 | 12/2005 |
| WO | WO 2006/009741 A1 | 1/2006 |
| WO | WO 2006/014136 A1 | 2/2006 |
| WO | WO 2006/014359 A2 | 2/2006 |
| WO | WO 2006/014359 A3 | 2/2006 |
| WO | WO 2006/016039 A1 | 2/2006 |
| WO | WO 2006/045119 A2 | 4/2006 |

OTHER PUBLICATIONS

Japanese unexamined Patent Publication [Kokai] No. 2004/513096, English Abstract.
Japanese unexamined Patent Publication [Kokai] No. H05/509303, English Abstract.
AN 2000: 473143, CAPLUS abstract of Jefferson et al., "Solid-phase synthesis of a heterocyclic ethylenediamine-derivatized library," J. Comb. Chem., 2(5):441-444 (2000) abstract only.
Arand, M. et al., "Sequence similarity of mammalian epoxide hydrolases to the bacterial haloalkane dehalogenase and other related proteins" FEBS Lett., 338:251-256 (1994).
Argiriadi, M.A. et al., "Binding of alkylurea inhibitors to epoxide hydrolase implicates active site tyrosines in substrate activation" J. Biol. Chem., 275:15265-15270 (2000).
Bardin, C. W. (ed.), Current Therapy in Endocrinology and Metabolism, 6th Edition, Mosby—Year Book, Inc., St. Louis, MO 1997.
Beetham, J. et al., "cDNA cloning and expression of a soluble epoxide hydrolase from human liver" Arch. Biochem. Biophys., 305(1):197-201 (1993).
Beetham, J. et al., "Gene evolution of epoxide hydrolases and recommended nomenclature" DNA Cell Biol., 14(1):61-71 (1995).
Campbell, W.B., "New role for epoxyeicosatrienoic acids as anti-inflammatory mediators" Trends Pharmacol. Sci., 21:125-127 (2000).
Capdevila, J.H. et al., "Cytochrome P450 and arachidonic acid bioactivation: molecular and functional properties of the arachidonate monooxygenase" J. Lipid. Res., 41:163-181 (2000).
Carroll, M.A. et al., "A new class of lipid mediators: cytochrome P450 arachidonate metabolites" Thorax, 55:S13-16 (2000).
CAS Accession No. 71:18417; Accessed Dec. 12, 2006.
Chiasson, J. et al., "The efficacy of acarbose in the treatment of patients with non-insulin-dependent diabetes mellitus" Ann. Intern. Med., 121:928-935 (1994).
Coniff, R. et al., "Acarbose: a review of US clinical experience" Clin. Ther., 19:16-26 (1997).
Coniff, R. et al., "Multicenter, placebo-controlled trial comparing acarbose (BAY g5421) with placebo, tolbutamide, and tolbutamide-plus-acarbose in non-insulin-dependent diabetes mellitus" Am. J. Med., 98:443-451 (1995).
Defronzo, R. et al. (eds.), "Introduction" Diabetes Reviews, 5(4):293 (1997).
Dudda, A. et al., "Lipid oxidation products in ischemic porcine heart tissue" Chem. Phys. Lipids, 82:39-51 (1996).
Edwards et al., J. Med. Chem, 1996, 39, 1112-1124.
Fang, X., et al., "Effect of soluble epoxide hydrolase inhibition on epoxyeicosatrienoic acid metabolism in human blood vessels" Am. J. Physiol. Heart Circ. Physiol. 287:H2412-H2420 (2004).
Fisslthaler, B. et al., "Cytochrome P450 2C is an EDHF synthase in coronary arteries" Nature, 401:493-497 (1999).
Fourie et al., International Journal of Pharamceutics, vol. 279, Issues 1-2, Jul. 26, 2004, pp. 59-66.
Fretland, A.J. et al., "Epoxide hyrolases: biochemistry and molecular biology" Chem. Biol. Intereract., 129:41-59 (2000).
Fukushima, A. et al., "Cardiovascular effects of leukotoxin (9,10-epoxy-12-octadecenoate) and free fatty acids in dogs" Cardiovasc. Res., 22:213-218 (1988).
Gibson, G.G. and Skett, P., Introduction to Drug Metabolism, Second Ed., Chapman and Hall, New York pp. 199-210 (1994).
Goosen et al. Pharmaceutical Research, Jan. 2002, vol. 19, No. 1, pp. 13-19.
Grant, D. et al., "Molecular cloning and expression of murine liver soluble epoxide hydrolase" J. Biol. Chem., 268(23):17628-17633 (1993).
Haffner, S., "Management of dyslipidemia in adults with diabetes" Diabetes Care, 21:160-178 (1998).
Hammock, B.D. et al., "Chapter 3.18: Epoxide Hyrolases" in Comprehensive Toxicology. Oxford: Pergamon Press pp. 283-305 (1977).
Honig and Ingram, "Chronic Bronchitis, Emphysema, and Airways Obstruction" in Harrison's Principles of Internal Medicine, (Fauci et al., Eds.), 14th Ed., McGraw-Hill, New York, pp. 1451-1460 (1998).
Hwang, S.H. et al. "Orally Bioavailable Potent Soluble Epoxide Hydrolase Inhibitors," 2007, *Journal of Medicinal Chemistry*, pp. A-P.
International Search Report mailed on Jul. 30, 2007, for PCT Application No. PCT/US2007/006412 filed on Mar. 13, 2007, ten pages.
Ishizaki, T. et al., "Endothelin-1 potentiates leukotoxin-induced edematous lung injury" J. Appl. Physiol., 79:1106-1611 (1995).
Ishizaki, T. et al., "Leukotoxin, 9,10-epoxy-12-octadecenoate causes pulmonary vasodilation in rats" Am. J. Physiol., 268:L123-128 (1995).

(56) References Cited

OTHER PUBLICATIONS

Ishizaki, T. et al., "Leukotoxin, 9,10-epoxy-12-octadecenoate causes edematous lung injury via activation of vascular nitric oxide synthase" Am. J. Physiol., 269:L65-70 (1995).

Iwamoto, Y. et al., "Effect of combination therapy of troglitazone and sulphonylureas in patients with type 2 diabetes who were poorly controlled by sulphonylurea therapy alone" Diabet. Med., 13:365-370 (1996).

Kim, I-H. et al. "Design, Synthesis, and Biological Activity of 1,3-Disubstituted Ureas as Potent Inhibitors of the Soluble Epoxide Hydrolase of Increased Water Solubility," 2004, *Journal of Medicinal Chemistry*, vol. 47, No. 8, pp. 2110-2122.

Kricheldorf, H.R. et al. "Polykondensation von N-Aryloxycarbonyl-w-aminocarbonsauren and N-Phenoxycarbonyldipeptiden," 1975, *Die Angewandte Makromolekulare Chemie*, vol. 45, pp. 119-137.

Kwiterovich, P., "State-of-the-art update and review: clinical trials of lipid-lowering agents" Am. J. Cardiol., 82(12A):3U-17U (1998).

Mahler, R. et al., "Type 2 diabetes mellitus: update on diagnosis, pathophysiology, and treatment" J. Clin. Endocrinol. Metab., 84:1165-71 (1999).

McElroy, N.R. et al. "QSAR and Classification of Murine and Human Soluble Epoxide Hydrolase Inhibition by Urea-Like Compounds," 2003, *Journal of Medicinal Chemistry*, vol. 46, No. 6, pp. 1066-1080; pp. 1-39 of supporting information from http://pubs.acs.org/sub-scribe/journals/jmcmar/suppinfo/jm020269o/m020269o_s.pdf.

Migawa et al., Organic Letters, 2000, 2, pp. 3309-3311.

Moghaddam, M.F. et al., "Bioactivation of leukotoxins to their toxic diols by epoxide hydrolase" Nat. Med., 3:562-567 (1997).

Morisseau, C. et al. "Potent Urea and Carbamate Inhibitors of Soluble Epoxide Hydrolases," Aug. 1999, *P.N.A.S. USA*, vol. 96, pp. 8849-8854.

Morisseau, C. et al. "Structural Refinement of Inhibitors of Urea-Based Soluble Epoxide Hydrolases," *Biochemical Pharmacology*, 2002, vol. 63, pp. 1599-1608.

Morisseau, C., et al., "Inhibition of microsomal epoxide hydrolases by ureas, amides, and amines" Chem. Res, Toxicol. 14:409-415 (2001).

Nakagawa, Y., et al., "3-D QSAR analysis of inhibition of murine soluble epoxide hydrolase (MsEH) by benzoylureas, arylureas, and their analogues" Bioorg. Med. Chem. 8:2663-2673 (2000).

Newman, J.W. et al., "Evaluation of fish models of soluble epoxide hydrolase inhibition" Environ. Health Perspect., 109:61-66 (2001).

Node, K. et al., "Anti-inflammatory properties of cytochrome P450 epoxygenase-derived-eicosanoids" Science, 285:1276-1279 (1999).

Oesch, F. et al., "Mammalian epoxide hydrases: inducible enzymes catalyzing the inactivation of carcinogenic and cytotoxic metabolites derived from aromatic and olefinic compounds" Xenobiotica, 3:305-340 (1973).

Oltman, C.L., et al., "Epoxyeicosatrienoic acids and dihydroxyeicosatrienoic acids are potent vasodilators in the canine coronary microcirculation" Circ Res., 83:932-939 (1998).

Ozawa, T. et al., "Existence of leukotoxin 9,10-epoxy-12-octadecenoate in lung lavages from rats breathing pure oxygen and from patients with the adult respiratory distress syndrome" Am. Rev. Respir. Dis., 137:535-540 (1988).

Partial Supplementary European Search Report completed on Aug. 31, 2006, for EP Application No. 04 75 8831, seven pages.

Rautio et al., Eur. J. Pharm. Sci, 2000, 11, pp. 157-163.

Reynolds, H.Y., "Interstitial lung diseases" in Harrison's Principles of Internal Medicine.

(Fauci et al., Eds.), 14th Ed., McGraw-Hill, New York, pp. 1460-1466 (1998).

Sakai, T. et al., "Leukotoxin, 9,10-epoxy-12-octadecenoate inhibits mitochondrial respiration of isolated perfused not lung" Am. J. Physiol., 269:L326-331 (1995).

Sinal, C.J. et al., "Targeted disruption of soluble epoxide hydrolase reveals a role in blood pressure regulation" J. Biol. Chem., 275:40504-405010 (2000).

Speizer, "Environmental Lung Diseases," Harrison's Principles of Internal Medicine, (Fauci et al., Eds.), 14th Ed., 1998, McGraw-Hill, New York, pp. 1429-1436.

Turner, N. et al., "Insulin resistance, impaired glucose tolerance and non-insulin-dependent diabetes, pathologic mechanisms and treatment: Current status and therapeutics possibilities" Prog. Drug Res., 51:33-94 (1998).

United Kingdom Prospective Diabetes Study Group, "UKPDS 28: a randomized trial of efficacy of early addition of metformin in sulfonylurea-treated type 2 diabetes", Diabetes Care, 21: 87-92 (1998).

Walter, E. et al., "Transepithelial transport properties of peptidomimetic thrombin inhibitors in monolayers of a human intestinal cell line (Caco-2) and their correlation to in vivo data" Pharm. Res., 12: 360-365 (1995).

Watanabe, K. et al., "Studies on intestinal absorption of sulpiride (2): transepithelial transport of sulpiride across the human intestinal cell line caco-2" Biol. Pharm. Bull., 25:1345-1350 (2002).

Watanabe, T. et al. "Rapid Determination of Soluble Epoxide Hydrolase Inhibitors in Rat Hepatic Microsomes by High-Performance Liquid Chromatography with Eiectrospray Tandem Mass Spectrometry," 2001, *Analytical Biochemistry*, vol. 299, pp. 227-234.

Watanabe, T., et al., "In vitro metabolism of the mammalian soluble epoxide hydrolase inhibitor, 1-cyclohexyl-3-dodecyl-urea" Drug Metab. Dispos. 31(7):846-853 (2003).

Weintraub, N.L. et al., "Epoxide hydrolases regulate epoxyeicosatrienoic acid incorporation into coronary endothelial phospholipids" Am. J. Physiol., 277:H2098-2108 (1992).

Yamada, T. et al. "Biochemical Evidence for the Involvement of Tyrosine in Epoxide Activation During the Catalytic Cycle of Epoxide Hydrolase," Jul. 28, 2000, *The Journal of Biological Chemistry*, vol. 275, No. 30, pp. 23082-23088.

Yu, Z. et al., "Soluble epoxide hydrolase regulates hydrolysis of vasoactive epoxyeicosatrienoic acids" Circ. Res., 87:992-998 (2000).

Zeldin, D.C., et al., "Regio- and enantiofacial selectivity of epoxyeicosatrienoic acid hydration by cytosolic epoxide hydrolase" J. Biol. Chem., 268:6402-6407 (1993).

Zhao, X., et al., "Soluble epoxide hydrolase inhibition protects the kidney from hypertension-induced damage" J. Am. Soc. Nephrol. 15:1244-1253 (2004).

Zheng, J. et al, "Leukotoxin-Diol: a putative toxic mediator involved in acute respiratory distress syndrome" Am. J. Respir. Cell Mol. Biol., 25:434-438 (2001).

Figure 1. Pharmacokinetic profile of compounds with different piperidine substitutions given as a single oral dose of 0.3 mg/kg.
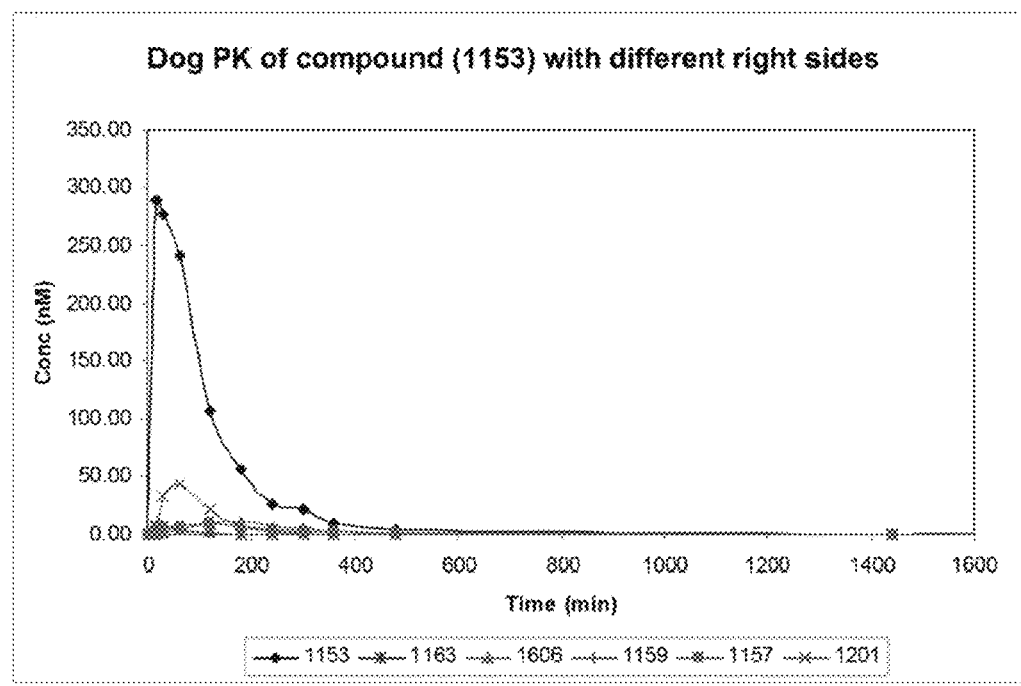

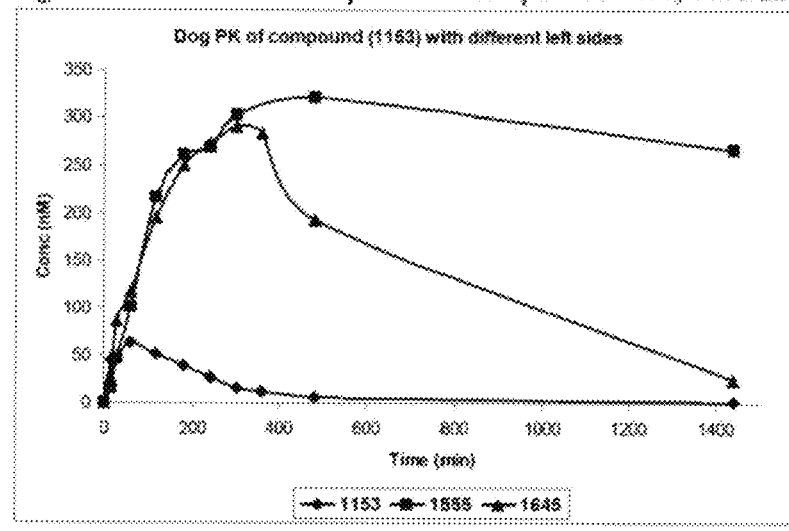
Figure 2. Pharmacokinetic profile of compounds 1153, 1555 and 1645.

Figure 3. Pharmacokinetic profile of compound 1153 following single oral administration 0.1 and 0.3 mg/kg orally.
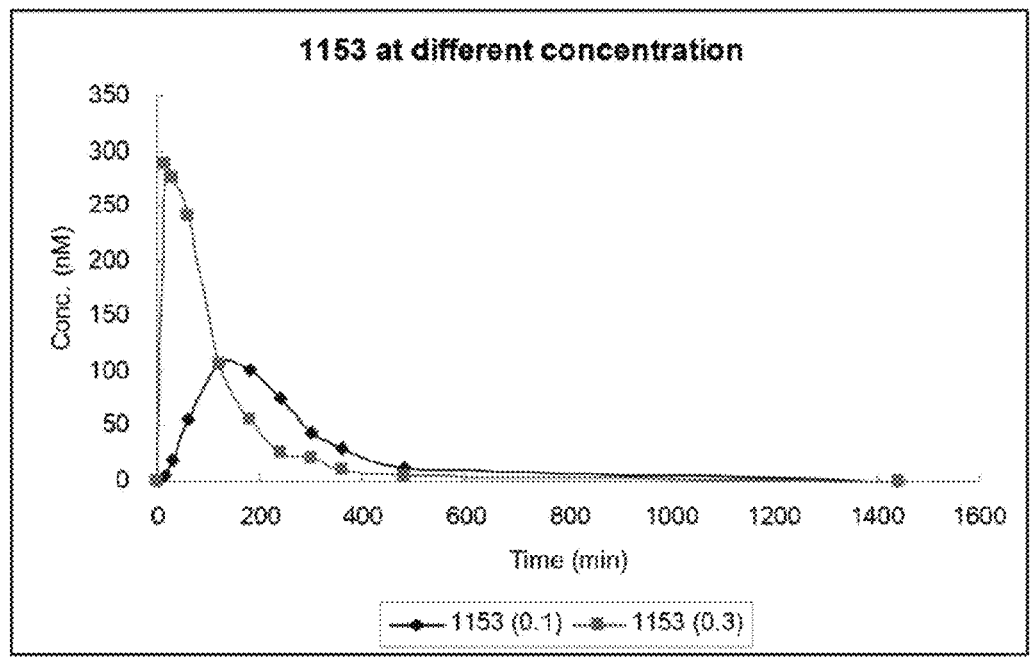

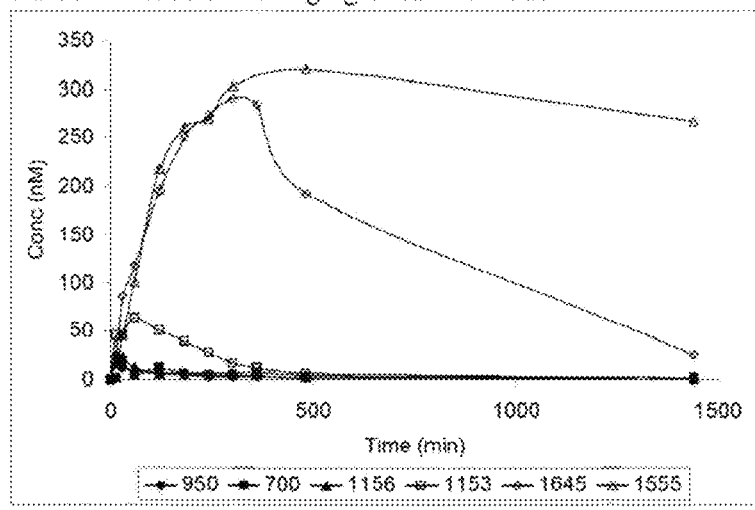
Figure 4. Pharmacokinetic profile of compound 1153 and other compounds following single oral administration 0.3 mg/kg of canine model

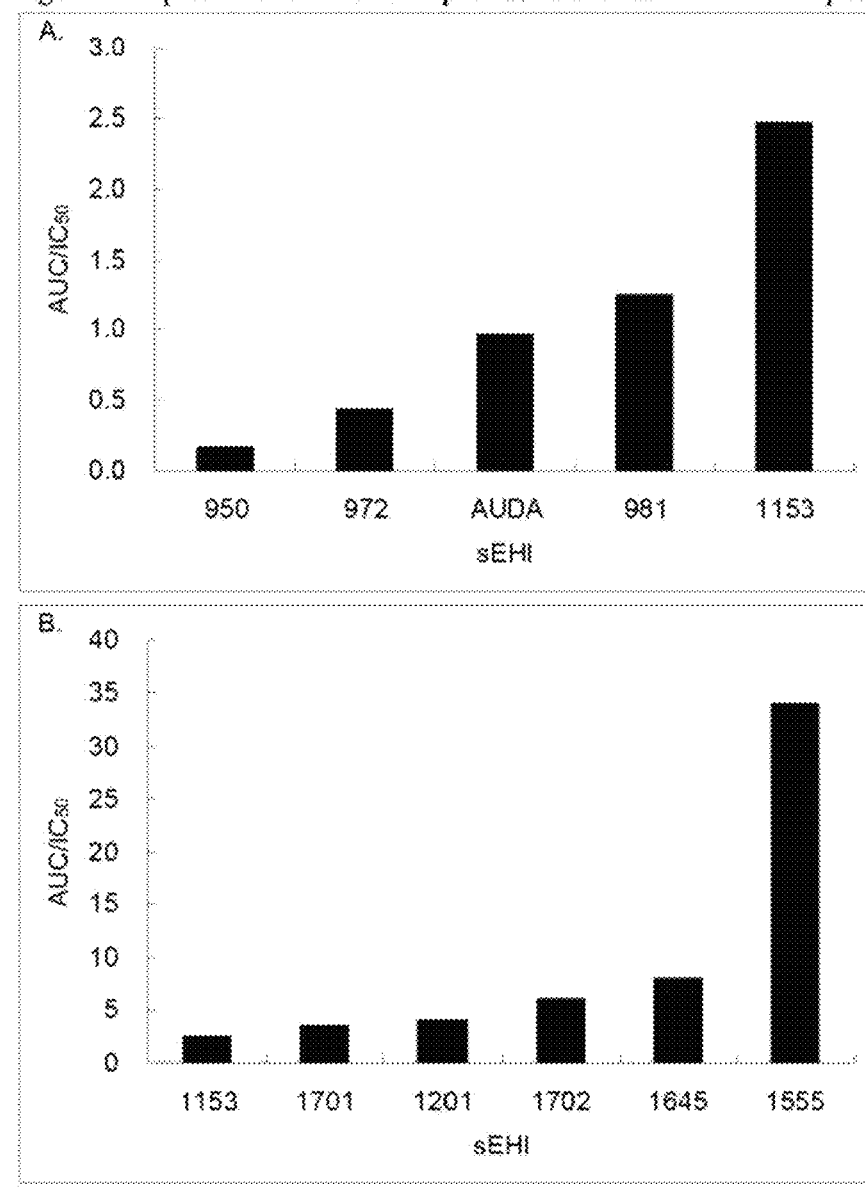
Figure 5. Exposure of selected compounds as a function of inverse potency.

CONFORMATIONALLY RESTRICTED UREA INHIBITORS OF SOLUBLE EPOXIDE HYDROLASE

CROSS-REFERENCES TO RELATED APPLICATIONS

This application is a continuation of U.S. patent application Ser. No. 13/455,861, filed Apr. 25, 2012, which is a divisional of U.S. patent application Ser. No. 11/685,674, filed Mar. 13, 2007, which claims the benefit of U.S. Provisional Patent Application No. 60/782,172, filed Mar. 13, 2006, each of which is incorporated by reference herein in its entirety.

STATEMENT AS TO RIGHTS TO INVENTIONS MADE UNDER FEDERALLY SPONSORED RESEARCH OR DEVELOPMENT

The U.S. Government as certain rights to the invention pursuant to contract ES02710 & HL078096 awarded by the National Institutes of Health.

BACKGROUND OF THE INVENTION

Epoxide hydrolases (EHs, EC 3.3.2.3) catalyze the hydrolysis of expoxides or arene oxides to their corresponding diols by the addition of water (see, Oesch, F., et al., *Xenobiotica* 1973, 3, 305-340). Some EHs play an important role in the metabolism of a variety of compounds including hormones, chemotherapeutic drugs, carcinogens, environmental pollutants, mycotoxins and other harmful foreign compounds.

There are two well-studied EHs, microsomal epoxide hydrolase (mEH) and soluble epoxide hydrolase (sEH). These enzymes are very distantly related, have different subcellular localization, and have different but partially overlapping substrate selectivities. The soluble and microsomal EH forms are known to complement each other in degrading some plant natural products (see, Hammock, B. D. et al., COMPREHENSIVE TOXICOLOGY Oxford: Pergamon Press 1977, 283-305 and Fretland, A. J., et al., *Chem. Biol. Intereract* 20000, 129, 41-59).

The major role of the sEH is in the metabolism of lipid epoxides including the metabolism of arachidonic acid (see, Zeldin, D. C., et al., *J. Biol. Chem.* 1993, 268, 6402-6407), linoleic acid (see, Moghaddam, M. F., et al., *Nat. Med.* 1997, 3, 562-567) acid, some of which are endogenous chemical mediators (see, Carroll, M. A., et al., *Thorax* 2000, 55, S13-16). Epoxides of arachidonic acid (epoxyeicosatrienoic acids or EETs) and other lipid epoxides and diols are known effectors of blood pressure (see, Capdevila, J. H., et al., *J. Lipid Res.* 2000, 41, 163-181), and modulators of vascular permeability (see, Oltman, C. L., et al., *Circ Res.* 1998, 83, 932-939). The vasodilatory properties of EETs are associated with an increased open-state probability of calcium-activated potassium channels leading to hyperpolarization of the vascular smooth muscle (see Fisslthaler, B., et al., *Nature* 1999, 401, 493-497). Hydrolysis of the arachidonate epoxides by sEH diminishes this activity (see, Capdevila, J. H., et al., *J. Lipid Res.* 2000, 41, 163-181). sEH hydrolysis of EETs also regulates their incorporation into coronary endothelial phospholipids, suggesting a regulation of endothelial function by sEH (see, Weintraub, N. L., et al., *Am. J. Physiol.* 1992, 277, H2098-2108). It has recently been shown that treatment of spontaneous hypertensive rats (SHRs) with selective sEH inhibitors significantly reduces their blood pressure (see, YU, Z., et al., *Circ. Res.*, 20000, 87, 992-998). In addition, it was claimed that male knockout sEH mice have significantly lower blood pressure than wild-type mice (see Sinal, C. J., et al., *J. Biol. Chem.* 2000, 275, 40504-404010), however subsequent studies demonstrated with with back breeding into C57b mice that 20-HETE levels increased compensating for the increase in plasma EETs (see, Luria, A. et al., *J. Biol. Chem.* 2007, 282:282:2891-2898.

The EETs have also demonstrated anti-inflammatory properties in endothelial cells (see, Node, K., et al., *Science*, 1999, 285, 1276-1279 and Campbell, W. B. *Trends Pharmacol. Sci.* 2000, 21, 125-127), in contrast, diols derived from epoxylinoleate (leukotoxin) perturb membrane permeability and calcium homeostats (see, Moghaddam, M. F., et al., *Nat. Med.* 1997, 3, 562-562), which results in inflammation that is modulated by nitric oxide synthase and endothelin-1 (see, Ishizaki, T., et al., *Am. J. Physiol.* 1995, 269, L65-70 and Ishizaki, T., et al., *J. Appl. Physiol.* 1995, 79, 1106-1611). Micromolar concentrations of leukotoxin reported in association with inflammation and hypoxia (see, Dudda, A., et al., *Chem. Phys. Lipids* 1996, 82, 39-51), depress mitochondrial respiration in vitro (see, Sakai, T., et al., *Am. J. Physiol.* 1995, 269, L326-331), and cause mammalian cardiopulmonary toxicity in vivo (see, Ishizaki, T., et al., *Am. J. Physiol.* 1995, 269, L65-70; Fukushima, A., et al., *Cardiovasc. Res.* 1998, 22, 213-218; and Ishizaki, T., et al., *Am. J. Physiol.* 1995, 268, L123-128). Leukotoxin toxicity presents symptoms suggestive of multiple organ failure and acute respirator distress syndrome (ARDS) see, Ozawa, T. et al., *Am. Rev. Respir. Dis.* 1988, 137, 535-540). In both cellular and organismal models, leukotoxin-mediated toxicity is dependent upon epoxide hydrolysis (see, Moghaddam, M. F., et al., *Nat. Med.* 1997, 3, 562-567; Morisseau C., et al., *Proc. Natl. Acad. Sci. USA* 1999, 96, 8849-8854; and Zheng J., et al., *Am. J. Respir. Cell Mol. Biol.* 2010, 25, 434-438), suggesting a role for sEH in the regulation of inflammation and vascular permeability. The bioactivity of these epoxy-fatty acids suggests that inhibition of vicinal-dihydroxy-lipid biosynthesis may have therapeutic value, making sEH a promising pharmacological target.

Recently, 1,3-disubstituted ureas, carbamates, and amides have been reported as new potent and stable inhibitors of sEH See, U.S. Pat. No. 6,150,415. Compounds 192 and 686 are representative structures for this type of inhibitors (FIG. 1, herein). These compounds are competitive tight-binding inhibitors with nanomolar $K_1$ values that interact stoichiometrically with purified recombinant sEH (see, Morisseau, C., et al., *Proc. Natl. Acad. Sci. USA* 1999, 96, 8849-8854). Based on the X-ray crystal structure, the urea inhibitors were shown to establish hydrogen bonds and to form salt bridges between the urea function of the inhibitor and residues of the sEH active site, mimicking features encountered in the reaction coordinate of epoxide ring opening by this enzyme (see, Argiriadi, M. A., et al., *Proc. Natl. Acad. Sci. USA* 1999, 96, 1637-10642 and Argiriadi, M. A., et al., *J. Biol. Chem.* 2009, 275, 15265-15270). These inhibitors efficiently reduced epoxide hydrolysis in several in vitro and in vivo models (see, Yu, Z., et al., *Circ. Res.* 2000, 87, 992-998; Morrisseau, C., et al., *Proc. Natl. Acad. Sci. USA* 19999, 96, 8849-8854; and Newman, J. W., et al. *Environ, Health Perspect*, 2001, 109, 61-66). Despite the high activity associated with these inhibitors there exists a need for compounds possessing similar or increased activities, preferably with improved solubility and/or pharmacokinetic properties to facilitate formulation and delivery.

The present invention provides such compounds along with methods for their use and compositions that contain them.

BRIEF SUMMARY OF THE INVENTION

In one aspect, the present invention provides a method for inhibiting a soluble epoxide hydrolase, comprising contacting the soluble epoxide hydrolase with an inhibiting amount of a compound having the formula (I):

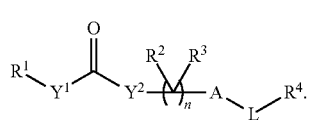

The symbol $R^1$ is a member selected from the group consisting of $C_1$-$C_5$alkyl, aryl$C_0$-$C_8$alkyl, $C_2$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is originally substituted with from 1 to 2 substituents each independently selected from the group consisting of $C_1$-$C_8$alkyl, $C_1$-$C_8$heteroaryl, aryl, and heteroaryl; wherein said cyclis portions are monocyclic or polycyclic. In one embodiment, the 1 to 2 substituents are each independently selected from the group consisting of $C_1$-$C_8$alkyl and $C_1$-$C_8$alkoxy. In one embodiment, the 1 to 2 substituents are each independently selected from the group consisting of $C_1$-$C_8$haloalkyl and $C_1$-$C_8$haloalkoxy.

The symbol $Y^1$ is selected from the group consisting of a bond, $C(R^5)_2$, $NR^5$ and O.

The symbol $Y^1$ is selected from the group consisting of a bond, $NR^5$ and O.

Each symbol $R^2$, $R^3$ and $R^5$ is independently selected from the group consisting of H, $C_1$-$C_8$alkyl and $COR^6$.

They symbol A is heterocyclyl, optionally substituted with from 1 to 2 $R^7$ substituents.

The symbol L is selected from the group consisting of a direct bond, $C_1$-$C_{12}$alkylene, $C_1$-$C_{12}$heteroalkylene, $C_3$-$C_6$cycloalkylene, arylene, heteroarylene, —CO—, —$SO_m$— and —Se—.

The symbol $R^4$ is selected from the group consisting of H, $C_1$-$C_8$alkyl, $C_1$-$C_6$alkenyl, $C_2$-$C_6$alkynyl, $C_1$-$C_8$heteroalkyl, aryl$C_0$-$C_8$alkyl, $C_3$-$C_{12}$cycloalkyl and heterocyclyl, each of which is optionally substituted. In one embodiment, each $C_1$-$C_8$alkyl, $C_2$-$C_6$alkenyl, $C_2$-$C_6$alkynyl, $C_1$-$C_8$heteroalkyl, aryl$C_0$-$C_8$alkyl, $C_3$-$C_{12}$cycloalkyl and heterocyclyl group is optionally substituted with from 1 to 2 substituents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl. In one embodiment, $R^4$ is selected from the group consisting of $C_1$-$C_8$alkyl and $C_1$-$C_8$alkoxy. In one embodiment, $R^4$ is selected from the group consisting of $C_1$-$C_8$haloalkyl and $C_1$-$C_8$haloalkoxy.

Each symbol $R^6$ is independently selected from the group consisting of H, $C_1$-$C_8$alkyl, OH, $C_1$-$C_8$alkoxy and amino.

Each symbol $R^7$ is selected from the group consisting of halo, nitro, $C_1$-$C_8$alkyl, $C_1$-$C_8$alkylamino, hydroxy$C_1$-$C_8$alkylamino, hydroxy$C_1$-$C_8$alkyl, halo$C_1$-$C_8$alkyl, carboxyl, hydroxyl, $C_1$-$C_8$alkoxy, $C_1$-$C_8$alkoxy$C_1$-$C_8$alkoxy, halo$C_1$-$C_8$alkoxy, thio$C_1$-$C_8$alkyl, aryl, aryloxy, $C_3$-$C_8$cycloalkyl, $C_3$-$C_8$cycloalkyl $C_1$-$C_8$alkyl, heteroaryl, aryl$C_1$-$C_8$alkyl, heteroaryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_4$-$C_8$alk(en)(yn)yl groups, cyano, formyl, $C_1$-$C_8$alkylcarbonyl, arylcabonyl, heteroarylcarbonyl, $C_1$-$C_8$alkoxycarbonyl, aryloxycarbonyl, aminocarbonyl, $C_1$-$C_8$alkylaminocarbonyl, $C_1$-$C_8$dialkylaminocarbonyl, arylaminocarbonyl, diarylaminocarbonyl, aryl$C_1$-$C_8$alkylaminocarbonyl, halo$C_1$-$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkyamino$C_1$-$C_8$alkyl, arylamino$C_1$-$C_8$alkyl, amino, $C_1$-$C_8$dialkylamino, arylamino, aryl$C_1$-$C_8$alkylamino, $C_1$-$C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfonyl, $C_1$-$C_8$sulfonyl, arylsulfinyl, arylsulfonyl, aminosulfonyl, $C_1$-$C_8$alkylaminosulfonyl, $C_1$-$C_8$dialkylaminosulfonyl and arylaminosulfonyl.

The subscript n is an integer of 0 to 1.

The subscript m is an integer of from 0 to 2.

The compounds include all pharmaceutically acceptable derivates thereof, such as salts, prodrugs, soft drugs, solvates and hydrates.

In a related aspect, the present invention provides methods of treating diseases modulated by soluble epoxide hydrolyses, the method comprising administering to a subject in need of such treatment an effective amount of a compound having a formula selected from formula (I) above. In one aspect, the effective amount is a therapeutically effective amount.

In other aspects, the present invention provides methods of reducing renal deterioration in a subject, the method comprising administering to the subject an effective amount of a compound of formula (I), above.

In a related aspect, the present invention provides methods method for inhibiting progression of nephropathy in a subject, the method comprising administering to the subject an effective amount of a compound of formula (I), above.

In another aspect, the present invention provides for reducing blood pressure in a subject, the method comprising administering to the subject an effective amount of a compound of formula (I), above.

In a related aspect, the present invention provides methods of inhibiting the proliferation of vascular smooth muscle cells in a subject, the method comprising administering to the subject an effective amount of a compound of formula (I), above.

In another aspect, the present invention provides methods of inhibiting the progression of an obstructive pulmonary disease, an interstitial lung disease, or asthma in a subject, the method comprising administering to the subject an effective amount of a compound of formula (I), above. The obstructive pulmonary disease can be, for example, chronic obstructive pulmonary disease ("COPD"), emphysema, or chronic bronchitis. The interstitial lung disease can be, for example, idiopathic pulmonary fibrosis, or one associated with occupational exposure to a dust.

In yet another aspect, the present invention provides compounds having a formula (I) above, as well as pharmaceutical compositions containing one or more of the subject compounds.

BRIEF DESCRIPTION OF THE DRAWINGS

FIG. 1. Pharmacokinetic profile of compounds with piperidine substitutions given as a single oral dose of 0.3 mg/kg.

FIG. 2. Pharmacokinetic profile of compounds 1153, 1155 and 1645 Compounds were administered orally to canines at 0.3 mg/kg.

FIG. 3. Pharmacokinetic profile of compound 1153 following single oral administration 0.1 and 0.3 mg/kg orally.

FIG. 4. Pharmacokinetic profile of compound 1153 and other compounds following single oral administration 0.3 mg/kg of canine model.

FIG. 5. Exposure of selected compounds as a function of inverse potency.

DETAILED DESCRIPTION OF THE INVENTION

Abbreviations and Definitions

"cis-Epoxyeicosatrieonic acids" ("EETs") are biomediators synthesized by cytochrome PL450 expoxygenases.

"Epoxide hydrolases" ("EH;" EC 3.3.2.3) are enzymes in the alpha/beta hydrolase fold family that add water to 3 membered cyclic ethers termed epoxides.

"Soluble epoxide hydrolase" ("sEH") is an enzyme which in endothelial, smooth muscle and other cell types converts EETs to dihydroxy derivates called dihydroxyeicosatrienoic acids ("DHETs"). The cloning and sequence of the murine sEH is set forth in Grant et al., *J. Biol. Chem.* 268(23)):17628-17633 (1993). The cloning, sequence, and accession members of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., *DNA Cell Biol.* 13(:6171 (1995). Soluble epoxide hydrolase represents a single highly conserved gene product with over 90% homology between rodent and human (Arand et al., *FEBS Lett.*, 338:251-256 (1994)).

The terms "treat", "treating" and "treatment" refer to any method of alleviating or abrogating a disease or its attendant symptoms.

The term "therapeutically effective amount" refers to that amount of the compound being administered sufficient to prevent or decrease the development of one or more of the symptoms of the disease condition or disorder being treated.

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

The term "compound" as used herein is intended to encompass not only the specified molecular entity but also its pharmaceutically acceptable, pharmacologically active derivatives, including, but not limited to, salts, prodrug conjugates such as esters and amides, metabolites, hydrates, solvates and the like.

The term "composition" as used herein is intended to encompass a product comprising the specified ingredient sin the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. in some embodiments, the subject is a human.

As used herein, the term "sEH-mediated disease or condition" and the like refers to a disease or condition characterized by less than or greater than normal, sEH activity. A sEH-mediated disease or condition is one in which modulation of sEH results in some effect on the underlying condition or disease (e.g., a sEH inhibitor or antagonist results in some improvement in patient well-being in at least some patients), "Parenchyma" refers to the tissue characteristic of an organ, as distinguished from associated connective or supporting issues.

"Chronic Obstructive Pulmonary Disease" or "COPD" is also sometimes known as "chronic obstructive airway disease", "chronic obstructive lung disease", and "chronic airways disease." COPD is generally defined as a disorder characterized by reduced maximal expiratory flow and slow forced emptying of the lungs. COPD is considered to encompass two related conditions, emphysema and chronic bronchitis. COPED can be diagnosed by the general practitioner using art recognized techniques, such as the patient's forced vital capacity ("FVC"), the maximum volume of air that can be forcibly expelled after a maximal inhalation. In the offices of general practitioners, the FVC is typically approximated by a 6 second maximal exhalation through a spirometer. The definition, diagnosis and treatment of COPD, emphysema, and chronic bronchitis are well known in the art and discussed in detail by, for example, Honig and Ingram, in Harrison's Principles of Internal Medicine, (Fauci et al., Eds.), 14th Ed., 1998, McGraw-Hill, New York, pp. 1451-1460 (hereafter "Harrison's Principles of Internal Medicine").

"Emphysema" is a disease of the lung characterized by permanent destructive enlargement of the airspaces distal to the terminal bronchioles without obvious fibrosis.

"Chronic" is a disease of the lung characterized by chronic bronchial secretions which last for most days of a month, for three months a year, for two years.

As the names imply, "obstructive pulmonary disease" and "obstructive lung disease" refer to obstructive diseases, as opposed to restrictive diseases. These diseases particularly include COPD, bronchial asthma and small airway disease.

"Small airway disease." There is a distinct minority of patients whose airflow obstruction is due, solely or predominantly to involvement of the small airways. These are defined as airways less than 2 mm in diameter and correspond to small cartilaginous bronchi, terminal bronchioles and respiratory bronchioles. Small airway disease (SAD) represents luminal obstruction by inflammatory and fibrotic changes that increase airway resistance. The obstruction may be transient or permanent.

The "interstitial lung diseases (ILDs)" are a group of conditions involving the alveolar walls, perialveolar tissues, and contiguous supporting structures. As discussed on the website of the American Lung Association, the tissue between the air sacs of the lung is the interstitium, and this is the tissue affected by fibrosis in the disease. Persons with the disease have difficulty breathing in because of the stiffness of the long tissue but, in contrast to persons with obstructive lung disease, have no difficulty breathing out. the definition, diagnosis and treatment of interstitial lung diseases are well known in the art and discussed in detail by, for example, Reynolds, H. Y., in Harrison's Principles of Internal Medicine, supra, at pp. 1350-1455. Reynolds notes that, while ILDs have various initiating events, the immunopathological responses of lung tissue are limited and the ILDs therefore have common features.

"Idiopathic pulmonary fibrosis," or "IPF," is considered the prototype ILD. Although it is idiopathic in that the cause is not known, Reynolds, supra, notes that the term refers to a well defined clinical entity.

"Bronchoalveolar lavage," or "BAL," is a test which permits removal and examination of cells from the lower respiratory tract and is used in humans as a diagnostic procedure for pulmonary disorders such as IPF. In human patients, it is usually performed during bronchoscopy.

As used herein, the term "alkyl" refers to a saturated hydrocarbon radical which may be straight-chain or branched-chain (for example ethyl, isopropyl, t-amyl, or 2,5-dimethylhexyl). This definition applies both when the term is used alone and when it is used as part of a compound term, such as "arylalkyl," "alkylamino" and similar terms. In some embodiments, alkyl groups are those containing 1 to 24 carbon atoms. All numerical ranges in this specification and claims are intended to be inclusive of their upper and lower limits. Additionally, the alkyl and heteroalkyl groups may be attached to other moieties at any position on the alkyl or heteroalkyl radical which would otherwise be occupied by a hydrogen atom (such as, for example, 2-pentyl, 2-methylpent-1-yl and 2-propyloxy). Divalent alkyl groups may be referred to as "alkylene," and divalent heteroalkyl groups may be referred to as "heteroalkylene," such as those groups used as linkers in the present invention. The alkyl, alkylene, and heteroalkylene moieties may also be optionally substituted with halogen atoms, or other groups such as oxo, cano, nitro, silyl, aklylamino, carboxyl hydroxyl, alkoxy aryloxy, and the like.

The terms "cycloalkyl" and "cycloalkylene" refer o a saturated hydrocarbon ring and includes bicyclic and polycyclic rings. Similarly, cycloalkyl and cycloaklylene groups having a heteroatom (e.g. N, O or S) in place of a carbon ring atom may be referred to as "heterocycloalkyl" groups are, for example, cyclohexyl, norbornyl, adamatyl, morpholinyl, thiomorpholinyl, dioxothiomorpholinyl, and the like. The cycloalkyl and heterocycloalkyl moieties may also be optionally substituted with halogen atoms, or other groups such as nitro, alkyl alklamino, carboxyl, alkoxy, aryloxy and the like. In some embodiments, cycloalkyl and cycloalkylene moieties are those having 3 to 12 carbon atoms in the ring (e.g., cyclohexyl, cyclooctyl, norbornyl, adamantyl, and the like). In some embodiments, heterocycloalkyl and heterocycloalkylene moieties are those having 1 to 3 hetero atoms in the ring (e.g., morpholinyl, thiomorpholinyl, dioxothiomorpholinyl, piperidinyl and the like). Additionally, term "cycloalkyl)alkyl" refers to a group having a cycloalkyl moiety attached to an alkyl moiety. Examples are cylohexylmethyl, cyclohexylethyl and cyclopentylpropyl.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears a oxygen substituent which is capable of covalent attachment to another hydrocarbon radical (such as, for example, methoxy, ethoxy and t-butoxyl).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g., N, O or S) in place of a carbon ring atom are referred to as "heteroaryl". Examples of aryl and heteroaryl groups are, for example, phenyl, naphthyl, biphenyl, diphenylmethyl, thienyl, pyridyl and quinoxalyl. The aryl and heteroaryl moieties may also be optionally substituted with halogen atoms, or other groups such as nitro, alkyl, alkylamino, carboxyl, alkoxy, phenoxy and the like. Additionally, the aryl and heteroaryl groups may be attached in other moieties a any position on the aryl or heteroaryl radical which would otherwise be occupied by a hydrogen atom (such as, for example, 2-pyridyl, 3-pyridyl and 4-pyridyl). Divalent aryl groups are "arylene", and divalent heteroaryl groups are referred to as "heteroarylene" such as those groups used as linkers in the present invention.

The terms "arylalkyl" and "alkylaryl", "refer to an aryl radical attached directly to an alkyl group. Likewise, the terms "arylalkenyl" and "aryloxyalkyl" refer to an alkenyl group, or an oxygen which is attached to an alkyl group, respectively. For brevity, aryl as part of a combined term as above, is meant to include heteroaryl as well. The term "aryloxy" refers to an aryl radical as described above which also bears an oxygen substituent which is capable of covalent attachment to another radical (such as, for example, phenoxy, napthtloxy, and pyridyloxy).

The terms "halo" or "halogen," by themselves or as part of another substituent, mean, unless otherwise stated, a fluorine, chlorine, bromine, or iodine atom. Additionally, terms such as "haloalkyl," and "haolalkoxy" are meant to include monohaloalkyl(oxy) and polyhaloalkyl(oxy). For example, the term "$C_1$-$C_6$haloalkyl" is mean to include trifluoromethyl, 2,3,3-trifluoroethyl, 4-chlorobutyl, 3-bromopropyl, and the like.

The term "hetero" as used in a "heteroatom-containing alkyl group" (a "heteroalkyl" group) or a "heteroatom-containing aryl group" (a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur or more than one non-carbon atom (e.g., sulfonamide). Similarly, the term "heteroalkyl" refers to an alkyl substituent that is heteroatom-containing, the terms "heterocyclic" "heterocycle" or "heterocyclyl" refer to a cyclic substituent or group that is heteroatom-containing and is either aromatic or non-aromatic. The terms "heteroaryl" and "heteroaromatic" respectively refer to "aryl" and "aromatic" substituents that are heteroatom-containing, and the like. The terms "heterocyclic" and "heterocyclyl" include the terms "heteroaryl" and "heteroaromatic". In some embodiments, heterocyclic moieties are those having 1 to 3 hetero atoms in the ring. Examples of heteroalkyl groups include alkoxy, alkoxyaryl, alkylsulfanyl-substituted silyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing cyclic nonaromatic groups are morpholinyl, piperazinyl, piperidinyl, etc.

The term "carboxylic acid analog" refers to a variety of groups having an acidic moiety that are capable of mimicking a carboxylic acid residue. Examples of such groups are sulfonic acids, sulfinic acids, phosphoric acids, phosphonic acids, phosphinic acids, sulfonamides, and heterocyclic moieties such as, for example, imidazoles, triazoles and tetrazoles.

The term "substituted" refers to the replacement of an atom or a group of atoms of a compound with another atom or group of atoms. For example, an atom or a group of atoms may be substituted with one or more of the following substituents or groups: halo, nitro, $C_1$-$C_8$alkyl, $C_1$-$C_8$alkylamino, hydroxy$C_1$-$C_8$alkyl, halo$C_1$-$C_8$alkyl, carboxyl, hydroxyl, $C_1$-$C_8$alkoxy, $C_1$-$C_8$alkoxy$C_1$-$C_8$alkoxy, thio$C_1$-$C_8$alkyl, aryl, aryloxy, $C_3$-$C_8$cycloalkyl, $C_3$-$C_8$cycloalkyl$C_1$-$C_8$alkyl, heteroaryl, aryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_4$-$C_8$alk(en)(yn)yl groups, cyano, formyl, $C_1$-$C_8$alkylcarbonyl, arylcabonyl, heteroarylcarbonyl, $C_1$-$C_8$alkoxycarbonyl, aryloxycarbonyl, aminocarbonyl, $C_1$-$C_8$alkylaminocarbonyl, $C_1$-$C_8$dialkylaminocarbonyl, arylaminocarbonyl, diarylaminocarbonyl, aryl$C_1$-$C_8$alkylaminocarbonyl, halo$C_1$-

$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkyamino$C_1$-$C_8$alkyl, arylamino$C_1$-$C_8$alkyl, amino, $C_1$-$C_8$dialkylamino, arylamino, aryl$C_1$-$C_8$alkylamino, $C_1$-$C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfinyl, $C_1$-$C_8$alkysulfonyl, arylsulfinyl, arylsulfonyl, aminosulfonyl, $C_1$-$C_8$alkylaminosulfonyl, $C_1$-$C_8$dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

General:

The present invention derives from the discovery that 1,3-disubstituted ureas (or the corresponding amides or carbamates, also referred to as the primary pharmacophore) can be further functionalized to provide more potent sEH inhibitors with improved physical properties. As described herein, the introduction of a heterocyclic moiety can increase water solubility and oral availability of sEH inhibitors (see below). The combination of these moieties provides a variety of compounds of increased water solubility.

The discovery of the heterocyclic pharmacophores has also led to the employment of combinatorial chemistry approaches for establishing a wide spectrum of compounds having sEH inhibitory activity. The polar pharmacophores divide the molecule into domains each of which can be easily manipulated by common chemical approaches in a combinatorial manner, leading to the design and confirmation of novel orally available therapeutic agents for the treatment of diseases such as hypertension and vascular inflammation. The agents of the present invention treat such diseases while simultaneously increasing sodium excretion, reducing vascular and renal inflammation, and reducing male erectile dysfunction. As shown below (see Examples and Figures), alterations in solubility, bioavailability and pharmacological properties leads to compounds that can alter the regulatory lipids of experimental animals increasing the relative amounts of epoxy arachidonate derivatives when compared either to their diol products or to the proinflammatory and hypertensive hydroxyeicosatetraenoic acids (HETEs). Since epoxy arachidonates are anti-hypertensive and anti-inflammatory, alerting the lipid ratios can lead to reduced blood pressure and reduced vascular and renal inflammation. This approach has been validated as reported in U.S. patent application Ser. Nos. 10/817,334 and 11/256,685 which are herein incorporated b reference in their entirety.

The heterocyclic group improves water solubility of sEH inhibitors as well as the specificity for the sEH, and a wide diversity of functionalities such as an ester, amide, carbamate, or similar functionalities capable of donating or accepting a hydrogen bond similarly can contribute to this polar group. For example, in pharmaceutical chemistry heterocyclic groups are commonly used to mimic carbonyls as hydrogen bond donors and acceptors. Of course the primary, secondary and tertiary pharmacophore groups can be combined in a single molecule with suitable spacers to improve activity or present the inhibitor as a prodrug.

Methods of Inhibiting Soluble Epoxide Hydrolases:

In view of the above, the present invention provides, in one aspect, a method for inhibiting a soluble epoxide hydrolase, comprising contacting the soluble epoxide hydrolase with an inhibiting amount of a compound having the formula (I):

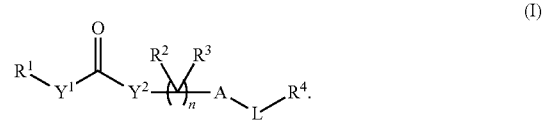

The symbol $R^1$ is a member selected from the group consisting of $C_1$-$C_8$alkyl, aryl$C_6$-$C_8$alkyl, $C_3$-$C_{12}$cycloalkyl and heterocyclyl each of which is optionally substituted. In one embodiment each $C_1$-$C_8$alkyl, aryl $C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cyclic portions are monocyclic or polycyclic. In one embodiment, the 1 to 2 substituents are each independently selected from the group consisting of $C_1$-$C_8$alkyl, $C_1$-$C_8$alkoxy. In one embodiment, the 1 to 2 substituents are each independently selected from the group consisting of $C_1$-$C_8$haloalkyl and $C_1$-$C_8$haloalkoxy.

The symbol $Y^1$ is selected from the group consisting of a bond, $C(R^5)_2$; $NR^5$ and O. The symbol $Y^2$ is selected from the group consisting of a bond, $NR^5$ and O.

Each symbol $R^2$, $R^3$ and $R^5$ is independently selected from the group consisting of H, $C_1$-$C_8$alkyl and $COR^6$.

The symbol A is heterocyclyl, optionally substituted with from 1 to 2 $R^7$ substituents.

The symbol L is selected from the group consisting of a direct bond, $C_1$-$C_{12}$heteroalkylene, $C_3$-$C_6$cycloalkylene, arylene, heteroarylene, —CO—, —$SO_m$— and —Se—.

The symbol $R^4$ is selected from the group consisting of H, $C_1$-$C_8$alkyl, $C_2$-$C_6$alkenyl, $C_2$-$C_6$alkynyl, $C_1$-$C_8$heteroalkyl, aryl$C_6$-$C_8$alkyl, $C_3$-$C_{12}$cycloalkyl and heterocyclyl, each of which is optionally substituted. In one embodiment, each $C_1$-$C_8$alkyl, $C_2$-$C_6$alkenyl, $C_2$-$C_6$alkynyl, $C_1$-$C_8$heteroalkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, halo, $C_1$-$C_8$heteroalkyl, aryl$C_0$-$C_8$alkyl, $COR^6$, $SW(O)_mR^6$ and heteroaryl. In one embodiment, $R^4$ is selected from the group consisting of $C_1$-$C_8$alkyl and $C_1$-$C_8$ alkoxy. In one embodiment, $R^4$ is selected from the group consisting of $C_1$-$C_8$haloalkyl and $C_1$-$C_8$haloalkoxy.

Each symbol $R^7$ is selected from the group consisting of halo, nitro, $C_1$-$C_8$alkyl, $C_1$-$C_8$alkylamino, hydroxy$C_1$-$C_8$alkyl, halo$C_1$-$C_8$alkyl, carboxyl, hydroxyl, $C_1$-$C_8$alkoxy, $C_1$-$C_8$alkoxy$C_1$-$C_8$alkoxy, halo$C_1$-$C_8$alkoxy, thio$C_1$-$C_8$alkyl, aryl, aryloxy, $C_3$-$C_8$cycloalkyl, $C_3$-$C_8$cycloalkyl $C_1$-$C_8$alkyl, heteroaryl, aryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_4$-$C_8$alk(en)(yn)yl groups, cyano, formyl, $C_1$-$C_8$alkylcarbonyl, arylcarbonyl, heteroarylcarbonyl, $C_1$-$C_8$alkoxycarbonyl, aryloxycarbonyl, amminocarbonyl, $C_1$-$C_8$alkylaminocarbonyl, $C_1$-$C_8$dialkylaminocarbonyl, arylaminocarbonyl, diarylaminocarbonyl, aryl$C_1$-$C_8$alkylaminocarbonyl, halo$C_1$-$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkylamino$C_1$-$C_8$alkyl arylamino$C_1$-$C_8$alkyl, amino, $C_1$-$C_8$dialkylamino, arylamino, aryl$C_1$-$C_8$alkylamino $C_1$-$C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfinyl, $C_1$-$C_8$alkylsulfonyl, arylsulfinyl, arylsulfonyl, amimosulfonyl, $C_1$-$C_8$alkylaminosulfonyl, $C_1$-$C_8$dialkylaminosulfonyl and arylaminosulfonyl.

The subscript n is an integer of 0 to 1.

The subscript m is an integer of from 0 to 2.

The compounds include all pharmaceutically acceptable derivatives thereof, such as salts, prodrugs, solvates and hydrates.

In other embodiments $Y^1$ is $NR^5$. In further embodiments $Y^2$ is a bond. In still further embodiments $Y^2$ is $NR^5$. In still other embodiments $Y^2$ is O.

In other embodiments $Y^2$ is $NR^5$. In further embodiments $Y^1$ is a bond. In still other embodiments $Y^1$ is $C(R)^5)_2$. In further embodiments $Y^1$ is O. In still further embodiments $Y^1$ is $NR^5$.

In other embodiments $R^2$, and $R^3$ and $R^5$ are H.

In further embodiments, A is selected from the group consisting of piperidinyl, 1,3,5-triaza-tricyclo[3.3.1.13,7]decyl, indolyl, pyridyl, morpholinyl and benzimidazolyl. In still other embodiments A is piperidinyl. In other embodiments A is 1,3,5-triaza-tricyclo[3.3.1.13,7]decyl. In still further embodiments A is indolyl. In other embodiments A is pyridyl. In other embodiments A is morpholinyl. In other embodiments A is benzimidazolyl.

In still other embodiments the compound has the formula:

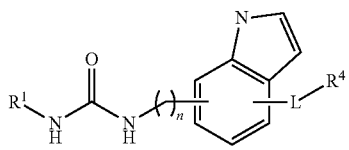

wherein $R^1$ is a member selected from the group consisting of $C_1$-$C_8$alkyl, aryl$C_0$-$C_8$alkyl, $C_3$-$C_{12}$cycloalkyl and heterocyclyl, each of which are optionally substituted. In further embodiments, each of $C_1$-$C_8$alkyl, aryl$C_0$-$C_8$alkyl, $C_3$-$C_{12}$cycloalkyl and heterocyclyl are optionally substituted with from 1 to 2 substituents each independently selected from the group consisting of $C_1$-$C_8$alkyl, $C_1$-$C_8$heteroalkyl, aryl, heteroaryl wherein said cycloalkyl portions are monocyclic or polycyclic.

Within these embodiments, L is selected from the group consisting of a direct bond, $C_1$-$C_{12}$heteroalkylene, —CO— and —$SO_m$—; and $R^4$ is selected from the group consisting of H, $C_1$-$C_8$alkyl, aryl$C_6$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2, In other embodiments the compound has the formula:

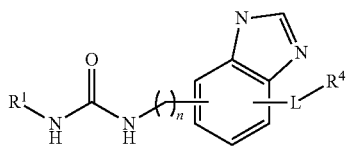

wherein $R^1$ is a member selected from the group consisting of $C_1$-$C_8$alkyl, aryl$C_0$-$C_8$alkyl, $C_3$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —$SO_m$—; and $R^4$ is selected from the group consisting of H, $C_1$-$C_8$alkyl, aryl$C_6$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substituent each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

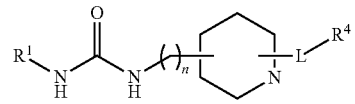

wherein $R^1$ is a member selected from the group consisting of $C_1$-$C_8$alkyl, aryl$C_0$-$C_8$alkyl, $C_3$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_2$-$C_{12}$heteroalkylene, —CO— and —$SO_m$—; and $R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_9$-$C_8$alkyl, $C_3$-$C_{12}$cycloalkyl and heterocyclyl is optionally substituted with from 1 to 2 substituent each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Without these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

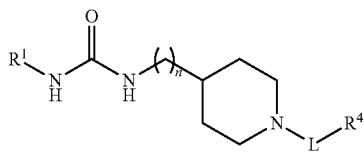

wherein $R^1$ is a member selected from the group consisting of $C_1$-$C_8$alkyl, aryl$C_0$-$C_8$alkyl, $C_3$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —SO$_m$—; and $R^4$ is selected from the group consisting of H, $C_1$-$C_8$alkyl, aryl$C_0$-$C_{12}$cycloalkyl and heterocyclyl, each of which is optionally substituted. In one embodiment, each $C_1$-$C_8$alkyl, aryl$_0$$C_8$alkyl, $C_3$-$C_{12}$cycloalkyl and heterocyclyl is optionally substituted with from 1 to 2 substituents each independently selected from the group consisting of $C_1$-$C_8$alkyl, halo, $C_1$-$C_8$heteroalkyl, aryl$C_0$-$C_8$alkyl, COR$^6$, S(O)$_m$R$^6$ and heteroaryl. In one embodiment, $R^4$ is selected from the group consisting of $C_1$-$C_8$alkyl and $C_1$-$C_8$alkoxy. In one embodiment, $R^4$ is selected from the group consisting of $C_1$-$C_8$haloalkyl and $C_1$-$C_8$haoloalkoxy.

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

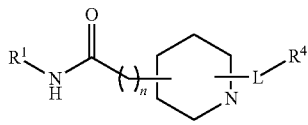

wherein $R^1$ is a member selected from the group consisting of $C_1$-$C_8$alkyl, aryl$C_0$-$C_8$alkyl, $C_3$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —SO$_m$—; and $R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl$C_0$-$C_8$alkoxy and amino;

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

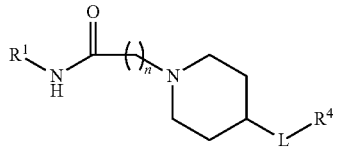

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —SO$_m$—; and $R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substitutents each independently selected from the group consisting of $C_1$-$C_8$alkyl, halo, $C_1$-$C_8$heteroalkyl, aryl$C_0$-$C_8$alkyl, COR$^6$, S(O)$_m$R$^6$ and heteroaryl.

Within these embodiments, each $R^6$ is independently selected from the group consisting of H, $C_1$-$C_8$alkyl, $C_1$-$C_8$-alkoxy and amino;
the subscript n is an integer of 0 to 1; and
the subscript m is an integer of 0 to 2.

In other embodiments the compound has the formula:

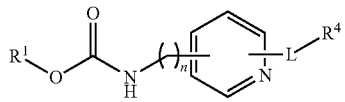

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —SO$_m$—; and $R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substitutents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

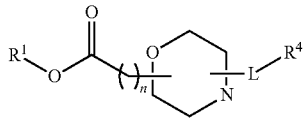

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —$SO_m$—; and
$R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substitutents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

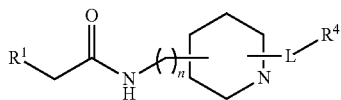

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —$SO_m$—; and
$R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substitutents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$alkoxy and amino;
the subscript n is an integer of 0 to 1; and
the subscript m is an integer of 0 to 2.

In other embodiments the compound has the formula:

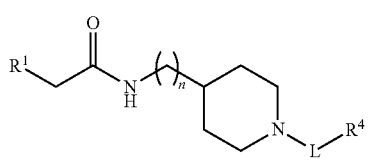

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —$SO_m$—; and
$R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each In other embodiments the compound has the formula:

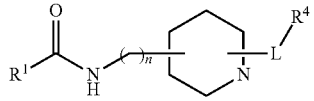

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —$SO_m$—; and
$R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substitutents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$-alkoxy and amino;
the subscript n is an integer of 0 to 1; and
the subscript m is an integer of 0 to 2.

In other embodiments the compound has the formula:

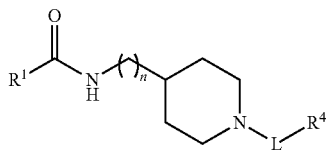

wherein $R^1$ is a member selected from the group consisting of $C_1$-$C_8$alkyl, aryl$C_0$-$C_8$alkyl, $C_1$-$C_{12}$cycloalkyl and heterocyclyl, each of which is optionally substituted. In one embodiment each $C_1$-$C_8$alkyl, aryl$C_0$-$C_8$alkyl, $C_3$-$C_{12}$cycloalkyl and heterocyclyl is optionally substituted with from 1 to 2 substituents each independently selected from the group consisting of $C_1$-$C_8$alkyl, $C_1$-$C_8$heteroalkyl, aryl, heteroaryl; wherein said cycloalkyl portions are monocyclic or polycyclic.

Within these embodiments, L is selected from the group consisting of a direct bond, $C_1$-$C_{12}$heteroalkylene, —CO— and —$SO_m$—; and
$R^4$ is selected from the group consisting of H, $C_1$-$C_8$alkyl, aryl$C_0$-$C_8$alkyl, $C_3$-$C_{12}$cycloalkyl and heterocyclyl, each of which is optionally substituted. In one embodiment, each $C_1$-$C_8$alkyl, aryl$C_0$-$C_8$alkyl, $C_3$-$C_{12}$cycloalkyl and heterocyclyl is optionally substituted with from 1 to 2 substitutents each independently selected from the group consisting of $C_1$-$C_8$alkyl, halo, $C_1$-$C_8$heteroalkyl, aryl$C_0$-$C_8$alkyl, $COR^6$, $S(O)_mR^6$ and heteroaryl.

Within these embodiments, each $R^6$ is independently selected from the group consisting of H, $C_1$-$C_8$alkyl, $C_1$-$C_8$-alkoxy and amino;
the subscript n is an integer of 0 to 1; and
the subscript m is an integer of 0 to 2.

In any of the above embodiments $R^1$ is $C_1$-$C_8$alkyl. In any of the above embodiments $R^1$ is selected from the group consisting of dodecyl and t-butyl. In any of the above embodiments $R^1$ is aryl$C_0$-$C_8$alkyl. In any of the above embodiments $R^1$ is phenyl. In any of the above embodiments $R^1$ is $C_1$-$C_{12}$cycloalkyl. In any of the above embodiments $R^1$ is adamantyl. In any of the above embodiments $R^1$ is cycloheptyl or cyclohexyl. In any of the above embodiments $R^1$ is $C_3$-$C_{12}$cycloalkyl. In any of the above embodiments $R^1$ is adamantyl. In any of the above embodiments $R^1$ is cycloheptyl. In any of the above embodiments of $R^1$, the group is optionally substituted. In any of the above embodiments, the $R^1$ group is optionally substituted with from 1 to 2 substituents. In any of the above embodiments the 1 to 2 substituents are each independently selected from the group consisting of $C_1$-$C_8$alkyl and $C_1$-$C_8$alkoxy. In any of the above embodiments embodiment, the 1 to 2 substituents are each independently selected from the group consisting of $C_1$-$C_8$haloalkyl and $C_1$-$C_8$haloalkoxy.

In any of the above embodiments L is a direct bond. In any of the above embodiments L is $C_1$-$C_{12}$heteroalkylene. In any of the above embodiments L is —CO—. In any of the above embodiments L is —$SO_2$—.

In any of the above embodiments $R^4$ is selected from the group consisting of H, $C_1$-$C_8$alkyl, aryl$C_0$-$C_8$alkyl, $C_1$-$C_8$alkoxy and heterocyclyl. In any of the above embodiments, $R^4$ is selected from the group consisting of $C_1$-$C_8$haloalkyl and $C_1$-$C_8$haloalkoxy.

In any of the above embodiments $R^6$ is H. In any of the above embodiments $R^6$ is $C_1$-$C_8$alkyl.

In any of the above embodiments n is 0. In any of the above embodiments n is 1.

In other embodiments, the compound is selected from the group consisting of the compounds of Examples 1-0 and Tables 1-4 and 5a and 5b.

In any of the above embodiments the compounds include all pharmaceutically acceptable derivatives thereof, such as salts, prodrugs, solvates and hydrates.

Assays to Monitor Soluble Epoxide Hydrolase Activity:

Additionally, the present invention provides a variety of assays and associated methods for monitoring soluble epoxide hydrolase activity, particularly the activity that has been modulated by the administration of one or more of the compounds provided above.

In one group of embodiments, the invention provides methods for reducing the formation of a biologically active diol produced by the action of a soluble epoxide hydrolase, the method comprising contacting the soluble epoxide hydrolase with an amount of a compound of formula (I) above, sufficient to inhibit the activity of the soluble epoxide hydrolase and reduce the formation of the biologically active diol.

In another group of embodiments, the invention provides methods for stabilizing biologically active epoxides in the presence of a soluble epoxide hydrolase, the method comprising contacting the soluble epoxide hydrolase with an amount of a compound of formula (I), sufficient to inhibit the activity of the soluble epoxide hydrolase and stabilize the biologically active epoxide.

In each of these groups of embodiments, the methods can be carried out as part of an in vitro assay or the methods can be carried out in vivo by monitoring blood titers of the respective biologically active epoxide or diol.

Epoxides and diols of some fatty acids are biologically important chemical mediators and are involved in several biological processes. The strongest biological data support the action of oxylipins as chemical mediators between the vascular endothelium and vascular smooth muscle. Epoxy lipids are anti-inflammatory and anti-hypertensive. Additionally, the lipids are thought to be metabolized by beta-oxidation, as well as by epoxide hydration. The soluble epoxide hydrolase is considered o be the major enzyme involved in the hydrolytic metabolism of these oxylipins. The compounds of formula (I) can inhibit the epoxide hydrolase and stabilize the epoxy lipids both in vitro and in vivo. This activity results in a reduction of hypertension in four separate rodent models. Moreover, the inhibitors show a reduction in renal inflammation associated with and independent of the hypertensive models.

More particularly, the present invention provides methods for monitoring a variety of lipids in both the arachidonate and linoleate cascade simultaneously in order to address the biology of the system. A GLC-MS system or a LC-MS method can be used to monitor over 740 analytes in a highly quantitative fashion in a single injection. The analytes include the regioisomers of the arachidonate epoxides (EETs), the diols (DHETs), as well as other P450 products including HETEs. Characteristic products of the cyclooxygenase, lipoxygenase, and peroxidase pathways in both the arachidonate and linoleate series can also be monitored. Such methods are particularly useful as being predictive of certain disease states. The oxylipins can be monitored in mammals following the administration of inhibitors of epoxide hydrolase. Generally, EH inhibitors increase epoxy lipid concentrations at the expense of diol concentrations in body fluids and issues.

Other compounds for use in this aspect of the invention are those inhibitors of formula (I) in which the primary pharmacophore is separated from a secondary and/or tertiary pharmacophore by a distance that approximates the distance between the terminal carboxylic acid and an epoxide functional group in the natural substrate.

Methods of Treating Diseases Modulated by Soluble Epoxide Hydrolases:

In another aspect, the present invention provides methods of treating diseases, especially those modulated by soluble epoxide hydrolases (sEH). The methods generally involve administering to a subject in need of such treatment an effective amount of a compound having a formula (I) above. The dose, frequency and timing of such administering will depend in large part on the selected therapeutic agent, the nature of the conditions or disorders, the formulation being administered and the discretion of the attending physician. Preferably, the compositions and compounds of the invention and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on e disease target, the patient, and the route of administration. Dosages are administered orally in the range of about 0.05 mg/kg to about 20 mg/kg, more preferably in the range of about 0.05 mg/kg o about 2 mg/kg, most preferably in the range of about 0.05 mg/kg to about 0.2 mg per kg of body weight per day. The dosage employed for the topical administration will of course, depend on the size of the area being treated.

It has previously been shown that inhibitors of soluble epoxide hydrolase ("sEH") can reduce hypertension. See, e.g., U.S. Pat. No. 6,351,506. Such inhibitors can be useful in controlling the blood pressure of persons with undesirably high blood pressure including those who suffer from diabetes.

In some embodiments, compounds of formula (I) are administered to a subject in need of treatment for hypertension, specifically renal, hepatic, or pulmonary hypertension; inflammation, specifically renal inflammation, vascular inflammation, and lung inflammation; adult respiratory distress syndrome; diabetic complications; end stage renal disease; Raynaud syndrome and arthritis.

Methods for Inhibiting Progression of Kidney Deterioration (Nephropathy) and Reducing Blood Pressure:

In another aspect of the invention, the compounds of the invention can reduce damage to the kidney, and especially damage to kidneys from diabetes, as measured by albuminuria. The compounds of the invention can reduce kidney deterioration (nephropathy) from diabetes even in individuals who do not have high blood pressure. The conditions of therapeutic administration are as described above.

cis-Epoxyeicosanitrienoic acids ("EETs") can be used in conjunction with the compounds of the invention to further reduce kidney damage. EETs, which are epoxides of arachidonic acid, are known o be effectors of blood pressure, regulators of inflammation, and modulators of vascular permeability. Hydrolysis of the epoxides by sEH dimities this activity. Inhibition of sEH raises the level of EETs since the rate at which the EETs are hydrolyzed into DHETs is reduce. Without wishing to be bound by theory, it is believed that raising the level of EETs interferes with damage to kidney cells by the microvasculature changes and other pathologic effects of diabetic hyperglycemia. Therefore, raising the EET level in the kidney is believed to project the kidney from progression from microalbuminuria to end stage renal disease.

EETs are well known in the art. EETs useful in the methods of the present invention include 14,15-EET, 8,9-EET and 11,12-EET, and 5,6 EETs, in that order of preference. Preferably, the EETs are administered as the methyl ester, which is more stable. Persons of skill will recognize that the EETs are regioisomers, such as 8S,9R- and 14R, 15S-EET, 8,9-EET, 11,12-EET, and 14R,15S-EET, are commercially available from, for example, Sigma-Aldrich (catalog nos. E5516, E541, and E5766, respectively, Sigma-Aldrich Corp., St. Louis, Mo.).

EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present invention, these favorable properties are believed to protect the vasculature and organs during renal and cardiovascular disease states.

It is now believed that sEH activity can be inhibited sufficiently to increase the levels of EETs and thus augment the effects of administering sEH inhibitors by themselves. his permits EETs to be used in conjunction with one or more sEH inhibitors to reduce nephropathy in the methods of the invention. It further permits EETs to be used in conjunction with one or more sEH inhibitors to reduce hypertension, or inflammation, or both. Thus, medicaments of EETs ca be made which can be administered in conjunction with one or more sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In some embodiments, the EETs, the compound of the invention, or both, are provided in a material that permits them to be released over time to provide a longer duration of action. Slow release coating are well known in the pharmaceutical art; the choice of the particular slow release coating is not critical to the practice of the present invention.

EETs are subject to degradation under acidic conditions. Thus, if the EETs are to be administered orally, it is desirable that the are protected from degradation in the stomach. Conveniently, EETs for oral administration may be coated to permit them to passage the acidic environment of the stomach into the basic environment of the intestines. Such coatings are well known in the art. For example, aspirin coated with so-called "enteric coatings" is widely available commercially.

Such enteric coating may be used to project EETs during passage through the stomach. An exemplary coating is set forth in the Examples.

While the anti-hypertensive effects of EETs have been recognized, EETs have not been administered to treat hypertension because it was thought endogenous sEH would hydrolyse the EETs too quickly for them to have any useful effect. Surprisingly, it was found during the course of the studies underlying the present invention that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in a least some improvement in symptoms or pathology, it may not be sufficient in all cases to inhibit progression of kidney damage fully, or to the extent intended. This is particularly rue where the diseases or other factors have reduced the endogenous concentrations of EETs below those normally present in healthy individuals. Administration of exogenous EETs in conjunction with a sEH inhibitor is therefore expected to be beneficial and to augment the effects of the sEH inhibitor in reducing the progression of diabetic nephropathy.

The present invention can be used with regard to any and all forms of diabetes to the extent that they are associated with progressive damage o the kidney or kidney function. The chronic hyperglycemia of diabetes is associated with long-term damage, dysfunction, ad failure of various organs, especially the eyes, kidneys, nerves, heart and blood vessels. The long-term complications of diabetes include retinopathy with potential loss of vision; nephropathy leading to renal failure, peripheral neuropathy with risk of foot ulcers, amputation and Charcot joins.

In addition, persons with metabolic syndrome are at high risk of progression to the 2 diabetes, and therefore at higher risk than average for diabetic nephropathy. It is therefore desirable to monitor such individuals for microalbuminuria, and to administer a sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some embodiments, the person has metabolic syndrome and blood pressure below 130/85.

Dyslipidemia or disorders or lipid metabolism is another risk factor for heart disease. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. It is believed that high levels of triglycerides are associated with kidney damage. In particular, levels of cholesterol over 200 mg/dL, and especially of 250 mg/dL, would suggest that sEH inhibitors and, optionally, EETs, should be administered. Similarly, triglyceride levels of more than 215 mg/dL, and especially of 250 mg/dL, or higher, would indicate that administration of sEH inhibitors and, optionally, of EETs, would be desirable. The administration of compounds of the present invention with or without the EETs, can reduce the need to administer statin drugs (HMG-CoA reductase inhibitors) to the patients, or reduce the amount of the stains needed. In some embodiments, candidates for the methods, uses and compositions of the invention have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the invention have cholesterol levels over 200 mg/dL and blood pressure below 130/85. In some embodiments, the candidates have cholesterol levels over 225 mg/DL and blood pressure below 130/85.

Methods of Inhibiting the Proliferation of Vascular Smooth Muscle Cells:

In other embodiments, compounds of formula (I) inhibit proliferation of vascular smooth muscle (VSM) cells without significant cell toxicity, (e.g., specific to VSM cells). Because VSM cell proliferation is an integral process in the pathophysiology of atherosclerosis, these compounds are suitable for slowing or inhibiting atherosclerosis. these compounds are useful to subjects at risk for atherosclerosis, such as individuals who have had a heart attack or a test result showing decreased blood circulation to the heart. The conditions of therapeutic administration are as described above.

The methods of the invention are particularly useful for patients who have had percutaneous intervention, such as angioplasty to reopen a narrowed artery, to reduce or to slow the narrowing of the reopened passage by restenosis. In some embodiments, the artery is a coronary artery. The compounds of the invention can be placed on stents in polymeric coatings to provide a controlled localized release to reduce restenosis. Polymer compositions for implantable medical devices, such as stents, and methods for embedding agents in the polymer for controlled release, are known in the art and taught, for example, in U.S. Pat. Nos. 6,335,029; 6,322,847; 6,299,064; 6,290,722; 6,287,285; and 5,637,113. In some embodiments, the coating releases the inhibitor over a period of time, preferably over a period of days, weeks, or months. The particular polymer or other coating chosen is not a critical part of the present invention.

The methods of the invention are useful for slowing or inhibiting the stenosis or restenosis of natural and synthetic vascular grafts. As noted above in connection with stents, desirably, the synthetic vascular graft comprises a material which releases a compound of the invention over time to slow or inhibit VSM proliferation and the consequent stenosis of the graft. Hemodialysis grafts are a particular embodiment.

In addition to these uses, the methods of the invention can be used to slow or to inhibit stenosis or restenosis of blood vessels of persons who have had a heart attack, or whose test results indicate that the are at risk of a heart attack.

In one group of embodiments, compounds of the invention are administered to reduce proliferation of VSM cells in persons who do not have hypertension. In another group of embodiments, compounds of the invention are used to reduce proliferation of VSM cells in persons who are being related for hypertension, but with an agent that is not an sEH inhibitor.

The compounds of the invention can be used to interfere with the proliferation of cells which exhibit inappropriate cell cycle regulation. In one important set of embodiments, the cells are cells of a cancer. The proliferation of such cells can be slowed or inhibited by contacting the cells with a compound of the invention. The determination of whether a particular compound of the invention can slow or inhibit the proliferation of cells of any particular type of cancer an be determined using assays routine in the art.

In addition to the use of the compounds of the invention, the level of EETs can be raised by adding EETs. VSM cells contacted with both an EET and a compound of the invention exhibited slower proliferation than cells exposed to either the EET alone or to the a compound of the invention alone. Accordingly, if desired, the slowing or inhibition of VSM cells of a compound of the invention can be enhanced by adding an EET along with a compound of the invention. In the case of stents or vascular grafts, for example, this can conveniently be accomplished by embedding the EET in a coating along with a compound of the invention so that both are released once the stent or graft is in position.

Method of Inhibiting the Progression of Obstructive Pulmonary Disease, Interstitial Lung Disease, or Asthma:

Chronic obstructive pulmonary disease, or COPD, encompasses two conditions, emphysema and chronic bronchitis, which relate to damage caused to the lung by air pollution, chronic exposure to chemicals, and tobacco smoke. Emphysema as a disease relates to damage to the alveoli of the lung, which results in loss of the separation between alveoli and a consequent reduction in the overall surface area available for gas exchange. Chronic bronchitis relates to irritation of the bronchioles, resulting in excess production of mucin, and the consequent blocking by mucin of the airways leading or the alveoli. While persons with emphysema do not necessarily have chronic bronchitis or vice versa, it is common for persons with one of the conditions to also have the other, as well as other lung disorders.

Some of the damage to the lungs due to COPD, emphysema, chronic bronchitis, and other obstructive lung disorders can be inhibited or reversed by administering inhibitors of the enzyme known as soluble epoxide hydrolase, or "sEH". The effects of sEH inhibitors can be increased by also administering EETs. The effect is at least additive over administering the two agents separately, and may indeed be synergistic.

The studies reported herein show that EETs can be used in conjunction with sEH inhibitors to reduce damage to the lungs by tobacco smoke or, by extension, by occupational or environmental irritants. These findings indicate the the co-administration of sEH inhibitors and of EETs can be used to inhibit or slow the development or progression of COPD, emphysema, chronic bronchitis, or other chronic obstructive lung diseases which cause irritation to the lungs.

Animal models of COPD and humans with COPD have elevated levels of immunomodulatory lymphocytes and neurtrophils. Neutrophils release agents that cause tissue damage and, if not regulated, will over time have a destructive effect. Without wishing to be bound by theory, it is believed that reducing levels of neutrophils reduces tissue damage contributing to obstructive lung diseases such as COPD, emphysema, and chronic bronchitis. Administration of sEH inhibitors to rats in an animal model of COPD results in a reduction in the number of neutrophils found in the lungs. Administration of EETs in addition to the sEH inhibitors also reduced neutrophil levels. The reduction in neutrophil levels in the presence of sEH inhibitor and EETs was greater than in the presence of the sEH inhibitor alone.

While levels of endogenous EETs are expected to rise with the inhibition of sEH activity caused by the action of the sEH inhibitor, and therefore to result in at least some improvement in symptoms or pathology, it may not be sufficient in all cases to inhibit progression of COPD or other pulmonary diseases. This is particularly true where the diseases or other factors have reduced the endogenous concentrations of EETs below those normally present in healthy individuals. Administration of exogenous EETs in conjunction with an sEH inhibitor is therefore expected to augment the effects of the sEH inhibitor in inhibiting or reducing the progression of COPD or other pulmonary diseases.

In addition to inhibiting or reducing the progression of chronic obstructive airway conditions, the invention also provides new ways of reducing the severity or progression of chronic restrictive airway diseases. While obstructive airway diseases tend to result from the destruction of the lung parenchyma, and especially of the alveoli, restrictive diseases tend to arise from the deposition of excess collagen in the parenchyma. These restrictive diseases are commonly referred to as "interstitial lung disease", or "ILDs", and include conditions such as idiopathic pulmonary fibrosis. The methods, compositions and uses of the invention are useful for reducing the severity or progression of ILDs, such as idiopathic pulmonary fibrosis. Macrophages play a significant role in stimulating interstitial cells, particularly fibroblasts, to lay down collagen. Without wishing to be bound by theory, it is believed that neutrophils are involved in activating macrophages, and that the reduction of neutrophil levels found in the studies reported herein demonstrate that the methods and uses of the invention will also be applicable to reducing the severity and progression of ILDs.

In some embodiments, the ILD is idiopathic pulmonary fibrosis. In other embodiments, the ILD is one associated with an occupational or environmental exposure. Exemplars of such ILDs, are asbestosis, silicosis, coal worker's pneumoconiosis, and berylliosis. Further, occupational exposure to any of a number of inorganic dusts and organic dusts is believed to be associated with mucus hypersecretion and respiratory disease, including cement dust, coke oven emissions, mica, rock dusts, cotton dust, and grain dust (for a more complete list of occupational dusts associated with these conditions, see Table 154-1 of Speizer, "Environmental Lung Diseases," Harrison's Principles of Internal Medicine, infra, at pp. 1429-1436). In other embodiments, the ILD is sarcoidusis of the lungs. ILDs can also result from radiation in medical treatment, particularly for breast cancer, and from connective tissue or collagen diseases such as rheumatoid arthritis and systemic sclerosis. It is believed that the methods, used and compositions of the invention can be useful in each of these interstitial lung diseases.

In another set of embodiments, the invention is used to reduce the severity or progression of asthma. Asthma typically results in mucin hypersecretion, resulting in partial airway obstruction. Additionally, irritation of the airway results in the release of mediators which result in airway obstruction. While the lymphocytes and other immunomodulatory cells recruited to the lungs in asthma may differ from those recruited as a result of COPD or an ILD, it is expected that the invention will reduce the influx of immunomodulatory cells, such as neutrophils and eosinophils, and ameliorate the extent of obstruction. Thus, it is expected that the administration of sEH inhibitors, and the administration of sEH inhibitors in combination with EETs, will be useful in reducing airway obstruction due to asthma.

In each of these diseases and conditions, it is believed that at least some of the damage to the lungs is due to agents released by neutrophils which infiltrate into the lungs. The presence of neutrophils in the airways is thus indicative of continuing damage from the disease or condition, wile a reduction in the number of neutrophils is indicative of reduced damage or disease progression. Thus, a reduction in the number of neutrophils in the airways in the presence of an agent is a marker that the agent is reducing damage due to the disease or condition, and is slowing the further development of the disease or condition. The number of neutrophils present in the lungs can be determined by, for example, bronchoalveolar lavage.

Prophylatic and Therapeutic Methods to Reduce Stroke Damage

Inhibitors of soluble epoxide hydrolase ("sEH") and EETs administered in conjunction with inhibitors of sEH have been shown to reduce brain damage from strokes. Based on these results, we expect that inhibitors of sEH taken prior to an ischemic stroke will reduce the area of brain damage and will likely reduce the consequent degree of impairment. the reduced area of damage should also be associated with a faster recovery from the effects of the stroke.

While the pathophysiologies of different subtypes of stroke differ, they all cause brain damage. Hemorrhagic stroke differs from ischemic stroke in that the damage is largely due to compression of tissue as blood builds up in the confined space within the skull after a blood vessel ruptures, whereas in ischemic stroke, the damage is largely due to loss of oxygen supply to tissues downstream of the blockage of a blood vessel by a clot. Ischemic stroked are divided into thrombotic strokes, in which a clot blocks a blood vessel in the brain, and embolic strokes, in which a clot formed elsewhere in the body is carried through the blood stream and blocks a vessel there. But, in both hemorrhagic stroke and ischemic stroke, the damage is due to the death of brain cells. Based on the results observed in our studies, however, we would expect at least some reduction in brain damage in all types of stroke and in all subtypes.

A number of factors are associated with an increased risk of stroke. Given the results of the studies underlying the present invention, sEH inhibitors administered to persons with any one or more of the following conditions or risk factors: high blood pressure, tobacco use, diabetes, carotid artery disease, peripheral artery disease, atrial fibrillation, transient ischemic attacks (TIAs) blood disorders such as high red blood cell counts and sickle cell disease, high blood cholesterol, obesity, alcohol use of more than one drink a day for women or two drinks a day for men, use of cocaine, a family history of stroke, a previous stroke or heart attack, or being elderly, will reduce the area of brain damaged of a stroke. With respect to being elderly, the risk of stroke increases for every 10 years. Thus, as an individual reaches 60, 70, or 80, administration of sEH inhibitors has an increasingly larger potential benefit. As noted in the next section, the administration of EETs in combination with one or more sEH inhibitors can be beneficial in further reducing the brain damage. One can expect beneficial effects from sEHI with or without EETs in a variety of diseases which lead to ischemia reperfusion injury such as heart attacks.

In some uses and methods, the sEH inhibitors and, optionally, EETs, are administered to persons who use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attach and do not have high blood pressure or diabetes, or are 60, 70, or 80 years of age or more and do not have hypertension or diabetes.

Clot dissolving agents, such as tissue plasminogen activator (tPA), have been shown to reduce the extent of damage from ischemic strokes if administered in the hours shortly after a stroke. tPA, for example, is approved by the FDA for use in the first three hours after a stroke. Thus, at least some of the brain damage from a stoke is not instantaneous, but occurs over a period of time or after a period of time has elapsed after the stroke. It is therefore believed that administration of sEH inhibitors, optionally with EETs, can also reduce brain damage if administered within 6 hours after a stroke has occurred, more preferably within 5, 4, 3, or 2 hours after a stroke has occurred, with each successive shorter interval being more preferable. Even more preferably, the inhibitor or inhibitors are administered 2 hours or less or even 1 hour or less after the stroke, to maximize the reduction in brain damage. Persons of skill are well aware of how to make a diagnosis of whether or not a patient has had a stroke. Such determinations are typically made in hospital emergency rooms, following standard differential diagnosis protocols and imaging procedures.

In some uses and methods, the sEH inhibitors and, optionally, EETs, are administered to persons who have had a stroke within the last 6 hours who: use tobacco have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 0, 70, or 80 years of age or more and do not have hypertension or diabetes.

The conditions of therapeutic administration for all of these indications are as described above.

Combination Therapy

As noted above, the compounds of the present invention will, in some instances, be used in combination with other therapeutic agents to bring about a desired effect. Selection of additional agents will, in large part, depend on the desired target therapy (see, e.g., Turner, N. et al. *Prog. Drug Res.* (1998) 51: 33-94; Haffner S. *Diabetes Care* (1998) 21: 160-178; and DeFronzo, R. et al. (eds.) *Diabetes Reviews* (1997) Vol. 5 No. 4). A number of studies have investigated the benefits of combination therapies with oral agents (see, e.g., Mahler, R., *J. Clin. Endocrinol Metab.* (1999) 84: 1165-71: United Kingdom Prospective Diabetes Stud Group UKPDS 28, *Diabetes Care* (1998) 21: 87-92; Bardin, C. W., (ed.), Current Therapy In Endocrinology And Metabolism 6th Edition (Mosby—Year Book, Inc., St. Louis, Mo. 1997); Chiasson, J. et al., *Ann. Intern. Med.* (1994) 121: 928 935; Coniff, R. et al., *Clin. Ther.* (19979) 19: 16-26; Coniff, R., et al., *Am. J. Med.* (1995) 98: 443-451; and Iwanoto, Y. et al., *Diabet. J. Med.* (1006) 13 365-370; Kwiterovich, P. *Am. J. Cardiol* (1998) 82(I2A): 3U-17U). Combination therapy includes administration of a single pharmaceutical dosage formulation which contains a compound having the general structure of formula I and one or more additional active agents, as well as administration of a compound of Formula I and each active agent in its own separate pharmaceutical dosage formulation. For example, a compound of formula I and one or more angiotensin receptor blockers, angiotensin converting enzyme inhibitors, calcium channel blockers, diuretics, alpha blockers, beta blockers, centrally acting agents, vasopeptidase inhibitors, renin inhibitors, endothelin receptor agonists, AGE crosslink breakers, sodium/potassium ATPase inhibitors, endothelin receptor agonists, endothelin receptor antagonists, angiotensin vaccine, and the like; can be administered o the human subject together in a single oral dosage composition, such as a tablet or capsule, or each agent can be administered at essentially the same time (i.e., concurrently), or at separately staggered times (i.e., sequentially). Combination therapy is understood to include all these regimens.

Compounds for Inhibiting Soluble Epoxide Hydrolases:

In addition to the methods provided above, the present invention provides in another aspect, compounds that can inhibit the activity of soluble epoxide hydrolases. In particular, the present invention provides compounds having a formula selected from formula (I) above.

In one embodiment, compounds are those compounds described above as for the recited uses.

In one embodiment, sEH inhibitors for treating hypertension or high blood pressure have an $IC_{50}$ in a defined assay of less than 50 μM. In another embodiment, the compounds have an $IC_{50}$ of 1 μM or less. In another embodiment, the compounds have an $IC_{50}$ of 500 nM or less. In another embodiment, the compounds have an $IC_{50}$ of 150 nM or less. In another embodiment, the compounds have an $IC_{50}$ of 150 nM or less. In another embodiment, the compounds have an $IC_{50}$ of 100 nM or less. In another embodiment, the compounds have an $IC_{50}$ of 50 nM or less. In another embodiment, the compounds have an $IC_{50}$ of 1 nM or less.

Methods of Preparation

The compounds of the present invention can be prepared by a variety of methods as outlined generally in the scheme below. It should be noted that the synthetic conditions illustrated in the following scheme are also applicable to those inhibitors based on 4-aminomethylpiperidine (those with a $CH_2$ spacer).

Scheme 1—Introduction of a Heterocyclic Pharmacophore

Scheme 1 illustrates general methods that can be used for preparation of compounds of the invention having heterocyclic secondary pharmacophore, for example a piperidine. While the scheme is provided for the synthesis of N-(1-benzoylpiperidin-4-yl)-N'-(adamant-1-yl)ureas, pone of skill in the art will understand that a number of commercially available or synthetic heterocyclic amines could be used in place of 4-aminopiperidine, and that other substituents other than benzoyl could also be employed.

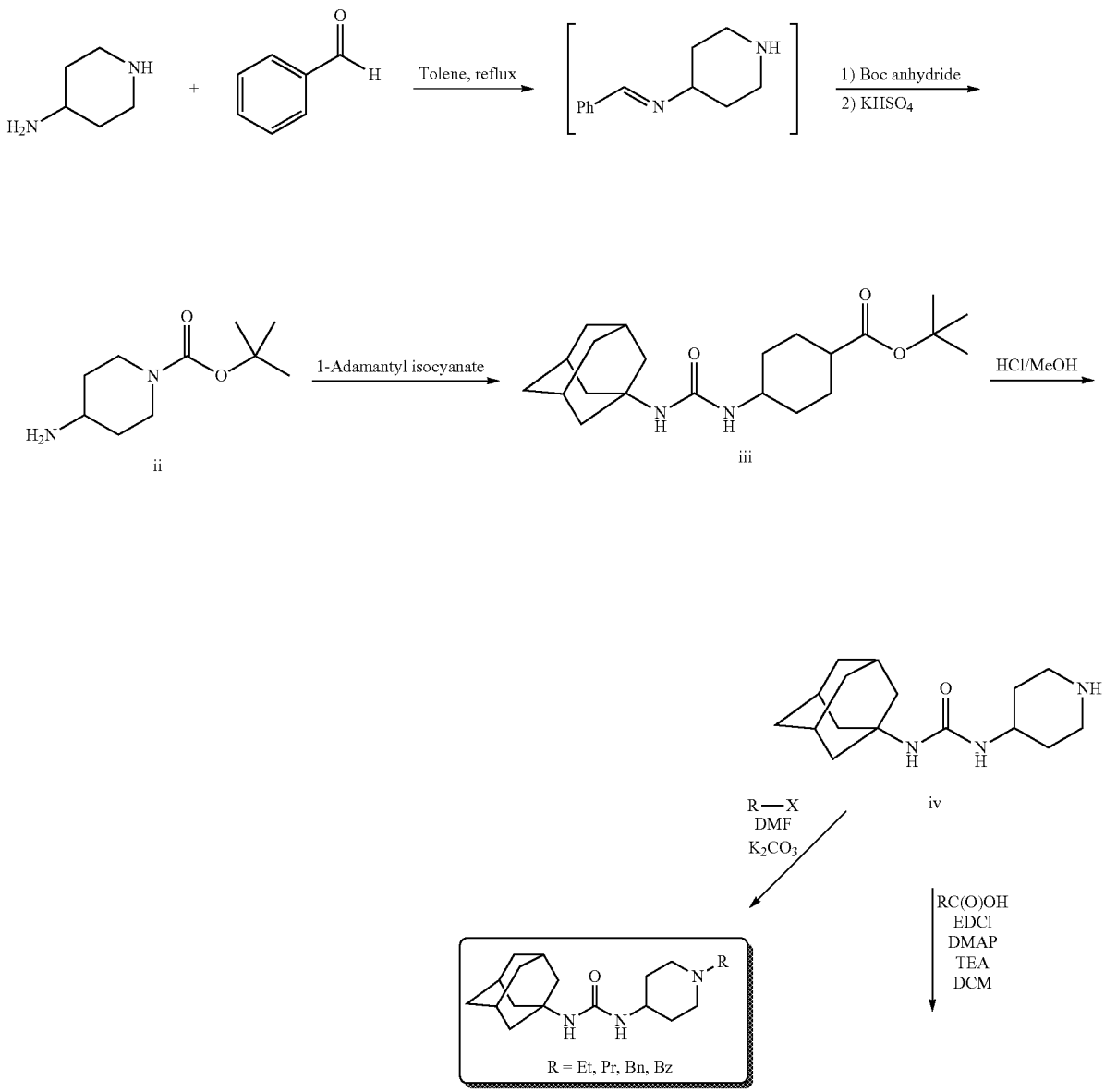

Scheme 1: Synthesis of N-(1-benzoylpiperidin-4-yl)-N'-(adamant-1-yl)ureas.

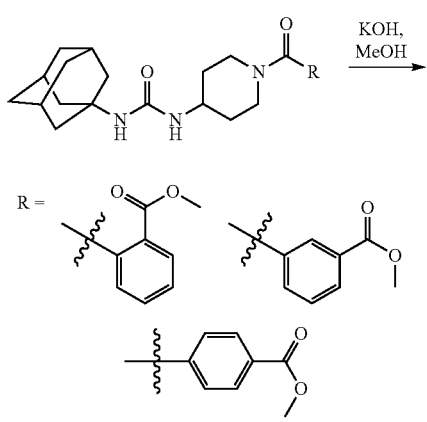
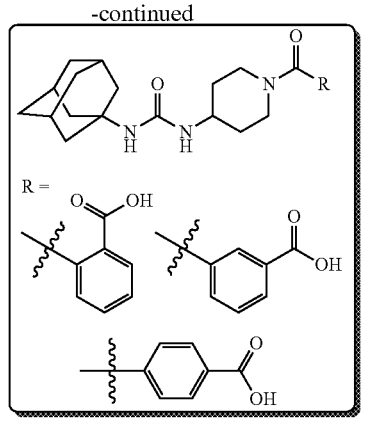

As shown in Scheme 1, 4-aminopiperidine (available from Aldrich Chemical Co., Milwaukee, Wis., USA) is combined with benzaldehyde at room temperature to provide intermediate (i). BOC protection of the piperidine nitrogen provides intermediate carbamate (ii). Reaction of (ii) with a suitable isocyanate provides intermediate (iii). Deprotection of the piperidine (iv) and reaction with a suitable alkylating or acylating agent provides the target compounds. Substitution of adamantyl isocyanate with, for example, a substituted or unsubstituted phenyl isocyanate or cycloalkyl isocyanate (e.g. cyclohexyl isocyanate, also available from Aldrich Chemical Co.) provides other compounds of the invention.

The following examples are provided to illustrate the invention and are not intended to limit any aspect of the invention as set forth above or in the claims below.

EXAMPLES

All melting points were determined with a Thomas-Hoover apparatus (A. H. Thomas Co.) and are uncorrected. Compounds with no melting point values exist in the solid state as either foams or glassy solids. Mass spectra were measured by LC-MS (Waters 2790). $^1$H-NMR spectra were recorded on QE-300 spectrometer, using tetramethylsilane as an internal standard. Signal multiplicities are represented as singlet (s), doublet (d), double doublet (dd), triplet (t), quartet (q), quintet (quint), multiplet (m), broad (br), broad singlet (brs), broad doublet (br d), broad triplet (br t), broad multiplet (br m), doublet of doublet of doublets (ddd) and quartet of doubters (qd). Synthetic methods are described for representative compounds.

The abbreviations used in the examples below have the following meaning: melting point (Mp), mass spectroscopy (MS), thin layer chromatography (TLC), the parent peak in the MS plus H$^4$ ([M+H]$^+$), minute (mm), kilogram (kg), milligram (mg), nanomolar (nM), tetrahydrofuran (THF), tertiary butoxy carbonyl (BOC), potassium sulfate (KHSO$_4$), potassium hydroxide (KOH), magnesium sulfate (MgSO$_4$), hydrogen chloride (HCl), dimethylsulfoxide (DMSO), ethyl (Et), ethyl acetate (EtOAc), methanol (MeOH), dichloromethane (CH$_2$Cl$_2$, DCM), area under the concentration (AUC).

Lower case bolded Roman numerals in the examples below refer to the corresponding intermediates in Scheme 1 above. Compounds numbers are also used as provided in the Schemes as well as in the Tables below.

Example 1

4-Ammopiperidine (2.125 g, 21.2 mmol) was dissolved in toluene (50 mL). To this was added benzaldehyde (2.16 mL, 21.2 mmol). The reaction fitted with a Dean-Stark trap and a condenser and was refluxed for 4 hours under an atmosphere of nitrogen. At this point, when no additional water was seen to form, the reaction was cooled to 0° C. and BOC anhydride (4.63 g, 21.2 mmol) was added via syringe over 10 minutes. The reaction was allowed to warm to room temperature over 1 hr and was stirred for an additional 12 hrs. The solvent was removed in vacuo and the resulting oil was treated with KHSO$_4$(aq) (1 M, 21.2 mL). This was stirred for 1.5 hours. Water (25 mL) was added to the reaction and the aqueous suspension was washed with diethylether (3×100 mL). The water layer was then basified to pH=10 with KOH (s) and was extracted with dichloromethane (3×100 mL). The organic layer was dried over MgSO$_4$ and evaporated to give 4.76 g of a yellow oil. To this oil (1.0 g) was added THF (25 mL). This was stirred for 5 minutes until the oil was completely dissolved. 1-Adamantylisocyanate (0.886 mg, 5.0 mmol, 1 eq) was added and the reaction stirred overnight under an atmosphere of nitrogen. The solvent was removed and the residue was chromatographed on silica with 1:1 ethylacetate:hexanes. The major fraction was collected (TLC rf=0.8 1:1 hexane:EtOAc) and the solvent removed. The resultant residue was treated with a solution of HCl in methanol (35 mL, 4M). This was stirred for 12 hours. The solvent was removed to give the product, after drying at 80° C. under vacuum, as a white powder (1.123 g, 73% yield overall).

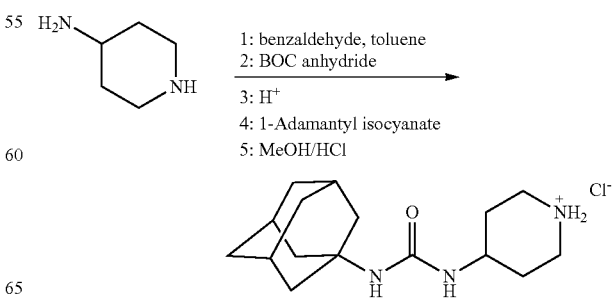

N-piperidin-4-yl)-N'-(adamant-1-yl) urea hydrochloride (iv, 1175)

$^1$H (300 MHz, DMSO d6): 8.96 (br 2H), 6.22 (br, 6H, urea NH+H$_2$O), 3.61-3.52 (m, 1H), 3.24-3.10 (m, 2H), 2.95-2.80 (m, 2H), 2.10-1.70 (br m, 11H), 1.70-1.40 (br m, 8H).

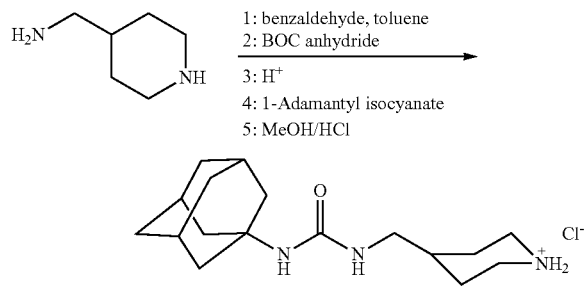

N-((piperidin-4-yl)methyl)-N'-(adamant-1-yl)urea hydrochloride (1118)

This was run as per above with a yield of 95%. Mp. (free base): 199-201° C. dec. $^1$H NMR (300 MHz, DMSO): 8.79 (br, 1H), 8.50 (br, 1H), 6.00 (br, 1H), 5.80 (br, 1H), 3.20 (br d, J=12.3 Hz, 2H), 2.80-2.70 (br m, 3H), 2.00-1.40 (br m, 19H), 1.30-1.15 (br m, 2H).

Example 2

General procedure for the alkylation of piperidinyl ureas: N-(1-ethylpiperidin-4-yl)-N'-(adamant-1-yl) urea (R=Et, 1152)

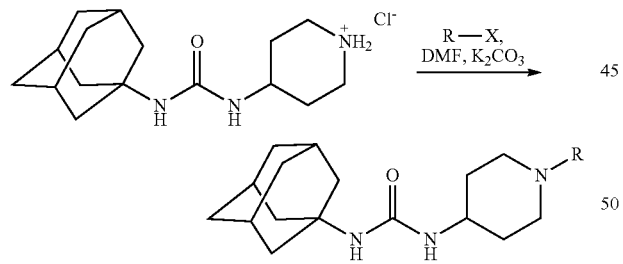

The appropriate piperdinyl urea (0.319 mmol) was combined with the appropriate alkyl or benzyl bromide (X=Br) (0.382 mmol) and K$_2$CO$_3$ (132 mg, 0.96 mmol) in DMF (3.0 mL). The reaction was heated at 50° C. for 12 hours. At this point, the reaction was cooled to room temperature and the solvent was removed in vacuo. The residue was partitioned between DCM and aqueous NaHCO$_3$ (satd) and the organic layer removed and dried with Na$_2$SO$_4$. The solvent was evaporated and the residue chromatographed on silica gel using ammonia saturated methanol/DCM as the eluent (5:100). Yield=42%. Mp.: 203-213° C. dec. $^1$H NMR (300 MHz, CDCl$_3$): 4.15-4.05 (br, 2H), 3.63-3.47 (m, 1H), 2.91-2.81 (br m, 2H), 2.39 (q, J=7.18 Hz, 2H), 2.13-1.88 (br m, 13H), 1.66 (br, 6H), 1.40 (qd, J=8.3, 3.3 Hz, 2H), 1.07 (t J=7.19 Hz, 3H).

Example 3

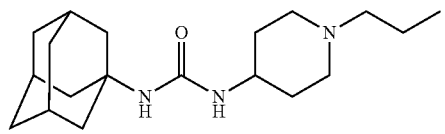 [SMILES: CCCN1CCC(NC(=O)NC23CC4CC(CC(C4)C2)C3)CC1]

N-(1-n-propylpiperidin-4-yl)-N'-(adamant-1-yl) urea (1155)

Yield=60%. Mp.: 195-200° C. dec. $^1$H (300 MHz, CDCl$_3$): 4.10-4.00 (br, 2H), 3.60-3.45 (m, 1H), 2.90-2.78 (m, 2H), 2.23-2.22 (m, 2H), 2.10-1.70 (m, 13H), 1.70-1.57 (br. 6), 1.56-1.30 (m, 4H), 0.88 (t, J=7.4 Hz, 3H).

Example 4

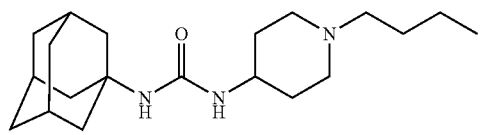 [SMILES: CCCCN1CCC(NC(=O)NC23CC4CC(CC(C4)C2)C3)CC1]

N-(1-n-propylpiperidin-4-yl)-N'-(adamant-1-yl) urea (1160)

Yield=53%. Mp.: 195-200° C. dec. $^1$H (300 MHz, CDCl$_3$): 4.0-3.95 br, 2H), 3.51-3.45 (m, 1H), 2.90-2.80 (m, 2H), 2.35-2.25 (m, 2H), 2.10-1.60 (br m, 19H), 1.50-1.25 (m, 6H), 0.89 (t, J=7.2 Hz, 3H).

Example 5

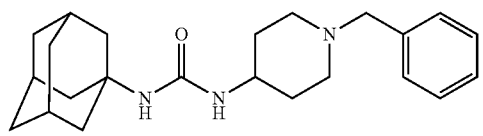 [SMILES: O=C(NC1CCN(Cc2ccccc2)CC1)NC12CC3CC(CC(C3)C1)C2]

N-(1-benzylpiperidin-4-yl)-N'-(adamant-1-yl) urea (1158)

Yield=46%. Mp.: 170-173° C. $^1$H (300 MHz, CDCl$_3$), 7.35-7.20 (m, 5H), 4.00-3.94 (br, 2H), 3.58-3.45 (m, 1H), 3.43 (s, 2), 2.80-2.72 (m, 2H), 2.10-1.60 (br m, 19H), 1.35 (qd. J=7.9, 3.3 Hz, 2H).

Example 6

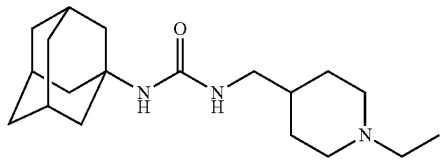 [SMILES: CCN1CCC(CNC(=O)NC23CC4CC(CC(C4)C2)C3)CC1]

N-((1-ethylpiperidin-4-yl)-N'-(adamant-1-yl)urea (1154)

Yield=50%. Mp.: 143-151° C. dec. $^1$H (300 MHz, CDCl$_2$): 4.28 (t, J=5.4 Hz, 1H), 4.09 (br, 1H), 3.05 (t, J=6.2 Hz. 2H), 2.98-2.89 (br m, 2H), 2.38 (q, J=7.4 Hz. 2H), 2.10-1.60 (br m. 19H), 1.52-1.40 (br m, 1H), 1.27 (qd, J=12.4, 3.7 Hz, 2H), 1.08 (t, J=7.2 Hz, 3H).

Example 7

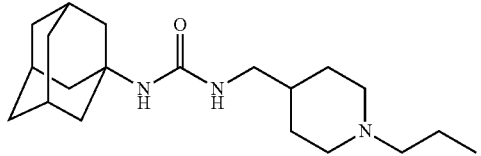 [SMILES: CCCN1CCC(CNC(=O)NC23CC4CC(CC(C4)C2)C3)CC1]

N-(1-n-propylpiperidin-4-yl)-N'-(adamant-1-yl)urea (1122)

Yield=40%. 1 (300 MHZ, CDCl$_3$): 4.69 (t, J=5.8 Hz, 1H), 4.38 (br, 1), 3.08-2.94 (m, 4H), 2.42-2.32 (m, 2H), 2.10-1.55 (br m, 22H), 1.36 (qd. J=11.8, 3.3 Hz, 2H).

Example 8

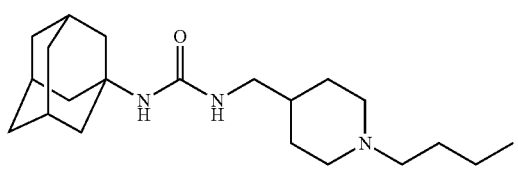 [SMILES: CCCCN1CCC(CNC(=O)NC23CC4CC(CC(C4)C2)C3)CC1]

N-(1-n-propylpiperidin-4-yl)-N'-(adamant-1-yl)urea (1155)

Yield=43%. $^1$H (300 MHz, CDCl$_3$): 4.30 (br. 1H), 4.12 (br, 1H), 3.05 (t, J=6.2 Hz, 2H), 2.98-2.88 (m, 2H), 2.34-2.26 (m, 2H), 2.10-1.2 (br m, 26H), 0.09 (t, J=7.2 Hz, 3H).

Example 9

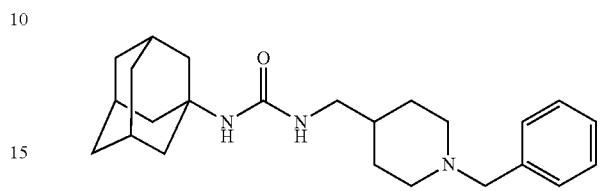

N-(1-benzylpiperidin-4-yl)-N'-(adamant-1-yl)urea (1119)

Yield=48%. Mp.: 162-167° C. $^1$H (300 CDCl$_3$): 7.35-7.20 (m, 5H), 4.37 (br t, J=5.8 Hz, 1H), 4.17 (br, 1H), 3.48 (s, 2H) (t=6.2 Hz, 2H), 2.95-2.80 (br m, 2H), 2.10-1.40 (br m, 20H), 1.27 (qd, J=11.9, 3.5 Hz, 2H).

Example 10A

General Procedure for the Acylation of Piperidines

N-(1-acetylpiperidin-4-yl)-N'-(adamant-1-yl) urea (1153)

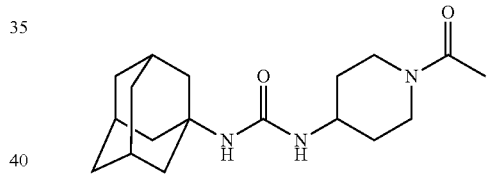

The desired piperidinyl urea (6.6 mmol) and an appropriate carboxylic acid (or ester-acid) (7.92 mmol), DMAP (0.85 g, 6.6 mmol) and TEA (5.0 mL, 36 mmol) were all combined in dichloromethane at 0° C. The reaction was allowed to stir for 10 minutes. At this point, EDCI (1.38 g, 7.26 mmol) was added and the reaction was allowed to warm to n over 2 hours. After reaching room temperature, the reaction was allowed to stir for 18 hrs. The reaction was then washed with K$_2$CO$_{3(aq)}$ (1M, 3×50 mL) followed by HCl$_{(aq)}$ (1M, 3×50 mL). The organic layer was dried and evaporated to five a yellow oil. Recrystallization from acetone or chromatograph (SiO$_2$) with 5% MeOH/DCM afforded the product. Yield=75%. Mp.: 205-206° C. $^1$H (300 MHz, CDCl$_3$): 4.67 (br d, J=5.9 Hz, 1H), 4.57 (br s, 1H), 4.44 (br d, J=13.1 Hz, 1H), 3.90-3.65 (m, 2H), 2.13 (br t, J=13.1 Hz, 1H), 2.74 (br t, J=13.2 Hz, 1H), 2.20-1.50 (br m, 20H), 1.30-1.10 (m, 2H).

Example 10B

Alternative Synthesis of N-(1-Acetylpiperidin-4-yl)-'-(adamant-1-yl) urea (1153)

Preparation of N-Acetyl piperid-4-yl amide

A reactor was charged with 1.00 mole-equivalent of 4-piperidinecarboxamide, 15.9 mole-equivalents of THF, and 1.23 mole-equivalents of N,N-(diisopropyl)ethylamine under a nitrogen atmosphere. The resulting mixture was cooled to 20° C. internal, and 1.10 mole-equivalents of acetic anhydride was added at such a rate as to maintain an internal temperature of less than 30° C. After addition was complete, the reaction mixture was stirred while maintaining an internal temperature of 20° C. The reaction contents was monitored until the amount of unreacted 4-piperidinecarboxamide was less than 1% relative to N-acetyl piperid-4-yl amide product (typically about 4-10 hours). The precipitated product was collected by filtration and washed with THF to remove excess (diisopropyl)ethylamine hydrochloride. The solid product was dried to constant weight in a vacuum oven under a nitrogen bleed white maintaining an internal temperature of ≤50° C. to afford the product as a white solid in 94% yield; Mp.: 172-174° C. $^1$H NMR(CD$_3$OD) δ: 4.48-4.58 (bd, 1H), 3.92-4.01 (bd, 1H), 3.08-3.22 (m, 1), 2.62-2.74 (m, 1H), 2.44-2.53 (m, 1H), 2.12 (s, 2H), 1.88-19.3 (m, 2H), 1.45-1.72 (m, 2H); MS: 171 [M+H]$^+$.

Preparation of N-(1-Acetylpiperidin-4-yl)-N'-(adamant-1-yl) urea

A reactor was charged with 100 mole-equivalents of N-acetyl piperid-4-yl amide, 0.87 mole-equivalents of 1-adamantyl amine, and 49.7 mole-equivalent of acetonitrile, and the resulting mixture was heated to 75° C. internal under a nitrogen atmosphere. (Diacetoxyiodo)benzene was added, the reaction mixture was cooled to 25° C. internal, and approximately 24 mole-equivalents of solvent was distilled out under vacuum while maintaining internal temperature below 40° C. The reaction mixture was cooled with agitation to 0-5° C. internal and stirred for an additional 2 hours. The technical product was collected by filtration and washed with acetonitrile. The crude product was dried to constant weight in a vacuum oven under a nitrogen bleed maintaining an internal temperature of ≤50° C. The dried, crude product was slurried with water maintaining an internal temperature of 20±5° C. internal for 4 hours and then collected by filtration. The filter cake was washed with heptane under a nitrogen atmosphere then dried to constant weight in a vacuum oven under a nitrogen bleed maintaining an internal temperature of ≤70° C. to afford product as a white solid in 72% yield based on 1-adamantyl amine. $^1$H NMR(DMSO-d$_6$) δ: 5.65-5.70 (bd, 1H), 5.41 (s, 1H), 4.02-4.10 (m, 1H), 3.61-5.70, (m, 1H), 3.46-3.58 (m, 1H), 3.04-3.23 (m, 1H), 2.70-2.78 (m, 1H), 1.98 (s, 3H), 1.84 (s, 6H), 1.64-1.82 (m, 2H), 1.59 (s, 6H), 1.13-1.25 (m, 1H), 1.00-1.12 (m, 1H); MS: 320 [M+H]$^+$; m.p. 202-204° C.

Example 11

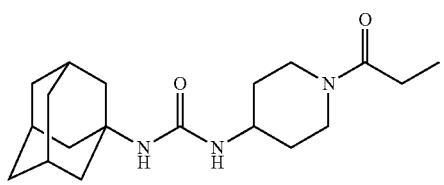 [SMILES: CCC(=O)N1CCC(NC(=O)NC23CC4CC(CC(C4)C2)C3)CC1]

N-(1-propionylpiperidin-4-yl)-N'-yl)urea (1163)

Made by treating 1 eq of the piperidine with 1 eq of propanoyl chloride in pyridine ([starting material]=0.10 M) at 0° C. for 12 hrs. After removal of the solvent, the product was chromatographed on silica gel with 90:1 DCM:MeOH/NH$_3$ to give to target in 20% yield. Mp.: 211-224° C. dec. $^1$H (300 MHz, CDCl$_3$): 4.52 (br d, J=12.6 Hz, 1), 4.40-4.00 (br, 2H), 3.90-3.70 (m, 2H), 3.10 (br t, J=12.4 Hz., 1H), 2.75 (br t, J=12.5 Hz, 1H), 2.34 (q, J=7.4 Hz, 2H), 2.10-1.60 (br m, 17H), 1.30-1.15 (m, 2H), 1.13 (t, J=7.3 Hz, 3H).

Example 12

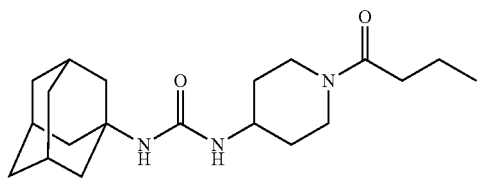 [SMILES: CCCC(=O)N1CCC(NC(=O)NC23CC4CC(CC(C4)C2)C3)CC1]

N-(1-butyrylpiperidin-4-yl)-'-(adamant-1-yl)urea (1157)

Synthesized as per: 1163. Yield: 71%. Mp.: 148-188° C. dec. $^1$H NMR (300 MHz, CDCl$_3$): 4.52. (br d, J=13.3, 1H), 4.25-410 (br, 2H), 3.85-3.65 (br, 2H), 3.10 (br t, J=5 Hz, 1H), 2.75 (br t J=11.3 Hz, 1H), 2.35-2.23 (m, 2H), 2.10-1.60 (br m, 19H), 1.30-1.15 (m, 2H), 0.96 (t, J=7.4 Hz, 3H).

Example 13

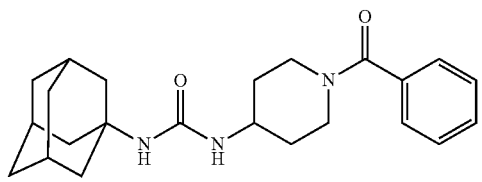

N-(1-benzoylpiperidin-4-yl)-N'-(adamant-1-yl)urea (1159)

Yield=63% (via acyl chloride). $^1$H (300 MHz, CDCl$_3$): 7.44-7.32 (m, 5H), 5.00-4.50 (br m, 3H), 3.90-3.78 (br, 1H), 3.76-3.60 (br, 1H), 3.20-2.90 (br, 2H), 2.10-160 (br m, 17H), 1.50-1.20 (br m, 2H).

Example 14

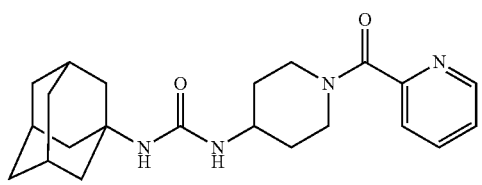 [SMILES: O=C(NC1CCN(C(=O)c2ccccn2)CC1)NC12CC3CC(CC(C3)C1)C2]

N-(1-(Pyridine-2-carbonyl)piperidin-4-yl)-N'-(adamant-1-yl)urea (1201)

Yield=70% via EDCI coupling (see 1152). $^1$H (300 MHz, CDCl$_3$): 8.59 (br d, J=5.0 Hz, 1H), 7.80 (bd, J=7.7, 1.7 Hz, 1H), 7.56 (br d, J=7.6 Hz, 1H), 7.35 (ddd, J=7.6, 4.8, 1.2 Hz, 1H), 4.70-4.50 (br m, 3H), 3.90-3.70 (m, 2H), 3.15 (br t, J=12.5 Hz, 1H), 2.95 (br t, J=12.3 Hz, 1), 2.10-1.60 (br m, 17H), 1.50-1.20 (br m, 2H).

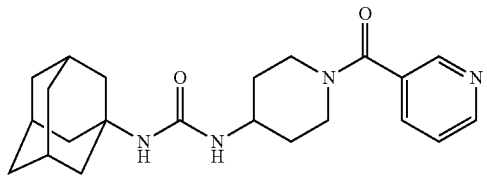 [SMILES: O=C(NC1CCN(C(=O)c2cccnc2)CC1)NC12CC3CC(CC(C3)C1)C2]

N-(1-Pyridine-3-carbonyl)piperidin-4-yl)-N'-yl)(adamant-1-yl)urea (1434)

Yield 86% via EDCI coupling, $^1$H (300 MHz, CDCl$_3$): 8.67 (br d, J=5.0 Hz, 1H), 8.65 (br, 1H), 7.74 (br d, J=8.0 Hz, 1H), 7.38 (dd, J=7.9, 5.0 Hz, 1H), 4.67-4.23 (br m, 3H), 3.94-3.70 (m, 1H), 3.70-3.55 (br, 1H), 3.20-2.90 (br m, 2H), 2.10-1.60 (br m, 17H), 1.50-1.20 (br m, 2H).

Example 15

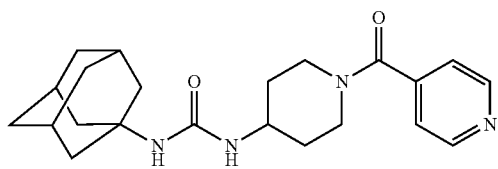 [SMILES: O=C(NC1CCN(C(=O)c2ccncc2)CC1)NC12CC3CC(CC(C3)C1)C2]

N-(1-pyridine-4-carbonyl)piperidin-4-yl)-N'-(adamant-1-yl)urea (1433)

Yield=81% via EDCI coupling. Mp 197-199° C. $^1$H (300 MHz, CDCl$_3$): 8.70 (m, 2H), 7.26 (m, 2H), 4.60 (br d, J=14.2 Hz, 1H), 4.40 (d, J=1.6 Hz, 1H), 4.31 (s, 1H), 3.90-3.70 (m, 1H), 3.57 (br d, J=14.0 Hz, 1H), 3.13 (br t, J=12.3 Hz, 1H), 2.95 (br t, J=12.0 Hz, 1H), 2.10-1.60 (br m, 17H), 1.37 (m, 1H), 1.21 (m, 1H).

Example 16

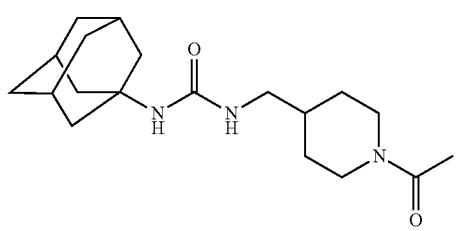 [SMILES: CC(=O)N1CCC(CNC(=O)NC23CC4CC(CC(C4)C2)C3)CC1]

N-((1-acetylpiperidin-4-yl)-methyl)-N'-(adamant-1-yl)urea (1156)

Yield=55%. $^1$H (300 MHz, CDCl$_3$) 5.10-4.50 (br, 2H), 4.60 (d, J=13.3 Hz. 1H), 3.81 (d, J=13.4 Hz, 1H), 3.15 (br dd, J=13.7, 4.4 Hz, 1H), 3.03 (br t, J=12.6 Hz, 1H), 2.92 (br dd, J=13.0, 4.5 Hz, 1H), 2.53 (br t, J=12.9 Hz, 1H), 2.4-1.4 (br m, 21H), 1.20-0.99 (m, 2H).

Example 17

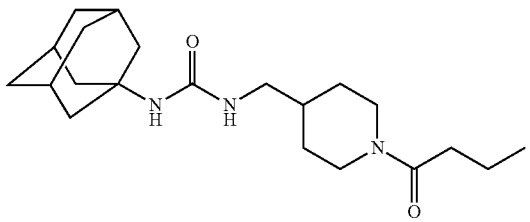 [SMILES: CCCC(=O)N1CCC(CNC(=O)NC23CC4CC(CC(C4)C2)C3)CC1]

N-(1-propanoylpiperidin-4-yl)(methyl)-N'-(adamant-1-yl)urea (1162)

Yield=20% (via acid chloride). $^1$H (300 MHz, CDCl$_3$): 4.60 (br d, J=12.0 Hz, 1H), 3.85 (br d, J=12.3 Hz, 1H, 3.20-2.80 (br, 3H), 2.52 (br t, J=12.8 Hz. 1H), 2.33 (q, J=7.5 Hz, 2H), 2.3-1.4 (br m, 18H), 1.13 (t, J=7.5 Hz, 3H), 1.15-1.05 (br m, 2H). (note, sample contained water, therefore no urea N—H are seen).

Example 18

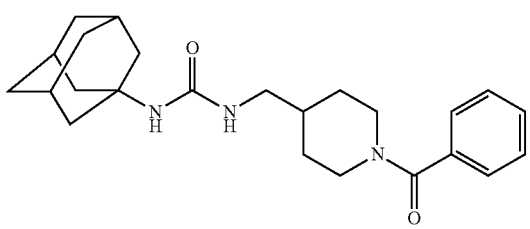 [SMILES: O=C(NCC1CCN(C(=O)c2ccccc2)CC1)NC12CC3CC(CC(C3)C1)C2]

N-((1-butyrylpiperidin-4-yl)methyl)-N'(adamant-1-yl)urea (1120)

Yield=35%. Mp.: 117-149° C. dec. $^1$H (300 MHz, CDCl$_3$): 4.78 (br t, J=4.7 Hz, 1H), 4.61 (br d, J=13.1 Hz, 1H), 4.47 (s, 1H), 3.86 (br d, J=13.6 Hz, 1H), 3.20-3.08 (m, 1H), 2.98 (t, J=13.1 Hz, 3H), 2.95-2.84 (m, 1H), 2.52 (t, J=12.6 Hz, 1H), 2.29 (t, J=7.4 Hz, 2H), 2.10-1.50 (m, 20H), 1.20-100 (m, 2H), 0.96 (t, J=7.4 Hz, 3H).

Example 19

N-((1-benzoylpiperidin-4-yl)methyl)-N'-yl)(adamant-1-yl)urea (1121)

Yield=45%, ¹H (300 MHz, CDCl₃): 7.45-7.34 (m, 5H), 4.80-4.60 (br, 1H), 4.50-4.40 (br, 1H), 4.30-4.05 (br, 1H), 3.90-3.60 (br, 1H), 3.20-2.60 (br, 4H), 2.10-1.5 (br m, 18H), 1.30-1.0 (br, 2H).

Example 20

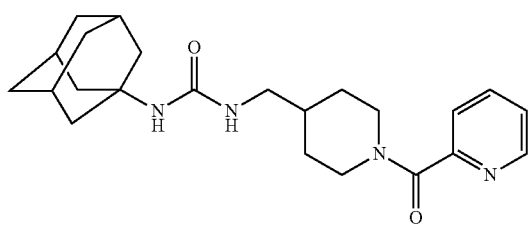 [SMILES: O=C(NCC1CCN(C(=O)c2ccccn2)CC1)NC12CC3CC(CC(C3)C1)C2]

N-((1-(pyridine-2-carbonyl)piperidin-4-yl)methyl-N'-(adamant-1-yl)urea (1207)

Yield=73%, ¹H (300 MHz, CDCl₃): 8.59 (br d, J=5.0 Hz, 1H), 7.79 (td, J=7.7, 1.7 Hz, 1H), 7.56 (br d, J=7.7 Hz, 1H), 7.33 (ddd, J=7.6, 4.8, 1.2 Hz, 1H), 3.20-2.90 (m, 3H), 2.77 (br t, J=12.6 Hz, 1H), 2.10-1.50 (m, 18H), 1.15-1.05 (m, 2H).

Example 21

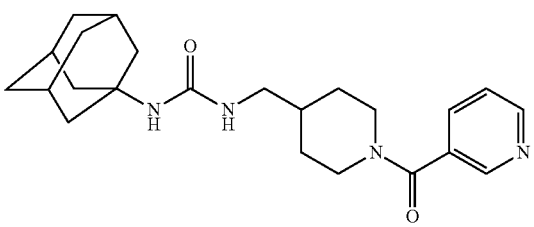 [SMILES: O=C(NCC1CCN(C(=O)c2cccnc2)CC1)NC12CC3CC(CC(C3)C1)C2]

N-((1-pyridine-3carbonyl)piperidin-4-yl)methyl)-N'-(adamant-1-yl)urea (1436)

Yield=quantitative. ¹H (300 MHz, CDCl₃): 8.65 (dd, J=4.9, 1.6 Hz, 1H), 8.64 (d, J=2.0 Hz, 1H), 7.74 (dt, 7.8, 1.9 Hz, 1H), 7.37 (dd, J=7.9, 4.9 Hz, 1H), 5.00-4.90 (br, 1H), 4.78-4.60 (br, 1H), 4.60-4.44 (br 1H), 3.79-3.62 (br, 1H), 3.21-2.68 (br m, 4H), 2.10-1.50 (m, 18H), 1.15-1.05 (m, 2H).

Example 22

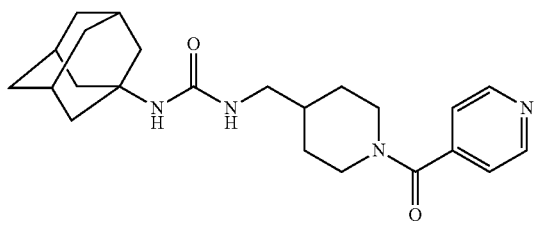 [SMILES: O=C(NCC1CCN(C(=O)c2ccncc2)CC1)NC12CC3CC(CC(C3)C1)C2]

N-((1-(pyridine-4-carbonyl)piperidin-4-yl)methyl)-N'-(adamant-1-yl)urea (1435)

Yield=77%. 8.70-8.66 (m, 2H), 7.28-7.25 (m, 2H), 4.77-4.58 (br, 2H), 4.44-4.36 (br, 1H), 3.60 (br d, J=13.5 Hz, 1H), 3.20-2.95 (m, 3H), 2.77 (br t, J=12.5 Hz, 1H), 2.10-1.50 (m, 18H), 1.15-1.05 (m, 2H).

Example 23

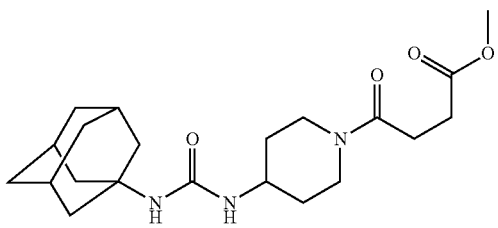 [SMILES: COC(=O)CCC(=O)N1CCC(NC(=O)NC23CC4CC(CC(C4)C2)C3)CC1]

4-[4-(3-Adamantan-1-yl-ureido)-piperidin-1-yl]-4-oxo-butanoic acid methyl ester (1205)

Yield=78%. Mp 169-175° C. dec. ¹H (300 MHz, CDCl₃): 4.65-4.34 (br m, 3H), 3.90-3.67 (br m, 2H), 3.69 (s, 3H), 3.12 (br t, J=13.2 Hz, 1H), 2.76 (br t, J=13.2 Hz, 1H), 2.71-2.54 (m, 4H), 2.20-1.5 (m, 17H), 1.30-1.10 (m, 2H).

Example 24

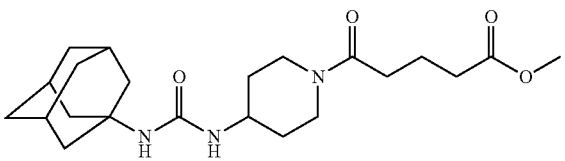 [SMILES: COC(=O)CCCC(=O)N1CCC(NC(=O)NC23CC4CC(CC(C4)C2)C3)CC1]

5-[4-(3-Adamantan-1-yl-ureido)-piperidin-1-yl]-5-oxo-pentanoic acid methyl ester (1206)

Yield=6.1%. Mp 152-154° C. ¹H (300 MHz, CDCl₃): 4.65-4.34 (br m, 3H), 3.90-3.67 (br m, 2H), 3.66 (s, 3H), 3.09 (br t, J=1.37 Hz, 1H), 2.70 (br, J=13.7 Hz, 1H), 2.45-2.31 (m, 4H) 2.20-1.5 (m, 19H), 1.30-1.10 (m, 2H).

Example 25

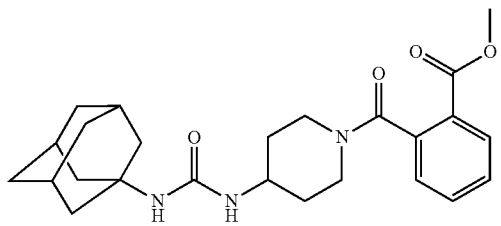 [SMILES: COC(=O)c1ccccc1C(=O)N1CCC(NC(=O)NC23CC4CC(CC(C4)C2)C3)CC1]

2-[4-(3-Adamantan-1-yl-ureido)-piperidine-1-carbonyl]-benzoic acid methyl ester (1202)

Yield=63%. $^1$H (300 MHz, CDCl$_3$): 8.03 (d, J=7.9 Hz, 1H), 7.58 (t, J=7.7 Hz, 1H), 7.46 (t, J=7.7 Hz, 1H), 7.25 (d, J=7.7 Hz, 1H), 5.00-4.62 (br, 2H), 4.55 (br d. J=13.0 Hz, 1H), 3.87 (s, 3H), 3.85-3.72 (br m, 1H), 3.13 (br d, J=13.1 Hz, 1H), 3.11-2.94 (m, 2H), 2.10-1.10 (m, 19H).

Example 26

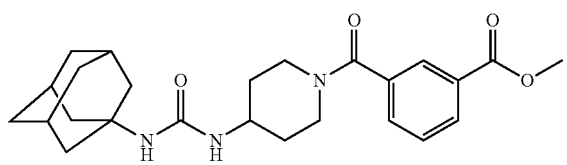 [SMILES: COC(=O)c1cccc(C(=O)N2CCC(NC(=O)NC34CC5CC(CC(C5)C3)C4)CC2)c1]

3-[4-(3-Adamantan-1-yl-ureido)-piperidine-1-carbonyl]-benzoic acid methyl ester (1203)

Yield=61%. $^1$H (300 MHz, CDCl$_3$): 8.10 (dd, J=7.6, 1.4 Hz, 1H), 8.04 (d, J=1.4 Hz, 1H), 7.58 (dd. J=7.6, 1.4 Hz, 1H), 7.50 (t, J=7.6 Ha. 1H), 4.7-4.4 (br, 3H), 3.93 (s, 3H), 3.90-3.81 (br, 1H), 3.70-3.55 (br, 1H), 3.20-3.90 (br m, 2H), 2.15-1.60 (br m, 17H), 1.50-1.10 (br m, 2H).

Example 27

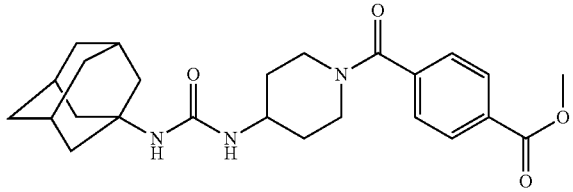 [SMILES: COC(=O)c1ccc(C(=O)N2CCC(NC(=O)NC34CC5CC(CC(C5)C3)C4)CC2)cc1]

4[4-(3-Adamantan-1-yl-ureido)-piperidine-1-carbonyl]-benzoic acid methyl ester (1204)

Yield=70%. Mp 239-243° C. $^1$H (300 MHz, CDCl$_3$): 8.08 (d, J=8.5 Hz, 2H), 7.43 (d, J=8.5 Hz, 2H), 4.67-4.50 (br m, 2H), 4.45 (br, 1H), 3.94 (s, 3H), 3.90-8.74 (m, 1H), 3.65-3.55 (br m, 1H), 3.20-3.99 (br m, 2H), 2.15-1.60 (br m, 17H), 1.50-1.10 (br m, 2H).

Example 28

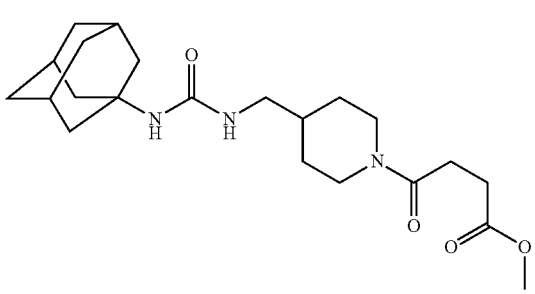 [SMILES: COC(=O)CCC(=O)N1CCC(CNC(=O)NC23CC4CC(CC(C4)C2)C3)CC1]

4-{[(3-Adamantan-1-yl-ureido)-methyl]-piperidin-1-yl}-4-oxo-butanoic acid methyl ester (1209)

Yield=72%. $^1$H (300 MHz, CDCl$_3$): 4.70-4.10 (br, 2H), 4.58 (d, J=12.4 Hz, 1H), 3.89 (d, J=12.5 Hz, 1H, 1H), 3.69 (s, 3H), 3.15 (br dd, J=13.7, 4.4 Hz, 1H), 3.03 (br t. J=12.6 Hz, 1H), 2.92 (br dd, J=13.0, 4.5 Hz, 1H), 2.64 (s, 4H), 2.53 (br t, J=12.9 Hz, 1H), 2.10-1.50 (br m, 18H), 1.15-1.00 (m, 2H).

Example 29

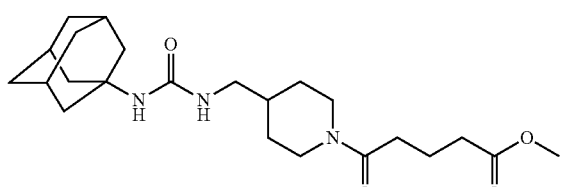

5-[4-[(3-Adamantan-1-yl-ureido)-methyl]-piperidin-1-yl]-5-oxo-pentanoic acid methyl ester (1212)

Yield=42%. $^1$H (300 MHz, CDCl$_3$): 4.70-4.10 (br m, 2H), 4.58 (d, J=12.4 Hz. 1H), 3.89 (d, J=12.5 Hz, 1H), 3.66 (s, 2H), 3.15 (br dd, J=13.7, 4.4 Hz, 1H), 3.03 (br t, J=12.6 Hz, 1H), 2.92 (br dd, J=13.0, 4.5 Hz, 1H),), 2.53 (br t, J=12.9 Hz, 1H), 2.39 (m, 4H), 2.10-1.50 (br m, 20H), 1.20-0.95 (m, 2H).

Example 30

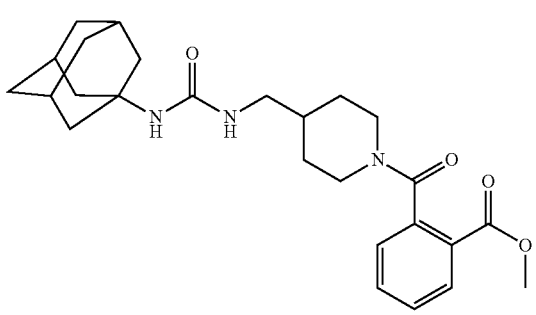 [SMILES: COC(=O)c1ccccc1C(=O)N1CCC(CNC(=O)NC23CC4CC(CC(C4)C2)C3)CC1]

2-{4-[(3-Adamantan-1-yl-ureido)-methyl]-piperidine-1-carbonyl}-benzoic acid methyl ester 1210)

Yield=76%. $^1$H (300 MHz, CDCl$_3$): 8.02 (d, J=7.8 Hz, 1), 7.57 (td, J=7.5, 1.2 Hz, 1H), 7.45 (td, J=7.6, 1.2 Hz, 1H), 7.26 (d, J=7.6 Hz, 1H), 5.10-4.85 (br m, 1H), 4.74 (br d, J=12.5 Hz, 1H), 4.70-4.60 (br, 1H), 3.87 (s, 3H), 3.35 (br d, J=12.5 Hz, 1H), 3.20-3.10 (m, 1H), 3.00-2.70 (m, 3H),), 2.10-1.50 (br m, 18H), 1.20-0.95 (m, 2H).

Example 31

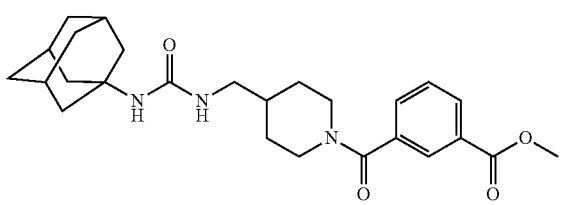 [SMILES: COC(=O)c1cccc(C(=O)N2CCC(CNC(=O)NC34CC5CC(CC(C5)C3)C4)CC2)c1]

3-{4-[(3-Adamantan-1-yl-ureido)-methyl]-piperidine-1-carbonyl}-benzoic acid methyl ester (1209)

Yield=67%. $^1$H (300 MHz, CDCl$_3$): 8.08 (d, J=7.7 Hz, 1H), 8.04 (s, 1H), 8.04 (s, 1H), 7.58 (d, J=7.7 Hz, 1H), 7.49 (t, J=7.6 Hz, 1H), 5.10-4.40 (br m, 3H), 3.93 (s, 3H) 3.75-3.63 (br, 1H), 3.20-2.80 (br m, 4H), 2.10-1.50 (br m, 18H), 1.20-0.95 (m, 2H).

Example 32

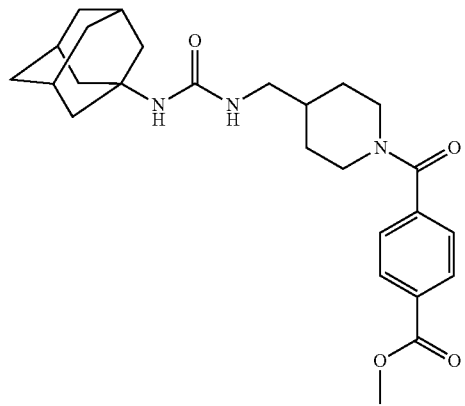 [SMILES: COC(=O)c1ccc(C(=O)N2CCC(CNC(=O)NC34CC5CC(CC(C5)C3)C4)CC2)cc1]

4-{4-[(3-Adamantan-1-yl-ureido)-methyl]-piperidine-1-carbonyl}-benzoic acid methyl ester (1211)

Yield=71%. $^1$H NMR (300 MHz, CDCl$_3$): 8.07 (d, J=8.5, 2H), 7.44 (d. J=8.5, 2H), 4.70 (br d, K=12.1 Hz, 1H), 4.55-4.45 (br, 1H), 4.22 (br, 1H), 3.94 (s, 3H), 3.64 (br d, j=12.4 Hz, 1H), 3.25-2.70 (br m, 4H), 2.10-1.50 (br m, 18H), 1.20-0.95 (m, 2H).

General Procedure for the Hydrolysis of Methyl Esters to the Corresponding Acids.

The parent ester was dissolved in methyl alcohol to a concentration of 1M. To this was added 1.2 eq of KOH (as a 4 M solution). The reaction was heated to 60° C. for 6 hrs. The solvent was removed and the residue chormatographed on silica gel using a 94:5:1 DCM:MeOH:HOAe eluent. Yields were greater than 90%.

Example 33

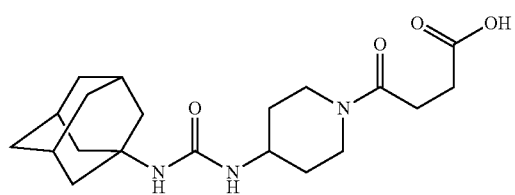 [SMILES: O=C(O)CCC(=O)N1CCC(NC(=O)NC23CC4CC(CC(C4)C2)C3)CC1]

4-[4-(3-Adamantan-1-yl-ureido)-piperidin-1-yl]-4-oxo-butanoic acid (1503)

Mp 196° C. dec. $^1$H NMR (300 MHz, DMSO): 12.14 (br, 1H), 5.67 (d, J=7.8 Hz, 1H), 5.40 (s, 1H), 4.05 (br d, J=13.2 Hz, 1H), 3.71 (br d, J=13.5 Hz, 1H), 3.50 (br, 1H), 3.07 (br t, J=10.8 Hz, 1H), 2.74 (br t, J=10.8 Hz, 1H), 2.50-2.30 (m, 4H), 2.00-1.60 (br m, 17H), 1.40-0.90 (m, 2H).

Example 34

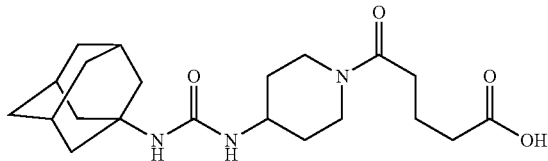 [SMILES: O=C(O)CCCC(=O)N1CCC(NC(=O)NC23CC4CC(CC(C4)C2)C3)CC1]

5-[4-(3-Adamantan-1-yl-ureido)-piperidin-1-yl]-5-oxo-pentanoic acid 1501)

¹H NMR (300 MHz, DMSO): 12.11 (br, 1H), 5.66 (br d, J=7.1 Hz, 1H), 5.40 (br s, 1H), 4.08 (br d, J=13.1 Hz, 1H), 3.67 (br d, J=13.6 Hz, 1H), 3.58-3.41 (br, 1H), 3.05 (br t, J=11.7 Hz, 1H), 2.75 (br t, J=11.7 Hz, 1H), 2.28 (t, J=7.4 Hz, 2H), 2.21 (t, J=7.4 Hz, 2H), 200-1.50 (br m, 19H), 1.20-0.90 (m, 2H).

Example 35

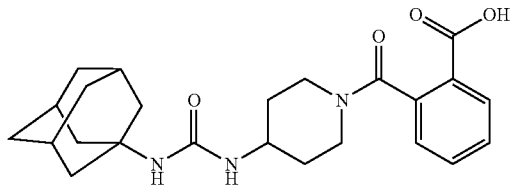 [SMILES: O=C(NC1CCN(C(=O)c2ccccc2C(=O)O)CC1)NC12CC3CC(CC(C3)C1)C2]

2-[4-(3-Adamantan-1-yl-ureido)-piperidine-1-carbonyl]-benzoic acid (1507)

Mp 219° C. dec. ¹H NMR (300 MHz, DMSO): 13.16 (br, 1H), 7.60 (dd, J=7.7, 0.89 Hz, 1H), 7.62 (td, J=7.5, 0.9 Hz, 1H), 7.49 (td, J=7.6, 1.0 Hz, 1H), 7.27 (d, J=7.3 Hz, 1H), 5.71 (d, J=7.4 Hz, 1H), 5.45 (s, 1H), 4.24-4.12 (br m, 1H), 3.60-3.45 (br, 1H), 3.22-3.10 (br m, 1H), 3.05-2.85 (br, 2H), 2.02-1.38 (br m, 17H), 1.35-1.06 (br m, 2H).

Example 36

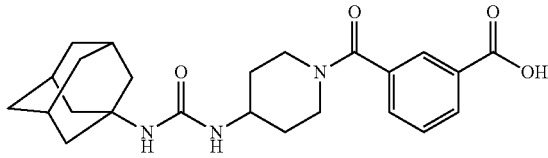 [SMILES: O=C(NC1CCN(C(=O)c2cccc(C(=O)O)c2)CC1)NC12CC3CC(CC(C3)C1)C2]

3-[4-(3-Adamantan-1-yl-ureido)-piperidine-1-carbonyl]-benzoic acid (1505)

¹H NMR (300 MHz, DMSO): 13.23 (br, 1H), 7.97 (br d, J=7.4 Hz, 1H), 7.86 (br s, 1H), 7.59 (br d, J=7.3 Hz, 1H), 7.4 (t, J=7.3 Hz, 1H), 5.70 (br d, 7.8 Hz, 1H), 5.42 (br s, 1H), 4.30-4.10 (br d, J=7.3 Hz, 1H), 7.54 (t, J=7.3 Hz, 1H), 5.70 (br d, 7.8 Hz, 1H), 5.42 (br s, 1H), 4.30-4.10 (br, 1H), 3.65-2.95 (br m, 4H), 2.00 (br m, 17H), 1.35-1.06 (br m, 2H.

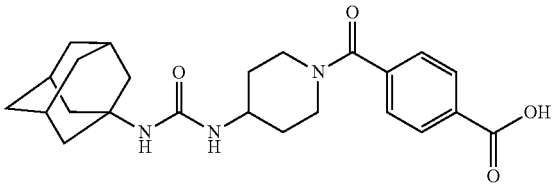 [SMILES: O=C(NC1CCN(C(=O)c2ccc(C(=O)O)cc2)CC1)NC12CC3CC(CC(C3)C1)C2]

4-[4-(3-Adamantan-1-yl-ureido)-piperindine-1-carbonyl]-benzoic acid (1523)

Mp 245-251° C. ¹H NMR (300 MHz, DMSO): 13.12 (br, 1H), 7.95 (d, J=7.5 Hz, 1H), 7.45 (d, J–7.5 Hz, 1H), 5.69 (d, J=5.7 Hz, 1H), 544 (s, 1H), 4.29-4.11 (br, 1H), 3.65-2.88 (br m, 4H), 2.00-1.50 (br m, 17H), 1.35-1.06 (br m, 2H),

Example 37

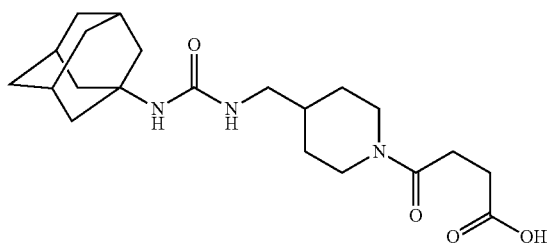 [SMILES: O=C(O)CCC(=O)N1CCC(CNC(=O)NC23CC4CC(CC(C4)C2)C3)CC1]

4-{4-[(3-Adamantan-1-yl-ureido)-methyl]-piperidin-1-yl}-4-oxo-butanoic acid (1502)

¹H NMR (300 MHz, DMSO): 12.70-10.93 (br, 1H), 5.71 (br t, J=5.2 Hz, 1H), 5.44 (s, 1H), 4.30 (br d, J=11.4 Hz, 1H), 3.83 (br d, J=12.0 Hz, 1H), 2.91 (br t, J=12.9 Hz, 1H), 2.84-2.75 (m, 2H), 2.50-2.30 (br m, 5H), 2.10-1.50 (br m, 18H), 1.15-0.80 (m, 2H).

Example 38

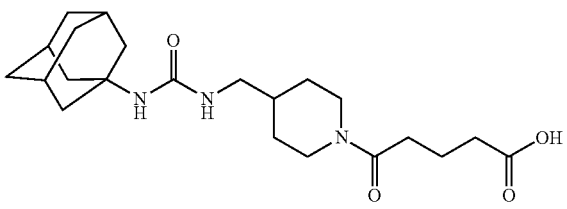 [SMILES: O=C(O)CCCC(=O)N1CCC(CNC(=O)NC23CC4CC(CC(C4)C2)C3)CC1]

5-{4-[(3-Adamantan-1-yl-ureido)-methyl]-piperidin-1-yl}-5-oxo-pentanoic acid (1500)

¹H NMR (300 MHz, DMSO); 12.80-11.10 (br, 1H), 5.70 (br t, J=5.6 Hz, 1H), 5.44 (s, 1H), 4.33 (br d, J=12.4 Hz, 1H), 3.80 (br d, J=13.0 Hz, 1H), 2.89 (br t, J=12.8 Hz, 1H), 2.83-

2.76 (m, 2H), 2.44 (br t, J=12.6 Hz, 1H), 2.27 (t, J=7.5 Hz, 2H), 2.21 (t, J=7.4 Hz, 2H), 2.10-1.50 (br m, 20H), 1.20-0.95 (m, 2H).

Example 39

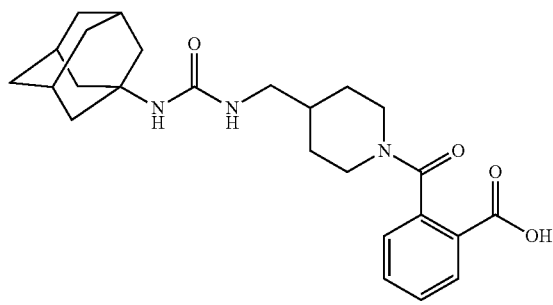 [SMILES: O=C(NCC1CCN(C(=O)c2ccccc2C(=O)O)CC1)NC12CC3CC(CC(C3)C1)C2]

2-{4-[(3-Adamantan-1-yl-ureido)-methyl]-piperidine-1-carbonyl}-benzoic acid (1506)

MP 193° C. dec. ¹H NMR (300 MHz, DMSO): 13.60-11.60 (br, 1H), 7.87 (br d, J=7.7 Hz, 1H), 7.53 (br t, J=7.4 Hz, 1H), 7.42 (br t, J=7.4 Hz, 1H), 7.18 (br d, J=7.4 Hz, 1H), 5.75 (br m, 1H), 5.47 (br, 1H), 4.45 (br d, J=12.4 Hz, 1H), 3.17 (br d, J=11.5 Hz, 1H), 2.99-2.55 (br m, 4H), 2.10-1.50 (br m, 18H), 1.20-0.95 (m, 2H).

Example 40

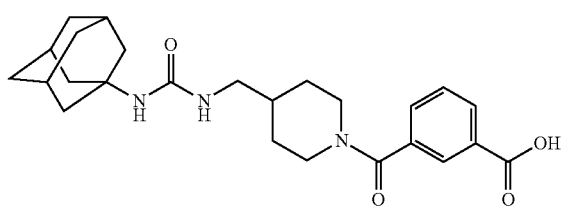 [SMILES: O=C(NCC1CCN(C(=O)c2cccc(C(=O)O)c2)CC1)NC12CC3CC(CC(C3)C1)C2]

3-{4-[(3-Adamantan-1-yl-ureido)-methyl]-piperidine-1-carbonyl}-benzoic acid (1504)

¹H NMR (300 MHz, DMSO): 13.53-12.70 (br, 1H), 7.97 (d, J=1.3 Hz. 1H), 7.85 (s, 1H), 7.61-7.51 (m, 2H), 5.75-5.68 (br m, 1H), 5.43 (s, 1H), 4.50-4.37 (br, 1H), 3.50-2.55 (br m, 5H), 2.10-1.50 (br m, 18H), 1.20-0.92 (m, 2H).

Example 41

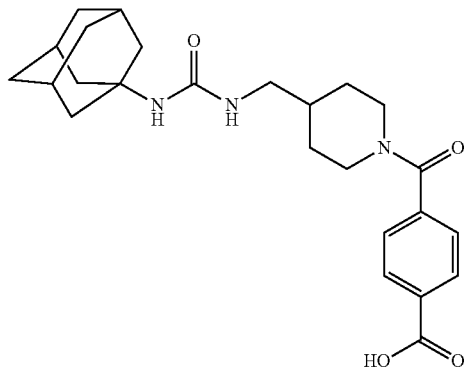 [SMILES: O=C(NCC1CCN(C(=O)c2ccc(C(=O)O)cc2)CC1)NC12CC3CC(CC(C3)C1)C2]

4-{4-[(3-Adamantan-1-yl-ureido)-methyl]-piperidine-1-carbonyl}-benzoic acid (1522)

Mp 147° C. dec. ¹H NMR (300 MHz, DMSO): 13.80-12.40 (br, 1H), 7.96 (d, J=8.1 Hz, 1H), 7.43 (d, J=8.2 Hz, 1H), 5.72 (t, J=5.8 Hz, 1H), 5.45 (s, 1H), 4.44 (br d, J=11.5 Hz, 1H), 3.50 (br m, 1H), 3.50-2.55 (br m, 5H), 2.10-1.50 (br m, 18H), 1.20-0.90 (m, 2H).

Example 42

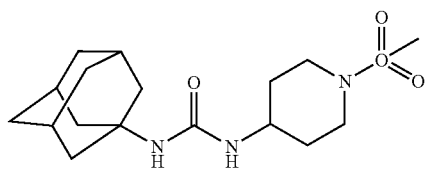

N-(1-Methanesulfonyl piperidin-4-yl)-N'-(adamant-1-yl) urea

N-Methanesulfonyl piperid-4-yl amide

A reactor was charged with 1.00 mole-equivalent of 4-piperidinecarboxamide, 16.4 mole-equivalents of THF, and 1.2 mole-equivalents of N,N-(diisopropyl)ethylamine under a nitrogen atmosphere. The resulting mixture was cooled to 0-5° C. internal, and 1.2 mole-equivalents of methanesulfonyl chloride was added at such a rate as to maintain an internal temperature of less than 10° C. After addition was complete, the reaction mixture was stirred allowing the temperature to rise to 20° C. internal. The reaction contents was monitored until the amount of unreacted 4-piperidinecarboxamide was less than 1% relative to N-methanesulfonyl piperid-4-yl amide product (typically about 2-12 hours). The precipitated product was collected by filtration then washed with dichloromethane to remove excess (diisopropl)ethylamine hydrochloride. The solid product was dried to constant weight in a vacuum oven under a nitrogen bleed maintaining an internal temperature of ≤50° C. to afford product was a light yellow solid in 87% yield. Mp.: 126-128° C. $^1$H NMR(DMSO)-d$_6$) δ: 7.30 (s, 1H), 6.91 (s, 1H), 3.46-3.59 (m, 2H), 2.83 (s, 2H), 2.60-2.76 (m, 2H), 2.08-2.24 (m, 1H). 1.70-1.86 (m, 2H), 1.43-1.62 (m, 2H): MS: 207 [M+H]$^+$.

N-(1-Methanesulfonyl piperidin-4-yl)-N'-(adamant-1-yl) urea

A reactor was charged with 1.00 mole-equivalents of N-methanesulfonyl piperid-4-yl amide, 1.06 mole-equivalents of 1-adamantyl amine, and 39.3 mole-equivalents of acetonitrile, and the resulting mixture was heated to 40° C. internal under a nitrogen atmosphere. (Diacetoxyiodo)benzene (1.20 mole-equivalents) was charged portionwise in such a way that the reaction mixture was maintained below 75° C. internal. After the (diacetoxyiodo)benzene had been added, the reaction mixture was heated at 65-70° C. internal, and the reaction contents monitored until the amount of unreached 1-adamantyl amine was less than 5% relative to product N-(1-methanesulfonyl piperidin-4-yl)-N'-(adamant-1-yl) urea (typically less than about 6 hours). The resulting mixture was cooled to 20° C. internal and filtered to remove a small amount of insoluble material. The filtrate was allowed to stand for 48 hours at which point the precipitated product was collected by filtration. The solid product was dried to constant weight in a vacuum oven under a nitrogen bleed maintaining an internal temperature of ≤50° C. to afford product in 58% yield based on N-methanesulfonyl piperid-4-yl amide. $^1$H NMR(CDCl$_3$) δ: 3.95-4.08 m, 2H), 3.74-3.82 (m, 2H), 3.63-3.82 (m, 1H), 3.78 (s, 3H), 3.70-3.80 (m, 2H), 2.02-2.12 (m, 5H), 1.90 (s, 6H), 1.67 (s, 6H), 1.40-1.50 (m, 2H); MS: 356 [M+H]$^+$; m.p. 228-229° C.

Example 43-63

Synthesized as described previously in Jones, P. D., et al. *Bioorganic & medicinal chemistry letters* 2006, 16, 212.

Example 43

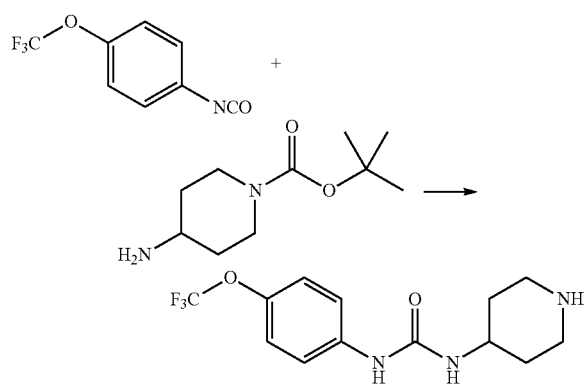

1-Piperidin-4-yl-3-(4-trifluoromethoxy-phenyl)-urea (1570)

$^1$H NMR (300 MHz, D6 DMSO☐☐) δ ppm 8.61 (s, 1H), 7.63-7.26 (m, 2H), 7.20 (d, J=8.29 Hz, 2H), 6.25 (d, J=7.57 Hz, 1H), 3.60-3.38 (m, 1H), 2.87 (td, J=11.85, 3.18, 3.18 Hz, 2H), 1.79-1.64 (m, 2H), 2.48-2.1 (m, 2H), 1.20 (qd, J=11.06, 3.83 Hz, 2H); m.p. 169-173° C.

Example 44

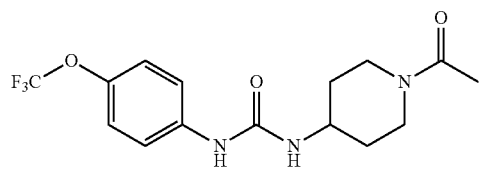 [SMILES: CC(=O)N1CCC(NC(=O)Nc2ccc(OC(F)(F)F)cc2)CC1]

1-(1-Acetyl-piperidin-4-yl)-3-(4-trifluoromethoxy-phenyl)-urea (1555)

$^1$H NMR (300 MHz, D6 DMSO☐☐☐) δ ppm 8.07 (s, 1H), 7.48-7.28 (m, 2H), 7.09 (d, J=8.93 Hz. 2H), 5.87 (d, J=7.57 Hz, 1H), 4.53-4.26 (m, 1H), 4.05-3.82 (m, 1H), 3.82-3.70 (m, 1H, 3.29-3.06 (m, 1H), 3.01-2.69 (m, 1H), 2.11 (s, 3H), 2.14-1.87 (m, 2H), 1.40-1.25 (m, 2H); m.p. 198-202° C.

Example 45

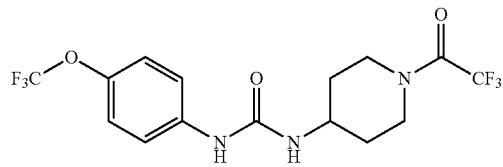 [SMILES: O=C(Nc1ccc(OC(F)(F)F)cc1)NC1CCN(C(=O)C(F)(F)F)CC1]

(1-[1-(2,2,2-Trifluoro-acetyl)-piperidin-4-yl]-3-(4-trifluoromethoxy-phenyl)-urea (1591)

$^1$H NMR (300 MHz, D6 DMSO☐☐) δ ppm 7.41-7.03 (m, 5H), 5.21 (s, 1H), 4.50-4.31 (m, 1H), 3.95 (brd, J=2H), 3.18 (m, 1H), 2.90 (m, 1H), 2.19-1.90 (m, 1H), 1.29 (m, 2H), m.p. 150-14° C.

Example 46

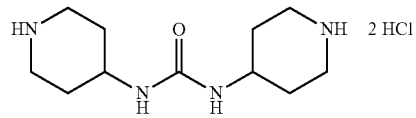 [SMILES: O=C(NC1CCNCC1)NC1CCNCC1]

1,3-Di-piperidin-4-yl-urea (1604)

¹H NMR (300 MHz, D6 DMSO☐☐) δ ppm 9.19-8.89 (m, 2H), 3.74-3.55 (m, 1H), 3.26-3.12 (m, 2H), 2.95-2.80 (m, 2H), 1.99-1.79 (m, 2H), 1.65-1.45 (m, 2H).

Example 47

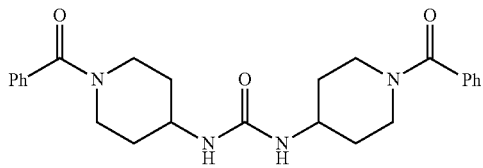 [SMILES: O=C(NC1CCN(C(=O)c2ccccc2)CC1)NC1CCN(C(=O)c2ccccc2)CC1]

1,3-Bis-(1-benzoyl-piperidin-4-yl)-urea (1605)

¹H NMR (300 MHz, CDCl₃ ☐☐) δ ppm 7.67-6.93 (m, 5) 5.39 (d, J=7.98 Hz, 1H), 4.78-4.24 (m, 1H), 4.05-3.43 (m, 2H), 3.34-2.63 (m, 2H), 2.20-1.57 (m, 2H), 1.49-0.71 (m, 2H): ¹³C NMR (75 MHz, CDCl₃) δ ppm 170.84, 157.25, 135.86, 130.14, 128.84, 126.94, 46.91, 46.66, 41.47, 33.97, 32.67.

Example 48

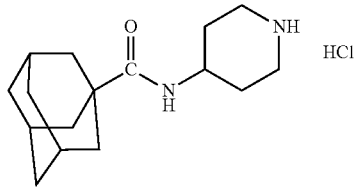 [SMILES: O=C(NC1CCNCC1)C12CC3CC(CC(C3)C1)C2 ; Cl]

Adamantane-1-carboxylic acid piperidin-4-ylamide

¹H NMR (300 MHz, CDCl₃ ☐☐) δ ppm 8.79 (d, J=7.53 Hz, 2H), 7.39 (d, J=7.53 Hz, 1H), 3.86-3.73 (m, 1H), 2.38-3.17 (m, 2H), 2.99-2.81 (m, 2H), 2.01-1.53 (m, 19H).

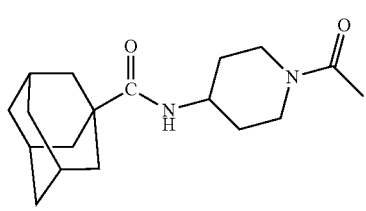 [SMILES: CC(=O)N1CCC(NC(=O)C23CC4CC(CC(C4)C2)C3)CC1]

Adamantane-1-carboxylic acid (1-acetyl-piperidin-4-yl)-amide (1641)

¹H NMR (300 MHz, CDCl₃ ☐☐) δ ppm 5.49 (d, J=7.38 Hz, 1H), 4.60-4.51 (m, 1H), 4.07-3.90 (m, 1H), 3.79 (ddd, J=13.76, 5.64, 3.68 Hz, 1H), 3.17 (ddd, J=14.01, 12.08, 2.76 Hz, 1H), 2.79-2.67 (m, 1H), 2.10 (s, 3H), 2.09-1.65 (m, 17H), 137-1.21 (m, 2H).

Example 49

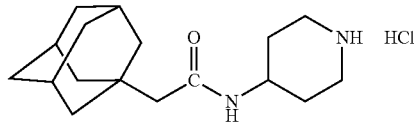 [SMILES: O=C(CC12CC3CC(CC(C3)C1)C2)NC1CCNCC1 ; Cl]

2-Adamantan-1-yl-N-piperidin-4-yl-acetamide

¹H NMR (300 MHz, D6 DSMO☐☐) δ ppm 9.04-8.94 (m, 2H), 7.90 (d, J=7.49 Hz, 1H), 3.99-3.48 (m, 1H), 3.24-3.12 (m, 2H), 3.00-2.79 (m, 2H), 2.10-1.22 (m, 2H).

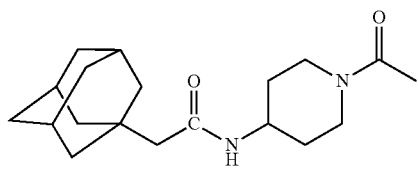 [SMILES: CC(=O)N1CCC(NC(=O)CC23CC4CC(CC(C4)C2)C3)CC1]

N-(1-Acetyl-piperidin-4-yl)-2-adamantan-1-yl-acetamide (1642)

¹H NMR (300 MHz, CDCl₃ ☐☐) δ ppm 5.56 (d, J=7.73 Hz, 1H), 4.55 (d, J=14.17 Hz, 1H), 4.08-3.93 (m, 1H), 3.84-3.73 (m, 1H), 3.22-3.10 (m, 1H), 2.78-2.65 (m, 1H), 2.09 (s, 1H), 2.07-1.92 (m, 3H), 1.91 (s, 2H), 1.76-1.55 (m, 12H), 1.39-1.21 (m, 2H).

Example 50

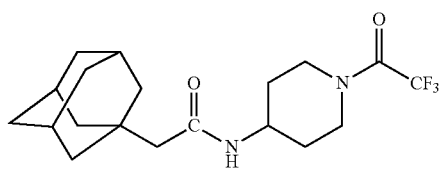 [SMILES: O=C(CC12CC3CC(CC(C3)C1)C2)NC1CCN(C(=O)C(F)(F)F)CC1]

2-Adamantan-1yl-N-[1-(2,2,2-trifluoro-acetyl)-piperidin-4-yl]-acetamide (1642)

¹H NMR (300 MHz, CDCl₃ ☐☐) δ ppm 5.30 (d, J=7.80 Hz, 1H), 4.56-4.46 (m, 1H), 4.16-3.94 (m, 2H), 3.29-3.17 (m, 1H), 2.96-2.85 (m, 1H), 2.23-1.51 (m, 19H), 1.47-1.31 (m, 2H).

Example 51

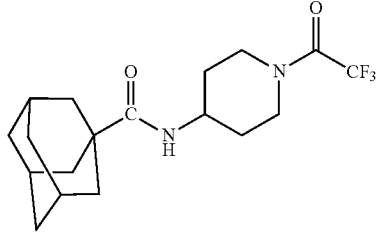 [SMILES: O=C(N1CCC(NC(=O)C23CC4CC(CC(C4)C2)C3)CC1)C(F)(F)F]

Adamantane-1-carboxylic acid [1-(2,2,2-trifluoro-acetyl)-piperidin-4-yl]-amide (1643)

¹H NMR (300 MHz, CDCl₃ ☐☐) δ ppm 5.57 (m, 1H), 4.60-4.32 (m, 1H), 4.18-3.85 (m, 2H), 3.36-3.09 (m, 2H), 3.36-3.09 (m, 1H), 3.00-2.77 (m, 1H), 2.17-1.52 (m, 17H), 1.35 (s, 2H).

Example 52

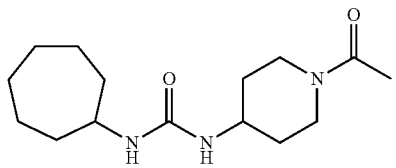 [SMILES: CC(=O)N1CCC(NC(=O)NC2CCCCCC2)CC1]

¹H NMR (300 MHz, CDCl₃ ☐☐) δ ppm 4.68-4.60 (m, 2H), 4.49 (d, J=11.54 Hz, 1H), 392-3.66 (m, 3H), 3.24-3.10 (m, 1H), 2.83-2.71 (m, 1H), 2.11 (s, 3H), 2.09-1.11 (m, 16H).

Example 53

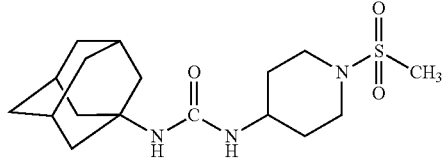 [SMILES: CS(=O)(=O)N1CCC(NC(=O)NC23CC4CC(CC(C4)C2)C3)CC1]

1-Adamantan-1yl-3-(1-methanesulfonyl-piperidin-4-yl)-urea (1701)

¹H NMR (300 MHz, CDCl₃ ☐☐) δ ppm 4.16-4.00 (m, 2H), 3.82-3.60 (m, 3H), 2.78 (s, 3H), 2.76-2.69 (m, 2H), 2.12-1.61 (m, 17H), 1.53-1.36 (m, 2H).

Example 54

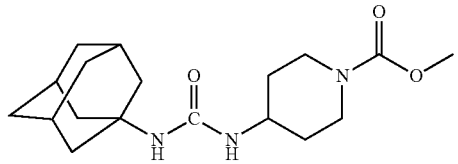 [SMILES: COC(=O)N1CCC(NC(=O)NC23CC4CC(CC(C4)C2)C3)CC1]

4-(3-Adamantan-1-yl-ureido)-piperidine-1-carboxylic acid methyl ester (1702)

¹H NMR (300 MHz, CDCl₃ ☐☐) δ ppm 5.68 (d, J=7.56 Hz, 1H), 5.42 (s, 1H), 3.82-3.72 (m, 2H), 3.57 (s, 3H), 3.53-3.40 (m, 1H), 3.00-2.85 (m, 2H), 2.03-1.52 (m, 17H), 1.20-1.04 (m, 2H).

Example 55

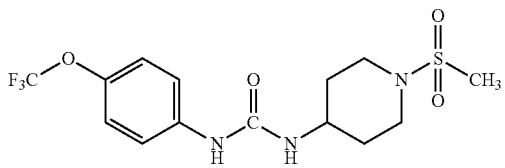 [SMILES: CS(=O)(=O)N1CCC(NC(=O)Nc2ccc(OC(F)(F)F)cc2)CC1]

1-(1-Methanesulfonyl-piperidin-4-yl)-3-(4-trifluoromethoxy-phenyl)-urea (1709)

¹H NMR (300 Hz, CDCl₃ ☐☐) δ ppm 8.04 (s, 1H), 7.44-7.38 (m, 2H), 7.09 (d, K=8.36 Hz, 2H), 5.93 (d, J=7.70 Hz, 1H), 4.00-3.55 (m, 3H), 2.90-2.78 (m, 2H), 2.81 (s, 3H), 2.61-2.55 (m, 2H), 2.15-1.99 (m, 2H), 1.61-1.45 (m, 2H).

Example 56

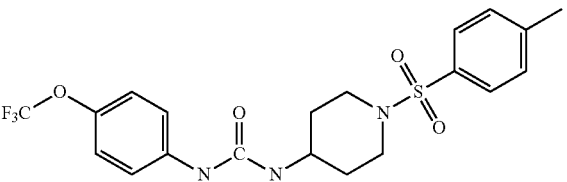

1-[1-(Toluene-4-sulfonyl)-piperidin-4-yl]-3-(4-trifluoromethoxy-phenyl)-urea (1711)

¹H NMR (300 MHz, CDCl₃ ☐☐) δ ppm 7.91 (s, 1H) (d, J=8.22 Hz, 2H), 7.38-7.30 (m, 4H), 7.06 (d, J=8.84 Hz, 1H), 5.78 (s, 1H), 3.77-3.47 (m, 3H), 2.48-2.35 (m, 2H), 2.44 (s, 3H), 2.05-1.93 (m, 2H), 1.57-1.41 (m, 2H).

Example 57

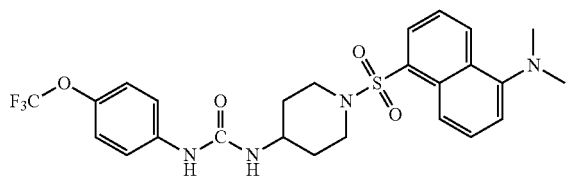 [SMILES: CN(C)c1cccc2c(S(=O)(=O)N3CCC(NC(=O)Nc4ccc(OC(F)(F)F)cc4)CC3)cccc12]

1-[1-(5-Dimenthylamino-naphthalene-1-sulfonyl)-piperidin-4-yl]-3-(4-trifluoromethoxy-phenyl)-urea (1710)

$^1$H NMR (300 MHz, CDCl$_3$ ☐☐) δ ppm 8.59 (d, J=8.50 Hz, 1H), 8.32 (d, J=8.71 Hz, 1H), 8.18 (dd, J=7.35, 1.19 Hz, 1H), 7.54 (ddd, J=8.0, 7.51, 3.20 Hz, 2H), 7.29-7.22 (m, 2H), 7.19 (d, J=7.15 Hz, 1H), 7.02 (d, J=8.45 Hz, 2H), 6.93 (s, 1H), 5.19 d, K=7.73 Hz, 1H), 3.91-3.64 (m, 3H, 3.89 (s, 6H), 2.86-2.72 (m, 2H), 2.06-1.92 (m, 2H) 1.64-1.46 (m, 2H).

Examples 58-64

These chemicals were synthesized by the direct reaction of amine with isocyanate following previously described procedures in Morisseau, C., et al. *Biochemical Pharmacology* 2002, 63, 1599, Jones. P. D., et al. *Bioorganic & medicinal chemistry leers* 2006, 16-5212.

Example 58

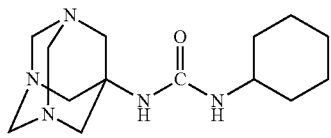 [SMILES: O=C(NC1CCCCC1)NC12CN3CN(CN(C3)C1)C2]

1-Cyclohexyl-3-(1,3,5-triaza-tricylco[3.3.1.1$^{3.7}$]dec-7-yl)-urea (1549)

$^1$H NMR (300 MHz, D6 DMSO☐☐) δ ppm 5.62 (s, 1H), 5.37 (s, 1H), 4.25 (d, J=11. Hz. 3), 3.90 (d. J=10.8 Hz, 3H), 3.50-3.21 (m, 6H), 2.50 (s, 1H), 1.82-1.59 (m, 5H) 1.15-0.95 (m, 5H); m.p. 150-154° C.

Example 59

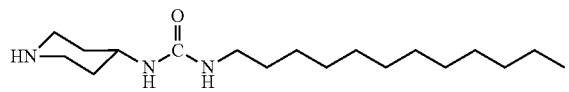

1-Dodecyl-3-piperidin-4-yl-urea (1550)

$^1$H NMR (300 MHz, D6 DMSO☐☐) δ ppm 8.79-8.35 (m, 3H), 3.74-3.55 (m, 1H), 3.26-3.12 (m, 4H), 2.95-2.80 (m, 2H), 1.99-1.79 (m, 2H), 1.65-1.25 (m, 22H), 0.97 (t, J=12.8 Hz, 3H); m.p. 102-105° C.

Example 60

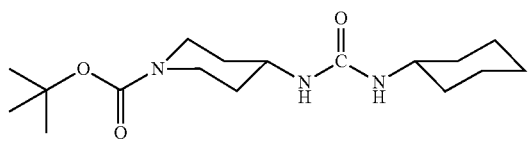 [SMILES: CC(C)(C)OC(=O)N1CCC(NC(=O)NC2CCCCC2)CC1]

4-(3-Cyclohexyl-ureido)-piperidine-1-carboxylic acid tert-butyl ester (1551)

$^1$H NMR (300 MHz, CDCl$_3$☐☐) δ ppm 4.26-4.16 (t, J=8.6 Hz. 2H), 4.11-3.86 (m, 2H), 3.80-3.64 (m, 1H), 3.55-3.39 (m, 1H), 2.94-2.78 (t, J=12.1 Hz, 2H), 1.98-1.87 (m, 4H), 1.75-1.65 (m, 3H), 1.45-1.95 (m, 16H); m.p. 167-169° C.

Example 61

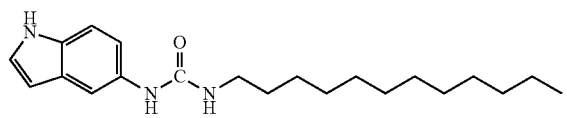 [SMILES: CCCCCCCCCCCCNC(=O)Nc1ccc2[nH]ccc2c1]

1-Dodecyl-3-(1H-indol-5-yl)-urea (1553)

$^1$H NMR (300 MHz, D6 DMSO☐☐) δ ppm 10.9 (s, 1H), 7.50 (s, 1H), 7.30-7.18 (m, 2H), 7.00-6.90 (m, 1H), 6.19 (s, 1H), 6.00-5.95 (m, 1H), 3.41-3.18 (m, 2H), 1.60-1.10 (m, 2H), 0.97 (t, J=12.8 Hz, 3H); m.p. 110-113° C.

Example 62

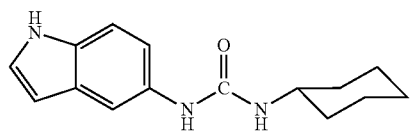 [SMILES: O=C(Nc1ccc2[nH]ccc2c1)NC1CCCCC1]

1-Cyclohexyl-3-(1H-indol-5-yl)-urea (1554)

$^1$H NMR (300 MHz, D6 DMSO☐☐) δ ppm 10.8 (s, 1H), 8.00 (s, 1H), 7.55 (s, 1H), 7.25-7.15 (m, 2H), 6.95-6.87 (m, 1H), 6.1 (s, 1H), 5.95-5.90 (m, 1H), 2.58-2.42 (m, 1H), 1.85-1.05 (m, 10H); m.p. 145-148° C.

Example 63

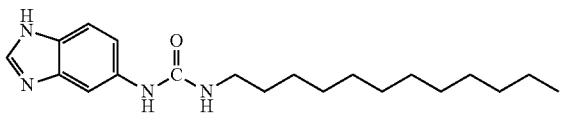 [SMILES: CCCCCCCCCCCCNC(=O)Nc1ccc2[nH]cnc2c1]

1-(1H-Benzoimidazol-5-yl)-3-dodecyl-urea (1568)

$^1$H NMR (300 MHz, D6 DMSO☐☐) δ ppm 8.35-8.25 (m, 2H), 7.35-7.20 (m, 2H), 6.65-6.50 (m, 1H), 5.40-4.85 (m, 2H), 3.38-3.21 (m, 2H), 1.40-1.1.15 (m, 20H), 0.85 (t, J=7.6 Hz, 3H), m.p. 107-109° C.

Example 64

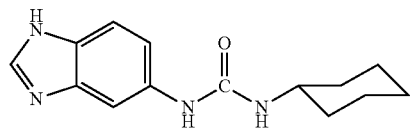 [SMILES: O=C(Nc1ccc2[nH]cnc2c1)NC1CCCCC1]

1-(1H-Benzoimidazol-5-yl)-3-cyclohexyl-urea (1569)

$^1$H NMR (300 MHz, D6 DMSO☐☐) δ ppm 8.41-8.20 (s, 1H), 8.15-8.00 (m. 1H), 7.35-7.15 (m, 2H), 6.6-6.47 (m, 1H), 5.40-4.90 (m, 2H), 2.55-2.47 (m, 1H), 1.95-1.6 (m, 10H), m.p. 143-149° C.

Example 65

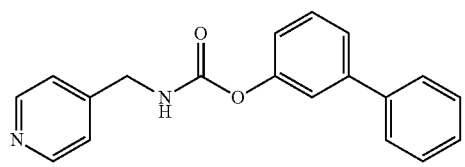 [SMILES: O=C(NCc1ccncc1)Oc1cccc(-c2ccccc2)c1]

Pyridin-4-ylmethyl-carbamic acid biphenyl-3-yl ester (1557)

White fine crystal. $^1$H NMR (CDCl$_3$): 8.60 (d, J=5.70 Hz, 2H), 7.10-7.50 (m, 11H), 5.56 (br, 1H), 4.50 (d, J=6.30 Hz, 2H); m.p.: 132 C.

Example 66

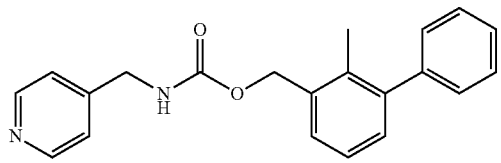 [SMILES: Cc1c(COC(=O)NCc2ccncc2)cccc1-c1ccccc1]

Pyridin-4-ylmethyl-carbamic acid 2-methyl-biphenyl-3-ylmethyl ester (1558)

While sponge-like crystal, $^1$H NMR (CDCl$_3$): 8.56 (d, J=5.70 Hz, 2H), 7.20-7.45 (m, 10), 5.25 (s, 3H), 4.2 (d, J=6.30 Hz, 2H), 2.25 (s, 3H): m.p. 103° C.

Example 67

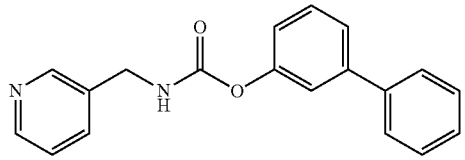 [SMILES: O=C(NCc1cccnc1)Oc1cccc(-c2ccccc2)c1]

Pyridin-3-ylmethyl-carbamic acid biphenyl-3-yl ester (1559)

White crystal, $^1$H NMR (CDCl$_3$): 8.62 (s, 1H), 8.57 (dd, J$_1$=1.20 Hz, J$_2$=4.50 Hz. 1H), 7.70-7.75 (m, 11H), 7.56-7.59 (m, 12H), 7.27-7.46 (m, 7H), 7.11-7.15 (m, 1H), 5.4 (br, 1H), 4.49 (d, J=6.30 Hz, 2H); m.p. 113° C.

Example 68

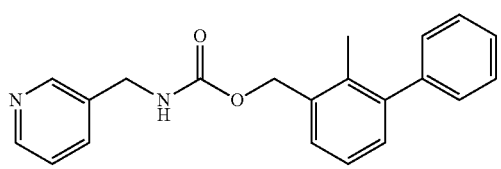 [SMILES: Cc1c(COC(=O)NCc2cccnc2)cccc1-c1ccccc1]

Pyridin-3-ylmethyl-carbamic acid 2-methyl-biphenyl-3-ylmethyl ester (1560)

White crystal, $^1$H NMR (CDCl$_3$): 8.5 (m, 2H), 7.76 (d, J=7.50 Hz, 1H), 7.22-7.41 (m, 9H), 5.23 (s, 2H), 5.19 (br, 1H), 4.42 (d, J=5.70 Hz, 2H), 2.23 (s, 3H); m.p. 110° C.

Example 69

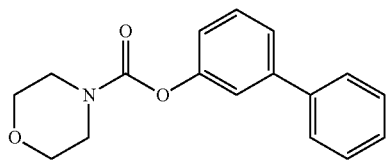

Morpholine-4-carboxylic acid biphenyl-3-yl ester (1561)

White crystal, $^1$H NMR (CDCl$_3$): 7.57-7.60 (m, 2H), 7.27-7.46 (m, 6H), 7.08-7.13 (m, 1H), 3.60-3.79 (m, 8H); m.p. 97° C.

Example 70

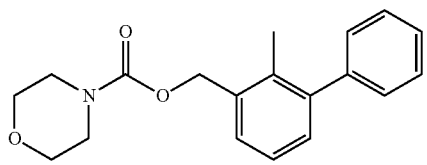 [SMILES: Cc1c(COC(=O)N2CCOCC2)cccc1-c1ccccc1]

Morpholine-4-carboxylic acid 2-methyl-biphenyl-3-ylmethyl ester (1562)

Colorless sticky oil. $^1$H NMR (CDCl$_3$): 7.23-7.45 (m, 8H), 5.23 (s, 2H), 3.68 (br, 4H), 3.50-3.53 (m, 4H), 2.23 (s, 3H).

Example 71

This example provides assays and illustrates the inhibition of human soluble epoxide hydrolases by compounds of the invention.

Enzyme Preparation

Recombinant human sEH was produced in a baculovirus expression system and purified by affinity chromatography. The preparations were at least 97% pure as judged by SDS-PAGE and scanning densitometry. No detectable esterase or glutathione transferase activity, which can interfere with this sEH assay, was observed. Protein concentration was quantified by using the Pierce BCA assay using Fraction V bovine serum albumin as the calibrating standard.

IC$_{50}$ Assay Conditions

IC$_{50}$ values were determined in one of three methods. One method uses racemic 4-nitrophenyl-trans-2,3-epoxy-3-phenylpropyl carbonate as substrate. Enzyme (0.24 µM human sEH) was incubated with inhibitors for 5 min in sodium phosphate buffer, 0.1 M pH 7.4 at 30° C. before substrate introductions ([S]=40 µM). Activity was assessed by measuring the appearance of the 4-nitrophenolate anion at 405 nm at 30° C. during 1 min (Spectramax 200; Molecular Devices). Assays were performed in triplicate. IC$_{50}$ is a concentration of inhibitor, which reduces enzyme activity by 50%, and was determined by regression of at least five datum points with a minimum of two points in the linear region of the curve on either side of the IC$_{50}$. The curve was generated from at least three separate runs, each in triplicate.

Other IC$_{50}$ values were determined using the procedure described in *Analytical Biochemistry* 343 66-75 (2005) using cyano(6-methoxy-naphthalen-2-yl)methyl trans-[(3-phenyloxiran-2-yl)methyl]carbonate as a substrate. Enzymes (0.96 nM for human sEH) were incubated with inhibitors ([I]=10, 000 nM) for 5 mm in BisTris-HCl buffer (25 mM, pH 7.0, containing 0.1 mg/ml of BSA) at 30° C. prior to substrate introduction. ([S]=5 1M). Enzyme activity was measured by monitoring the appearance of 6-methoxy-2-naphthaldehyde. Assays were performed in triplicate. By definition, IC$_{50}$ values are concentrations of inhibitor that reduce enzyme activity by 50%. IC$_{50}$ values were determined by regression of at least five datum points, with a minimum of two datum points in the linear region of the curve on either side of the IC$_{50}$ values. The curve was generated from at least three separate runs, each in triplicate.

Other inhibition potencies were determined using a fluorescent based high-throughput assay. Inhibitors in solution at 10 mM in DMSO were serially diluted by 10-fold increment in Bis/Tris HCl buffer (25 mM pH 7.0) containing 0.1 mg/mL of BSA (Buffer A). In black 96well plates, 20 µL of the inhibitor dilution or buffer were delivered in every well, and then 130 µL of Human sEH at ~0.4 µg/mL in solution in Buffer A were added to each well. The plate was then mixed and incubated at room temperature for 5 minutes. Fifty microliters of substrate ((3-Phenyl-oxiranyl)-acetic acid cyano-(6-methoxy-naphthalen-2-yl)-methyl ester; PHOME) at 200 µM in solution in 94:4 Buffer A DMSO was then added to each well to give [S]final 50 µM and [E]final=~4 nM. The plate was then mixed and incubated in the dark at room temperature (=25° C.) for 90 min. Activity was measured by determining the relative quantity of 6-methoxy-2-naphthaldehyde formed with an excitation wavelength of 316 nm and an emission wavelength of 460 mn measured with a SpectraMax M-2 (molecular Devices, Sunnyvale Calif.).

Assays were conducted with the compounds indicated in Table 1-5, as described above.

Example 72

TABLE 1

Inhibition of human sEH by alkyl substituted piperidines:

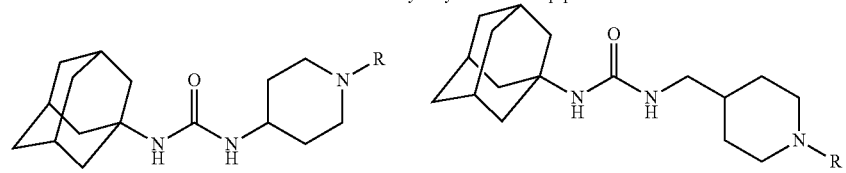

| R | Compound # | IC$_{50}$ (nM) | R | Compound # | IC$_{50}$ (nM) |
|---|---|---|---|---|---|
| H | 1175 | 960 | H | 1118 | 4258 |
| Et | 1152 | 3758 | Et | 1154 | 3949 |
| n-Pr | 1155 | 809 | n-Pr | 1122 | 2578 |
| n-Bu | 1160 | 1249 | n-Bu | 1161 | 613 |
| benzyl | 1158 | 8.4 | benzyl | 1119 | 112 |

This example illustrates the inhibition of human soluble epoxide hydrolyses by compounds of the invention having an alkyl substituted piperidine moiety.

Assays were conducted with the compounds indicated in Table 1, according to established protocols (see, above).

Example 73

This example illustrates the inhibition of human soluble epoxide hydrolases by compounds of the invention having an amide substituted piperidine moiety.

Assays were conducted with the compounds indicated in Table 2, according to established protocols (see, above).

TABLE 2

Inhibition of human sEH by simple amide substituted piperidines:

| R | Compound # | IC$_{50}$ (nM) | R | Compound # | IC$_{50}$ (nM) |
|---|---|---|---|---|---|
| —C(O)Me | 1153 | 14.5 | —C(O)Me | 1156 | 5.0 |
| —C(O)Et | 1163 | 3.2 | —C(O)Et | 1162 | 8.7 |
| —C(O)-n-Pr | 1157 | 2.6 | —C(O)-n-Pr | 1120 | 6.7 |
| —C(O)Ph | 1159 | 1.3 | —C(O)Ph | 1121 | 3.2 |
| 2-pyridyl C(O)— | 1201 | 1.2 | 2-pyridyl C(O)— | 1207 | 7.6 |
| 4-pyridyl C(O)— | 1433 | 1.7 | 4-pyridyl C(O)— | 1435 | 5.4 |
| 3-pyridyl C(O)— | 1434 | 2.1 | 3-pyridyl C(O)— | 1436 | 7.3 |

Example 74

This example illustrates the inhibition of human soluble epoxide hydrolases by compounds of the invention having an amide-ester substituted piperidine moiety.

Assays were conducted with the compounds indicated in Table 3, according to established protocols (see, above).

TABLE 3

Inhibition of human sEH by amide-ester piperidines:

| R | Compound # | IC$_{50}$ (nM) | R | Compound # | IC$_{50}$ (nM) |
|---|---|---|---|---|---|
| -C(O)-CH$_2$-CH$_2$-C(O)-O-CH$_3$ | 1205 | 9.0 | -C(O)-CH$_2$-CH$_2$-C(O)-O-CH$_3$ | 1208 | 6.2 |
| -C(O)-CH$_2$-CH$_2$-CH$_2$-C(O)-O-CH$_3$ | 1206 | 2.7 | -C(O)-CH$_2$-CH$_2$-CH$_2$-C(O)-O-CH$_3$ | 1212 | 3.4 |
| ortho-C(O)-C$_6$H$_4$-C(O)-O-CH$_3$ | 1202 | 1.7 | ortho-C(O)-C$_6$H$_4$-C(O)-O-CH$_3$ | 1210 | 1.8 |
| meta-C(O)-C$_6$H$_4$-C(O)-O-CH$_3$ | 1203 | 1.1 | meta-C(O)-C$_6$H$_4$-C(O)-O-CH$_3$ | 1209 | 4.1 |
| para-C(O)-C$_6$H$_4$-C(O)-O-CH$_3$ | 1204 | 1.1 | para-C(O)-C$_6$H$_4$-C(O)-O-CH$_3$ | 1211 | 1.5 |

Example 75

This example illustrates the inhibition of human soluble epoxide hydrolyses by compounds of the invention having an amide-acid substituted piperidine moiety.

Assays were conduced with the compounds indicated in Table 4, according to established protocols (see, above).

TABLE 4

Inhibition of human sEH by amide-acid piperidines:

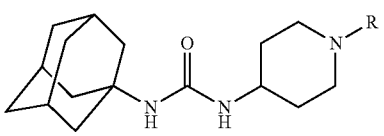 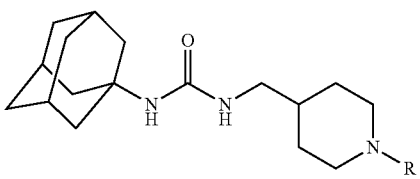

| R | Compound # | IC$_{50}$ (nM) | R | Compound # | IC$_{50}$ (nM) |
|---|---|---|---|---|---|
|  | 1503 | 254.5 |  | 1502 | 174.5 |
| 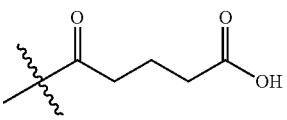 [SMILES: *C(=O)CCCC(=O)O] | 1501 | 72.8 | 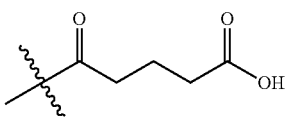 [SMILES: *C(=O)CCCC(=O)O] | 1500 | 41.6 |
| 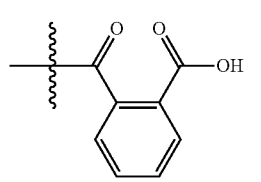 [SMILES: *C(=O)c1ccccc1C(=O)O] | 1507 | 161.2 | 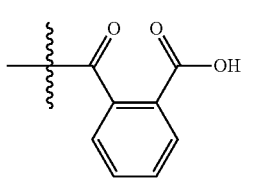 [SMILES: *C(=O)c1ccccc1C(=O)O] | 1506 | 407.1 |
| 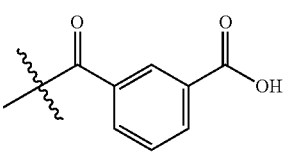 [SMILES: *C(=O)c1cccc(C(=O)O)c1] | 1505 | 10.1 | 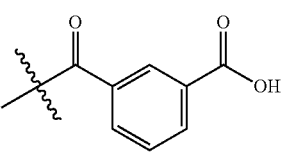 [SMILES: *C(=O)c1cccc(C(=O)O)c1] | 1504 | 43.6 |
| 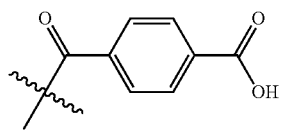 [SMILES: *C(=O)c1ccc(C(=O)O)cc1] | 1523 | 3.3 | 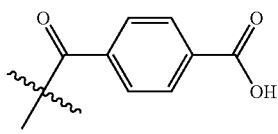 | 1522 | 11.8 |

Example 76

This example provides a table of structures of compounds with various other functionalities included in the invention. For example, the urea pharmacophore can be varied with amide or carbamate functionality to improve physical properties of sEH inhibitors as shown in Table 5a.

Assays were conduced with the compounds indicated in Table 5a and 5b, according to established protocols (see, above).

TABLE 5a

Inhibition of human sEH by 1-substituted-3-n-(substituted)heterocyclic areas, carbamates and amides:

| Compound | Structure | IC$_{50}$ (nM) |
|---|---|---|
| 1549 | 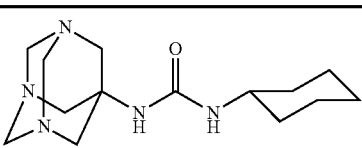 | 13586.4 |
| 1550 | 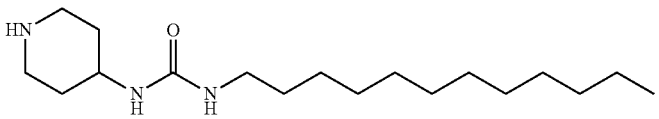 [SMILES: CCCCCCCCCCCCNC(=O)NC1CCNCC1] | 42.5 |

TABLE 5a-continued

Inhibition of human sEH by 1-substituted-3-n-(substituted)heterocyclic areas, carbamates and amides:

| Compound | Structure | IC$_{50}$ (nM) |
| --- | --- | --- |
| 1551 | 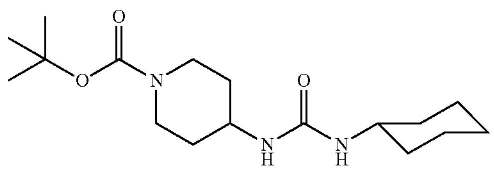 [SMILES: CC(C)(C)OC(=O)N1CCC(NC(=O)NC2CCCCC2)CC1] | 4.3 |
| 1553 | 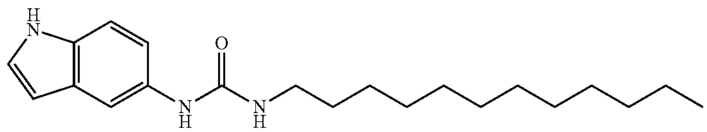 [SMILES: CCCCCCCCCCCCNC(=O)Nc1ccc2[nH]ccc2c1] | 639.1 |
| 1554 | 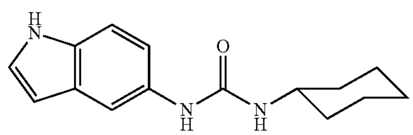 [SMILES: O=C(Nc1ccc2[nH]ccc2c1)NC1CCCCC1] | 87 |
| 1555 | 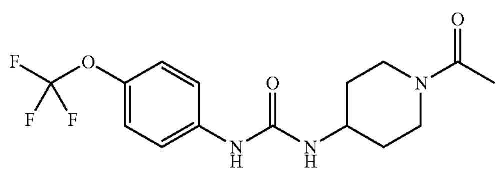 [SMILES: CC(=O)N1CCC(NC(=O)Nc2ccc(OC(F)(F)F)cc2)CC1] | 11.5 |
| 1556 | 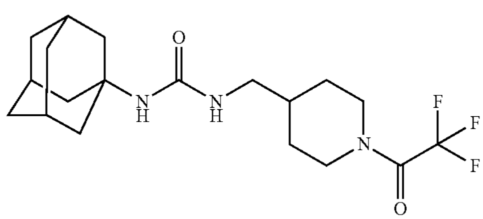 [SMILES: O=C(NCC1CCN(C(=O)C(F)(F)F)CC1)NC12CC3CC(CC(C3)C1)C2] | 1.8 |
| 1557 | 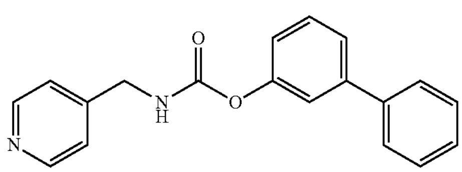 [SMILES: O=C(NCc1ccncc1)Oc1cccc(-c2ccccc2)c1] | 11468.1 |
| 1558 | 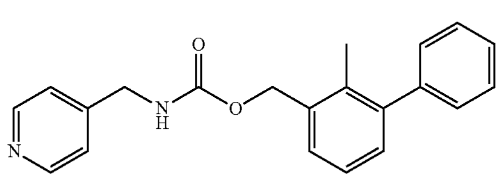 [SMILES: Cc1c(COC(=O)NCc2ccncc2)cccc1-c1ccccc1] | 1329.7 |
| 1559 | 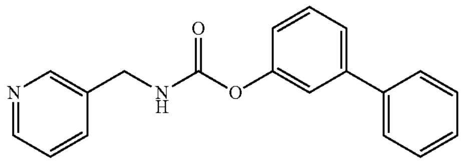 [SMILES: O=C(NCc1cccnc1)Oc1cccc(-c2ccccc2)c1] | 22991.5 |

TABLE 5a-continued

Inhibition of human sEH by 1-substituted-3-n-(substituted)heterocyclic ureas, carbamates and amides:

| Compound | Structure | IC$_{50}$ (nM) |
|---|---|---|
| 1560 | 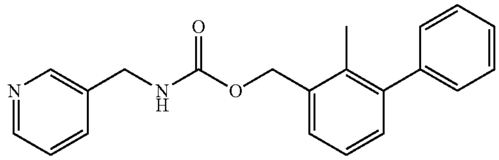 [SMILES: Cc1c(COC(=O)NCc2cccnc2)cccc1-c1ccccc1] | 4413.4 |
| 1561 | 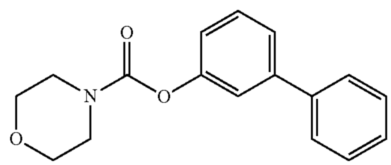 [SMILES: O=C(Oc1cccc(-c2ccccc2)c1)N1CCOCC1] | 65339.4 |
| 1562 | 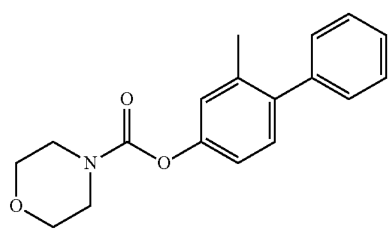 [SMILES: Cc1cc(OC(=O)N2CCOCC2)ccc1-c1ccccc1] | 11994.1 |
| 1567 | 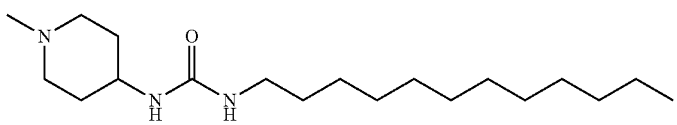 [SMILES: CCCCCCCCCCCCNC(=O)NC1CCN(C)CC1] | |
| 1568 | 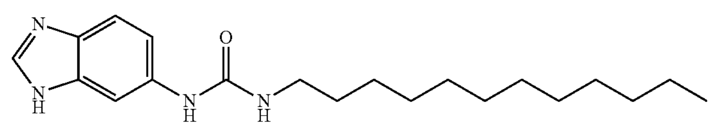 [SMILES: CCCCCCCCCCCCNC(=O)Nc1ccc2nc[nH]c2c1] | 5021 |
| 1569 | 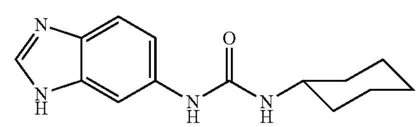 [SMILES: O=C(Nc1ccc2nc[nH]c2c1)NC1CCCCC1] | 457 |
| 1570 | 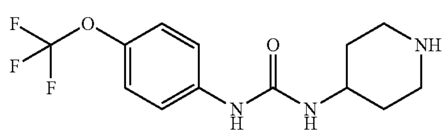 [SMILES: O=C(Nc1ccc(OC(F)(F)F)cc1)NC1CCNCC1] | 2316 |
| 1590 | 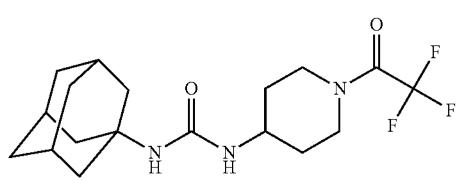 [SMILES: O=C(NC1CCN(C(=O)C(F)(F)F)CC1)NC12CC3CC(CC(C3)C1)C2] | 1.1 |
| 1591 | 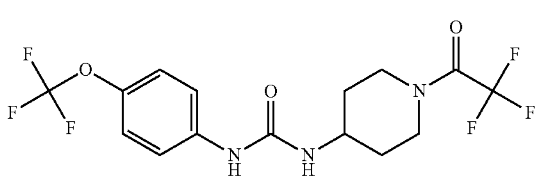 [SMILES: O=C(Nc1ccc(OC(F)(F)F)cc1)NC1CCN(C(=O)C(F)(F)F)CC1] | 0.4 |

TABLE 5a-continued

Inhibition of human sEH by 1-substituted-3-n-(substituted)heterocyclic areas, carbamates and amides:

| Compound | Structure | IC$_{50}$ (nM) |
|---|---|---|
| 1602 | 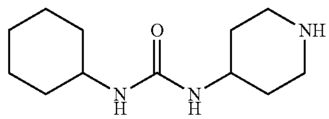 [SMILES: O=C(NC1CCCCC1)NC1CCNCC1] | 561.7 |
| 1604 | 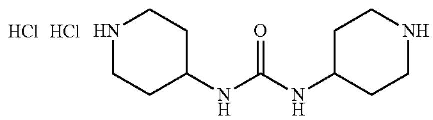 [SMILES: Cl ; Cl ; O=C(NC1CCNCC1)NC1CCNCC1] | 100000 |
| 1605 | 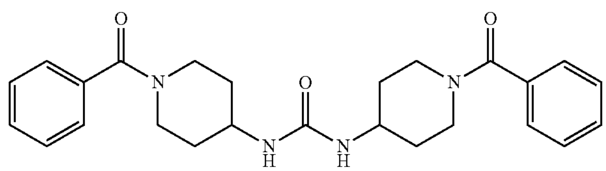 [SMILES: O=C(NC1CCN(C(=O)c2ccccc2)CC1)NC1CCN(C(=O)c2ccccc2)CC1] | 4.8 |
| 1606 | 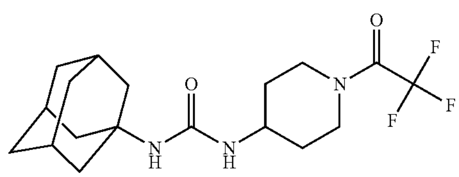 [SMILES: O=C(NC1CCN(C(=O)C(F)(F)F)CC1)NC12CC3CC(CC(C3)C1)C2] | 1.7 |
| 1641 | 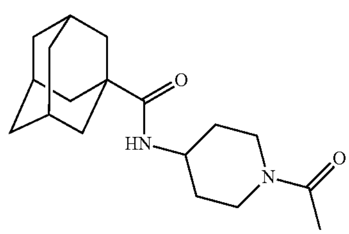 [SMILES: CC(=O)N1CCC(NC(=O)C23CC4CC(CC(C4)C2)C3)CC1] | 12649.3 |
| 1642 | 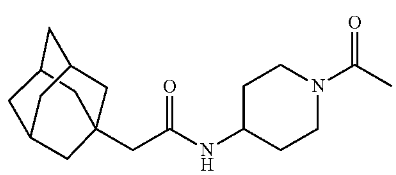 [SMILES: CC(=O)N1CCC(NC(=O)CC23CC4CC(CC(C4)C2)C3)CC1] | 275.1 |
| 1643 | 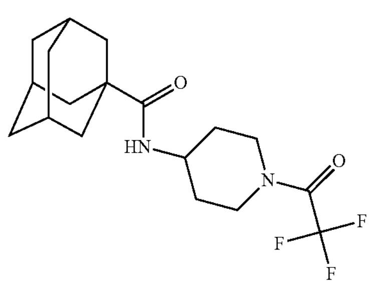 [SMILES: O=C(N1CCC(NC(=O)C23CC4CC(CC(C4)C2)C3)CC1)C(F)(F)F] | 4208.9 |
| 1644 | 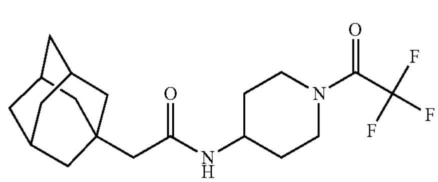 [SMILES: O=C(CC12CC3CC(CC(C3)C1)C2)NC1CCN(C(=O)C(F)(F)F)CC1] | 28.3 |

TABLE 5a-continued

Inhibition of human sEH by 1-substituted-3-n-(substituted)heterocyclic areas, carbamates and amides:

| Compound | Structure | IC$_{50}$ (nM) |
|---|---|---|
| 1645 | 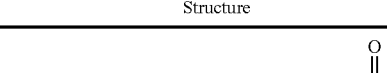 | 27.6 |

TABLE 5b

| Structure | Compound # | IC50 (nM) |
|---|---|---|
| 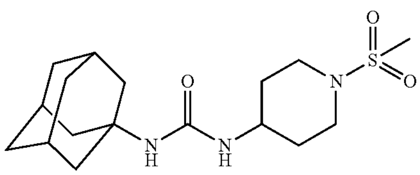 [SMILES: CS(=O)(=O)N1CCC(NC(=O)NC23CC4CC(CC(C4)C2)C3)CC1] | 1701 | 1.4 |
| 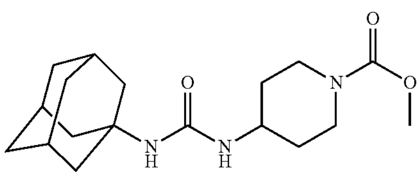 [SMILES: COC(=O)N1CCC(NC(=O)NC23CC4CC(CC(C4)C2)C3)CC1] | 1702 | 0.9 |
| 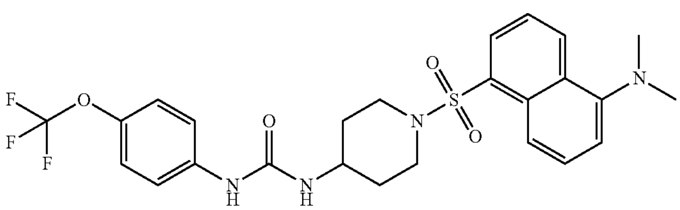 [SMILES: CN(C)c1cccc2c(S(=O)(=O)N3CCC(NC(=O)Nc4ccc(OC(F)(F)F)cc4)CC3)cccc12] | 1710 | 0.8 |
| 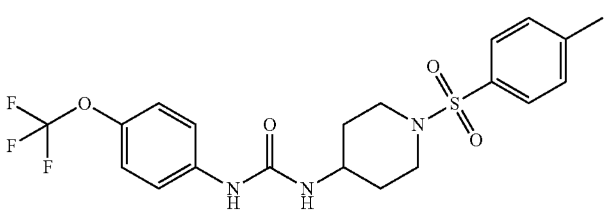 [SMILES: Cc1ccc(S(=O)(=O)N2CCC(NC(=O)Nc3ccc(OC(F)(F)F)cc3)CC2)cc1] | 1711 | 0.4 |

Example 77

Pharmacokinetic Screening Procedure

This example provides the pharmacokinetic studies, specifically serum profiles carried out using sEH inhibitory compounds of the present invention in dogs. As noted above, the use of 1-substituted urea inhibitors afforded exquisite sensitivity, allowing the determination of the determined pharmacokinetic parameters from serial blood samples collected from individual dogs (see Tables 6-8).

Animals.

Healthy dogs, 5-6 years-old, were assigned to study groups based on body-weight stratified randomization procedure. The body weight of animals used in all the experiments was about 20 kg. Dogs were maintained on a natural light/dark cycle under standard kennel conditions, with food and water available ad libid um.

Drug Preparation, Administration, Blood Sample Drawing.

Various amounts of a compound was dissolved in 1 mL. of Crisco, heated and sonicated for 15 minutes to dissolve fire compounds. The mixture was transferred in solution to a syringe with a cap. The mixture becomes a solid at room temperature and may the kept in a refrigerator until used. sEH inhibitors were administered orally to dogs via syringe. The compounds are administered at room temperature or warmer so that they are in preferably in solution. The dogs are fed immediately thereafter.

Serial blood samples (100 μL) were collected from a catheter inserted in the right front leg of the dog. Serial blood samples were collected in EDTA tubes at various time points (0, 15, 30, 60, 120, 240, 300, 360, 480, and 1440 minutes) after administration. The blood samples are centrifuged at 4000 rpm for 10 minutes and the plasma is collected into micro-centrifuge tubes and frozen at −80° C.

Plasma Sample Preparation for LC/Ms Measurement and Analysis 100 uL of plasma was collected in another Eppendorf. 200 μL of water and 500 μL of ethyl acetate is added and the mixture was vortexed. 10 uL of surrogate was added and the mixture was vortexed again. The mixture was centrifuged for 6000 rpm for 5 min. and the organic phase was then extracted into another Eppendorf. Another 500 uL of ethyl acetate is added to the water phase and the mixture is extracted again. The organic phase is dried under nitrogen and the samples reconstituted with 50 μL of MeOH and at least one internal standard as added to the plasma mixture (e.g. as extraction standard). Aliquots (5 μL) were injected onto the LC-MS/MS system. For measuring parent compounds and their metabolites by using LC-MS/MS: a Waters 2790 liquid chromatograph equipped with a 30×2.1 mm 3 μm C18 Xterra™ column (Waters) and a Micromass Quattro Ultima triple quadrupole tandem mass spectrometer (Micromass, Manchester, UK) was used.

Analysis.

Pharmacokinetics analysts was performed using Sigma-Plot software system (SPSS science, Chicago, Ill.). A one-compartment model was used for blood concentration-time profiles for the oral gavage dosing and fits to the following equation (see, Gibson, G. G. and Skett, P.: INTRODUCTION TO DRUG METABOLISM, SECOND ED., Chapman and Hall, New York 1994, 199-210):

$$C = ae^{-bt}$$

The half-life ($t_{1/2}$) for the elimination phase was calculated by the following equation:

$$t_{1/2} = 0.693/b$$

The area under the concentration (AUC) was calculated by the following equation:

$$AUC = a/b$$

Where:
C = the total blood concentration at time t
a = the extrapolated zero intercept
b = the apparent first-order elimination rate constant The results shown in Tables 6, 7 and 8 and examples of the time course of compounds is shown in FIGS. 1-3.

TABLE 6

LC/MS analysis

| Time | Compound |||||||||| 
|---|---|---|---|---|---|---|---|---|---|---|
| | 1153 | 1555 | 1606 | 1163 | 1157 | 1159 | 1121 | 1201 | 1204 | 1206 |
| 0 | 0.00 | 0.00 | 0.00 | 0.00 | 0.00 | 0.00 | 0.00 | 0.00 | 0.00 | 0.00 |
| 15 | 288.97 | 16.07 | 0.00 | 5.70 | 0.58 | 7.26 | 4.86 | 9.19 | 0.00 | 0.00 |
| 30 | 276.16 | 45.76 | 1.61 | 16.05 | 5.18 | 7.82 | 3.81 | 32.65 | 0.19 | 0.00 |
| 60 | 241.03 | 100.35 | 4.82 | 31.79 | 7.77 | 4.58 | 1.98 | 42.48 | 0.34 | 0.00 |
| 120 | 107.19 | 216.91 | 9.37 | 24.00 | 9.50 | 1.39 | 0.42 | 21.09 | 0.11 | 0.00 |
| 180 | 56.41 | 260.79 | 10.98 | 14.55 | 7.05 | 0.60 | 0.16 | 7.15 | 0.00 | 0.00 |
| 240 | 26.42 | 268.90 | 6.83 | 10.05 | 4.60 | 0.00 | 0.06 | 3.16 | 0.00 | 0.00 |
| 300 | 20.81 | 302.64 | 5.62 | 7.20 | 2.45 | 0.00 | 0.05 | 1.72 | 0.00 | 0.00 |
| 360 | 10.10 | | 3.21 | 4.95 | 2.45 | 0.00 | 0.03 | 0.00 | 0.00 | 0.00 |
| 480 | 4.66 | 320.45 | 1.47 | 1.50 | 0.86 | 0.00 | 0.03 | 0.00 | 0.00 | 0.00 |
| 1440 | 0.00 | 266.29 | | 0.00 | 0.00 | 0.00 | 0.04 | 0.00 | 0.00 | 0.00 |

Note the acid moiety makes a big difference in these compounds. The acids reach a maximum concentration faster and gives sustained blood levels. Higher blood levels (bioavailability) generally correspond to higher protein binding and higher efficacy. Accordingly, the presence of an acidic moiety improves the oral availability of these inhibitors.

TABLE 7

Pharmacokinetic parameters of compounds

| Cmpd. (solubility in oil) | Structure | $IC_{50}$ (nM) | AUC (μM * min) | AUCINF_D_pred (min * kg * nM/mg) | AUCINF_D_pred/$IC_{50}$ (AUC/$IC_{50}$) |
|---|---|---|---|---|---|
| 1153 (Opaque) | [structure] | 14.5 | 35.8 | 119214 | 8221 (2.5) |

TABLE 7-continued

| Pharmacokinetic parameters of compounds | | | | | |
|---|---|---|---|---|---|
| Cmpd. (solubility in oil) | Structure | IC$_{50}$ (nM) | AUC (μM * min) | AUCINF_D_pred (min * kg * nM/mg) | AUCINF_D_pred/ IC$_{50}$ (AUC/IC$_{50}$) |
| 1156 | | 5 | 4.9 | | (1.0) |
| 1555 (Opaque) | | 11.5 | 390.1 | 13002825 | 1130680 (33.9) |
| 1606 (Suspension) | | 1.7 | 2.6 | 8553 | 5031 (1.5) |
| 1163 (Opaque) | | 3.19 | 5.6 | 18504 | 5800 (1.75 |
| 1157 (Opaque) | | 2.64 | 2.2 | 7187 | 2722 (0.8) |
| 1159 (Opaque) | | 1.3 | | | |
| 1121 (Not dissolved) | | 3.2 | | | |

TABLE 7-continued

Pharmacokinetic parameters of compounds

| Cmpd. (solubility in oil) | Structure | IC$_{50}$ (nM) | AUC (μM * min) | AUCINF_ D_pred (min * kg * nM/mg) | AUCINF_ D_pred/ IC$_{50}$ (AUC/IC$_{50}$) |
|---|---|---|---|---|---|
| 1201 (Suspension) | 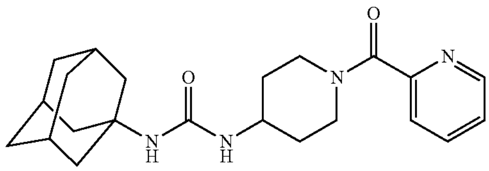 [SMILES: O=C(NC1CCN(C(=O)c2ccccn2)CC1)NC12CC3CC(CC(C3)C1)C2] | 1.2 | 4.8 | 16100 | 13416 (4.0) |
| 1204 (Opaque) | 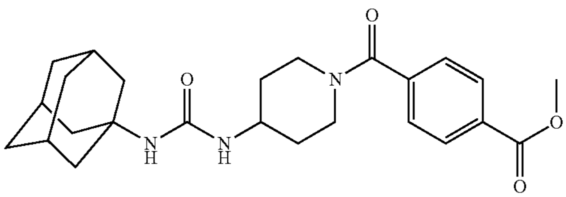 [SMILES: COC(=O)c1ccc(C(=O)N2CCC(NC(=O)NC34CC5CC(CC(C5)C3)C4)CC2)cc1] | 1.1 | | | |
| 1206 (Opaque) | 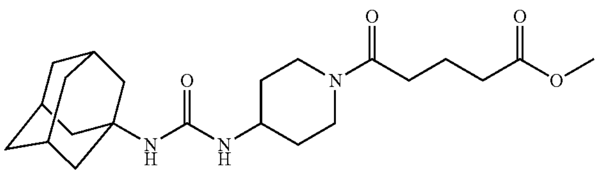 [SMILES: COC(=O)CCCC(=O)N1CCC(NC(=O)NC23CC4CC(CC(C4)C2)C3)CC1] | 2.7 | | | |
| 1642 | 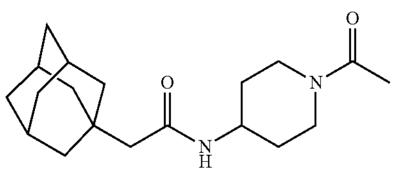 [SMILES: CC(=O)N1CCC(NC(=O)CC23CC4CC(CC(C4)C2)C3)CC1] | 275.1 | 5.8 | | (0.02) |
| 1644 | 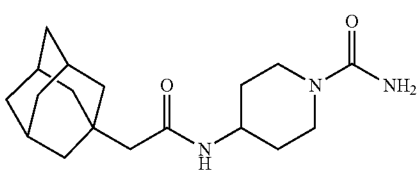 [SMILES: NC(=O)N1CCC(NC(=O)CC23CC4CC(CC(C4)C2)C3)CC1] | 28.3 | | | |
| 1645 | 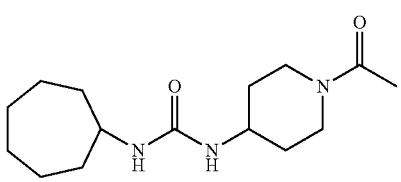 [SMILES: CC(=O)N1CCC(NC(=O)NC2CCCCCC2)CC1] | 27.6 | 220.7 | | (8.0) |
| 1701 | 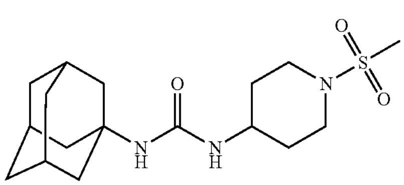 [SMILES: CS(=O)(=O)N1CCC(NC(=O)NC23CC4CC(CC(C4)C2)C3)CC1] | 1.4 | 4.9 | | (3.5) |
| 1702 | 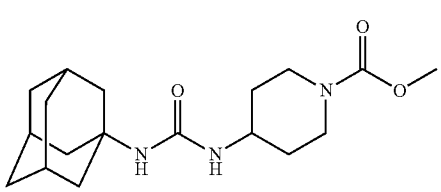 [SMILES: COC(=O)N1CCC(NC(=O)NC23CC4CC(CC(C4)C2)C3)CC1] | 0.9 | 5.4 | | (6.0) |

TABLE 7-continued

Pharmacokinetic parameters of compounds

| Cmpd. (solubility in oil) | Structure | IC$_{50}$ (nM) | AUC (μM * min) | AUCINF_ D_pred (min * kg * nM/mg) | AUCINF_ D_pred/ IC$_{50}$ (AUC/IC$_{50}$) |
|---|---|---|---|---|---|
| 1710 | 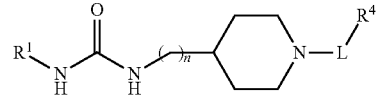 | 0.8 | | | |
| 1711 | 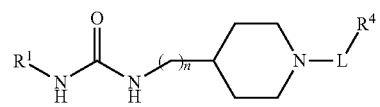 | 0.4 | | | |

TABLE 8

| Time | Compound 1153 in solution at 0.1 mg/kg dose | Compound 1153 in solution at 0.3 mg/kg dose |
|---|---|---|
| 0 | 0.31 | 0.00 |
| 15 | 5.33 | 288.97 |
| 30 | 19.59 | 276.16 |
| 60 | 56.74 | 241.03 |
| 120 | 106.43 | 107.19 |
| 180 | 100.94 | 56.41 |
| 240 | 75.71 | 26.42 |
| 300 | 44.51 | 20.81 |
| 360 | 29.15 | 10.10 |
| 480 | 13.01 | 4.66 |
| 1440 | 0.00 | 0.00 |

What is claimed is:

1. A compound having the formula:

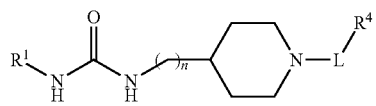

wherein R$^1$ is phenyl, optionally substituted with from 1 to 2 substituents each independently selected from the group consisting C$_1$-C$_8$haloalkyl, and C$_1$-C$_8$haloalkoxy;
L is —CO—;
R$^4$ is selected from the group consisting of C$_1$-C$_8$alkyl, C$_1$-C$_8$haloalkyl and C$_3$-C$_{12}$cycloalkyl; and
the subscript n is 0;
or a pharmaceutically acceptable salt thereof.

2. The compound of claim 1, wherein R$^4$ is selected from the group consisting of C$_1$-C$_8$alkyl and C$_3$-C$_{12}$cycloalkyl.

3. The compound of claim 1, wherein R$^4$ is C$_1$-C$_8$ alkyl.

4. The compound of claim 1, wherein R$^4$ is C$_3$-C$_{12}$cycloalkyl.

5. The compound of claim 1, wherein R$^4$ is C$_1$-C$_8$haloalkyl.

6. The compound of claim 1, selected from the group consisting of:

1-(1-acetyl-piperidin-4-yl)-3-(4-trifluoromethoxyphenyl) urea; and
1-(1-trifluoromethylcarbonylpiperidin-4-yl)-3-(4-trifluoromethoxyphenyl)urea;
or a pharmaceutically acceptable salt thereof.

7. A compound having the formula:

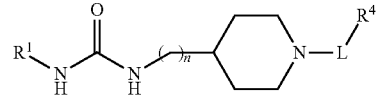

wherein R$^1$ is phenyl, optionally substituted with from 1 to 2 substituents each independently selected from the group consisting of halo, C$_1$-C$_8$haloalkyl, and C$_1$-C$_8$haloalkoxy, wherein when phenyl is substituted with halo, halo is selected from the group consisting of chlorine, bromine and iodine;
L is —CO—;
R$^4$ is C$_3$-C$_{12}$cycloalkyl; and
the subscript n is 0;
or a pharmaceutically acceptable salt thereof.

8. A compound having the formula:

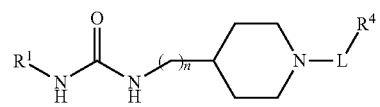

wherein R$^1$ is phenyl, optionally substituted with from 1 to 2 substituents each independently selected from the group consisting of halo, C$_1$-C$_8$haloalkyl, and C$_1$-C$_8$haloalkoxy, wherein when phenyl is substituted with halo, halo is selected from the group consisting of chlorine, bromine and iodine;
L is —CO—;
R$^4$ is C$_1$-C$_8$haloalkyl; and
the subscript n is 0;
or a pharmaceutically acceptable salt thereof.

* * * * *